United States Patent [19]
Jones et al.

[11] Patent Number: 5,459,062
[45] Date of Patent: Oct. 17, 1995

[54] GRAM-NEGATIVE ALKALIPHILIC MICROORGANISMS

[75] Inventors: Brian E. Jones, VA Leidschendam, Netherlands; William D. Grant, Leicester; Nadine C. Collins, Dorking, both of United Kingdom

[73] Assignee: Gist-Brocades, N.V., Delft, Netherlands

[21] Appl. No.: 122,745

[22] Filed: Sep. 16, 1993

Related U.S. Application Data

[63] Continuation-in-part of Ser. No. 46,878, Apr. 8, 1993, abandoned, which is a continuation-in-part of Ser. No. 903,786, Jun. 24, 1992, abandoned, which is a continuation-in-part of Ser. No. 719,307, Jun. 24, 1991, abandoned, which is a continuation-in-part of Ser. No. 562,863, Aug. 6, 1990, abandoned.

[51] Int. Cl.$^6$ ............................................. C12N 1/20
[52] U.S. Cl. ................... 435/252.1; 435/252.31; 435/252.4
[58] Field of Search ................ 435/252.31, 252.1, 435/252.4

OTHER PUBLICATIONS

W. D. Grant et al., "Alkaliphiles: ecology, diversity and applications," *FEMS Microbiology Reviews* (1990) 75:255–270.

W. D. Grant et al., "The Alkaline Saline Environment", *Microbes in Extreme Environments*, Academic Press, London (1986) pp. 22–54.

B. J. Tindall, "Prokaryotic Life in the Alkaline, Saline, Athalassic Environment", *Halophilic Bacteria*, CRC Press, Boca Raton, Fla. (1988) 1:31–70.

K. Horikoshi et al., "Alkalophilic Microorganisms", *Springer–Verlag, Berlin, Heidelberg, N.Y.* (1982).

H. Shiba, "Superbugs", *Japan Scientific Societies Press, Tokyo and Springer–Verlag, Berlin, Heidelberg, N.Y.* (1991) pp. 191–211.

N. Nakatsugawa, "Superbugs", *Japan Scientific Societies Press, Tokyo and Springer–Verlag, Berlin, Heidelberg, N.Y.* (1991) pp. 212–220.

D. Wang et al., "Natronobacterium from Soda Lakes of China", *Recent Advances in Microbial Ecology*, (Proceedings of the 5th International Symposium on Microbial Ecology, eds. T. Hattori et al.) *Japan Scientific Societies Press, Tokyo* (1989) pp. 68–72.

S. Morth et al., "Variation of Polar Lipid Composition within Haloalkaliphilic Archaebacteria", *System. Appl. Microbiol.* (1985) 6:247–250.

V. Upasani et al., "Sambhar Salt Lake, Chemical composition of the brines and studies on haloalkaliphilic archaebacteria", *Arch. Microbiol.* (1990) 154:589–593.

*Primary Examiner*—Herbert J. Lilling
*Attorney, Agent, or Firm*—Morrison & Foerster

[57] ABSTRACT

Gram-negative bacteria, which are obligate alkaliphiles, have been isolated from samples of soil, water and sediment and a number of other sources obtained from in and around soda lakes. These bacteria have been analyzed according to the principles of numerical taxonomy with respect to each other, as well as to a variety of known bacteria. In addition, these bacteria are further circumscribed by an analysis of various chemotaxonomic characteristics. The bacteria produce various alkali-tolerant enzymes which may be used in various industrial processes requiring such enzymatic activity in a high pH environment.

28 Claims, 9 Drawing Sheets

GRAM-NEGATIVE ALKALIPHILIC MICROORGANISMS

This application is a continuation-in-part of U.S. Ser. No. 08/046,878, filed Apr. 8, 1993, which is a continuation-in-part of U.S. Ser. No. 07/903,786, filed Jun. 24, 1992, which is a continuation-in-part of U.S. Ser. No. 07/719,307, filed Jun. 24, 1991, which is a continuation-in-part of U.S. Ser. No. 07/562,863, filed Aug. 6, 1990, all abandoned, all of which are incorporated herein by reference.

The present invention is in the field of microbiology and more particularly in the field of alkaliphilic microorganisms.

BACKGROUND OF THE INVENTION

Alkaliphiles are defined as organisms which exhibit optimum growth in an alkaline pH environment, particularly in excess of pH 8, and generally in the range between pH 9 and 10. Alkaliphiles may also be found living in environments having a pH as high as 12. Obligate alkaliphiles are incapable of growth at neutral pH.

Alkaliphiles may be found in such everyday environments as garden soil, presumably due to transient alkaline conditions caused by biological activity such as ammonification, sulphate reduction or photosynthesis. A much richer source of a greater variety of alkaliphilic organisms may be found in naturally occurring, stable alkaline environments such as soda lakes.

A more detailed study of soda lakes and alkaliphilic organisms in general is provided in Grant, W. D., Mwatha, W. E. and Jones, B. E. ((1990) FEMS Microbiology Reviews, 75, 255– 270), the text of which is hereby incorporated by reference. Lists of alkaline soda lakes may be found in the publications of Grant, W. D. and Tindall, B. J. in *Microbes in Extreme Environments,* (eds. R. A. Herbert and G. A. Codd); Academic Press, London, (1986), pp. 22–54; and Tindall, B. J. in *Halophilic Bacteria,* Volume 1, (ed. F. Rodriguez-Valera); CRC Press Inc., Boca Raton, Fla., (1988), pp. 31–70, both texts are also hereby incorporated by reference.

Alkaliphiles, the majority of which are Bacillus species, have been isolated from non-saline environments and are discussed by Horikoshi, K. and Akiba, T. in *Alkalophilic Microorganisms* (Springer-Verlag, Berlin, Heidelberg, N.Y., (1982)). However, alkaliphilic organisms from saline and alkaline environments such as lakes are not discussed therein. Strictly anaerobic bacteria from alkaline, hypersaline, environments have been recently described by Shiba, H. in *Superbugs* (eds. K. Horikoshi and W. D. Grant); Japan Scientific Societies Press, Tokyo and Springer-Verlag, Berlin, Heidelberg, N.Y., (1991), pp. 191–211; and by Nakatsugawa. N., ibid, pp. 212–220.

Soda lakes, which may be found in various locations around the world, are caused by a combination of geological, geographical and climatic conditions. They are characterized by the presence of large amounts of sodium carbonate (or complexes thereof) formed by evaporative concentration, as well as by the corresponding lack of $Ca^{2+}$ and $Mg^{2+}$ which would remove carbonate ions as insoluble salts. Other salts such as NaCl may also concentrate resulting in environments which are both alkaline and saline.

Despite this apparently harsh environment, soda lakes are nevertheless home to a large population of prokaryotes, a few types of which may dominate as permanent or seasonal blooms. The organisms range from alkaliphilic cyanobacteria to haloalkaliphilic archaeobacteria. Moreover, it is not unusual to find common types of alkaliphilic organisms inhabiting soda lakes in various widely dispersed locations throughout the world such as in the East African Rift Valley, in the western U.S., Tibet, China and Hungary. For example, natronobacteria have been isolated and identified in soda lakes located in China (Wang, D. and Tang, Q., *"Natronobacterium* from Soda Lakes of China" in *Recent Advances in Microbial Ecology* (Proceedings of the 5th International Symposium on Microbial Ecology, eds. T. Hattori et al.); Japan Scientific Societies Press, Tokyo, (1989), pp. 68–72) and in the western U.S. (Morth, S. and Tindall, B. J. (1985) System. Appl. Microbiol., 6, 247–250). Natronobacteria have also been found in soda lakes located in Tibet (W. D. Grant, unpublished observations) and India (Upasani, V. and Desai, S. (1990) Arch. Microbiol., 154, pp. 589–593).

Alkaliphiles have already made an impact in the application of biotechnology for the manufacture of consumer products. Alkali-tolerant enzymes produced by alkaliphilic microorganisms have already found use in industrial processes and have considerable economic potential. For example, these enzymes are currently used in detergent compositions and in leather tanning, and are foreseen to find applications in the food, waste treatment and textile industries. Additionally, alkaliphiles and their enzymes are potentially useful for biotransformations, especially in the synthesis of pure enantiomers.

SUMMARY OF THE INVENTION

The present invention provides pure cultures of novel aerobic, Gram-negative alkaliphilic bacteria. These bacteria have been isolated from samples of soil, water, sediment and a number of other sources, all of which were obtained from in and around alkaline soda lakes. These alkaliphiles have been analyzed according to the principles of numerical taxonomy with respect to each other and also to a variety of known bacteria in order to confirm their novelty. In addition, these bacterial taxa are further circumscribed by an analysis of various chemotaxonomic characteristics.

The present invention also provides data as to the composition of the environments from which the samples containing the microorganisms were obtained, as well as the media required for their efficient isolation and culturing such that one of ordinary skill may easily locate such an environment and be able to isolate the organisms of the present invention by following the procedures described herein.

It is also an object of the present invention to provide microorganisms which produce useful alkali-tolerant enzymes, as well as methods for obtaining substantially pure preparations of these enzymes. These enzymes are capable of performing their functions at high pH which makes them uniquely suited for applications requiring such extreme conditions. For example, alkali-tolerant enzymes may be employed in detergent compositions, in leather tanning and in the food, waste treatment and textile industries, as well as for biotransformations such as the production of pure enantiomers.

The genes encoding these alkali-tolerant enzymes may be isolated, cloned and brought to expression in compatible expression hosts to provide a source of larger volumes of enzyme products which may be, if desired, more easily purified and used in various industrial applications, should the wild-type strain fail to produce sufficient amounts of the desired enzyme, or does not ferment well.

DETAILED DESCRIPTION OF THE INVENTION

Sampling

Figure 1A:
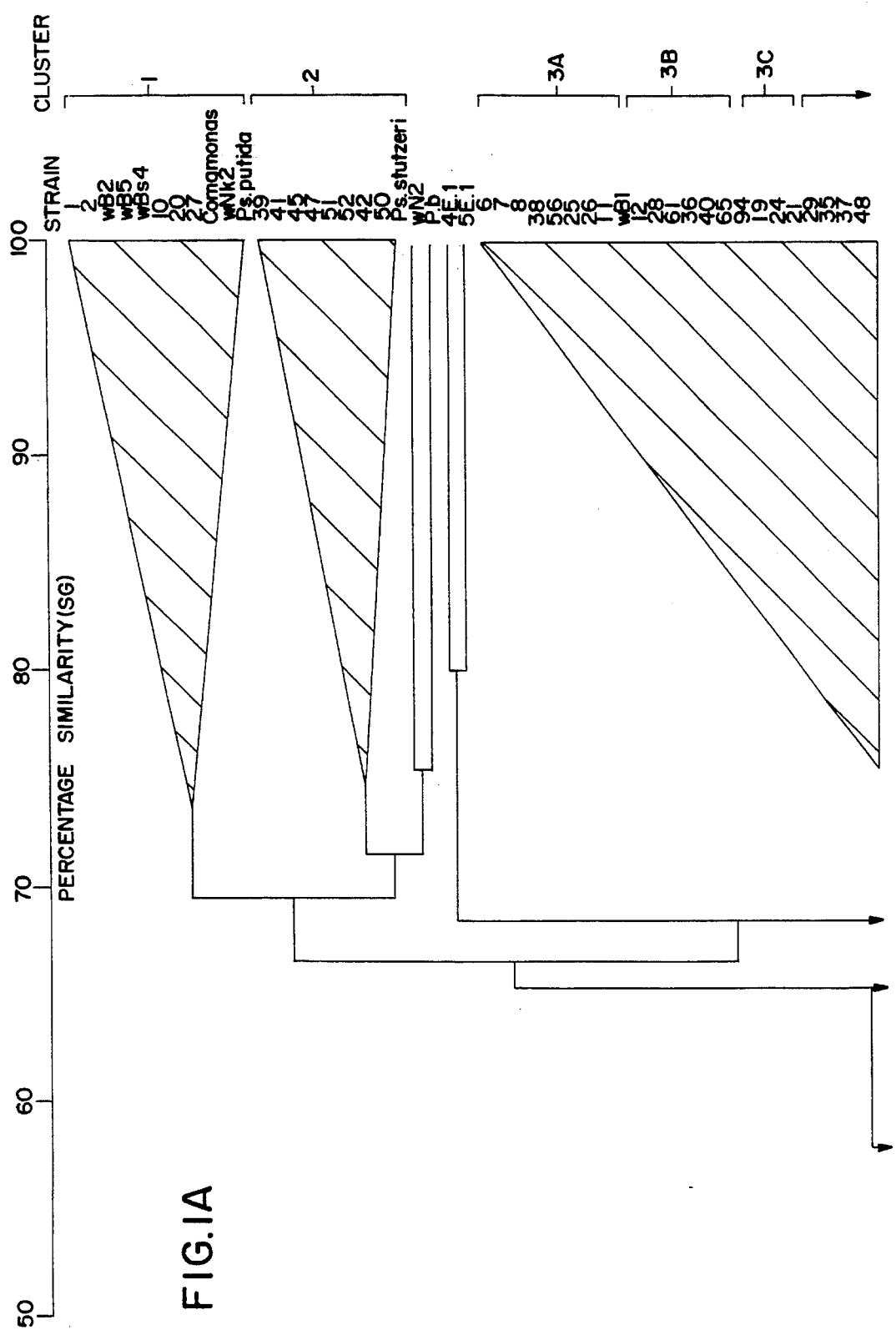
FIG. 1. (Sheet 1 and Sheet 2) Simplified dendrogram showing different clusters (phenons) Sheet 1 and Sheet 2 obtained with the $S_G$ coefficient and Unweighted Average Linkage procedure.

Several hundreds of strains of bacteria have been isolated from samples of soil, water, sediment and a number of other sources in and around alkaline lakes. These samples were obtained as part of an investigation over a period of three years. The isolated bacteria are non-phototrophic eubacteria. Up until now, such bacteria have not been well characterized.

The samples were collected in sterile plastic bags. Sampling was conducted at lakes Elmenteita, Nakuru, Bogoria, Crater (Sonachi), Little Naivasha (Oloidien), Magadi, and Little Magadi (Nasikie Engida), all of which are located in Kenya, East Africa. Alkaline soda lakes having similar environments may also be found in Tibet, China, Hungary and the western U.S. At each sampling site, physical parameters such as pH, conductivity and temperature were measured as well as the physical appearance of the site and the sample. Some of the samples were treated locally within 36 hours of collection of the sample but the majority were examined offsite, several weeks after collection.

Table 1 lists various strains which have been isolated. The strains are listed according to the location from which the sample was taken, the physical appearance of the sample itself and a reference to Table 2 which provides the chemical analysis of the lake water samples.

Table 3 provides a list of the isolated strains arranged according to the results of the numerical taxonomic analysis. Furthermore, Table 3 provides physical properties of the sample, in particular the temperature, conductivity and alkaline pH, as well as the numerous isolation media required for obtaining pure cultures of the new bacteria. These media are letter coded with reference to Appendix A.

Tables 1, 2 and 3 provide data from which the environment of the sampling locations may be characterized. The chemical and physical analysis of the samples confirm the presence of alkaline pH, as well as the presence of unusually high levels of $Na_2CO_3$, coupled with low levels of $Ca^{2+}$ and $Mg^{2+}$.

No chemical analysis is available for mud samples. Furthermore, no chemical analysis is available for a few samples (see Table 1). However, other samples taken at the same location have been analyzed and are described in Tables 1–3. It is known that the basic environments of soda lakes are stable with respect to their pH and ionic composition. Moreover, the microbial populations found at these sites remain largely stable. Thus, it is to be expected that despite the lack of a chemical analysis of certain samples, the environment from which the bacteria were obtained may nonetheless be determined from the data presented in Tables 1–3.

The fresh soda-lake water samples were plated out on an alkaline nutrient medium (Medium A) soon after collection. Microscopic inspection showed an unexpectedly high diversity of bacterial types. Considering the extremely alkaline nature of the environment, viable counts showed unexpectedly high numbers of organotrophic bacteria, in the range of $10^5$–$10^6$ colony forming units per ml. The samples were stored either cooled or at ambient temperatures. After a few weeks' storage, the total numbers of bacteria in the sample rose, whereas the diversity of types decreased.

TABLE 1

Alkaliphilic Strains Arranged According to Their Place of Origin

| STRAINS | SAMPLE LOCATION | SAMPLE APPEARANCE | ANALYSIS (Table 2) |
| --- | --- | --- | --- |
| 1E.1, 2E.1, 4E.1, 5E.1, 35E.2, 36E.2, 37E.2, 38E.2 | Lake Elmenteita (east bay) | Mud from dried up lake bed | N.R. |
| wE.5, wE11, wE12 | Lake Elmenteita (east bay) | Sediment and water, littoral zone | N.T. |
| 39E.3, 40E.3, 41E.3, 42E.3, 44E.3, 53E.4, 56E.4 | Lake Elmenteita (east bay) | Mud and water littoral zone. Spirulina scum | 1 |
| 45E.3, 47E.3, 57E.4 | Lake Elmenteita swamp, south- | Brown water and sediment east arm | 2 |
| 48E.3, 58E.4 | Lake Elmenteita swamp, south- | Grey mud | 2 |
| 59E.4 | Lake Elmenteita, (north-west bay) | Water and sandy sediment, littoral zone | 3 |
| 16N.1, 17N.1, 18N.1, 19N.1, 20N.1, 26N.1, 28N.1, wN1, wN2, wNk1, wNk2 | Lake Nakuru, north beach between Hippo Point and Njoro Point. | Mud and water, littoral zone. | N.T. |
| 49N.3, 50N.3, | Lake Nakuru, | Water column, | 4 |

TABLE 1-continued

Alkaliphilic Strains Arranged According to Their Place of Origin

| STRAINS | SAMPLE LOCATION | SAMPLE APPEARANCE | ANALYSIS (Table 2) |
|---|---|---|---|
| 61N.4 | north beach between Hippo Point and Njoro Point. | littoral zone. | |
| 51N.3, 52N.3 | Lake Nakuru, north beach between Hippo Point and Njoro Point. | Lake sediment, littoral zone. | 4 |
| 63N.4 | Lake Nakuru; water hole, SW salt flats | Mud and water | N.T. |
| 6B.1, 7B.1, 8B.1, 9B.1, 10B.1, 24B.1, 25B1, wB1, wB2, wB4, wB5 wBn4 | Lake Bogoria, northern mud flats | Mud and water, littoral zone | N.T. |
| 64B.4 | Lake Bogoria, northern mud flats | Dried crust of soda mud | N.R. |
| 65B.4 | Lake Bogoria, northern mud flats | Mud at water line | 5 |
| wBs4 | Lake Bogoria, south-west shore | Mud and water, littoral zone | N.T. |
| 11C.1, 12C.1, 29C.1, | Crater Lake, North point | Mud and water, littoral zone | N.T. |
| 73aC.4, 73bC.4, 74C.4 | Crater Lake, North point | | 6 |
| 75C.4 | Crater Lake, North point | Soda-mud, shore line | N.R. |
| 77LN.4, 78LN.4 | Little Lake Naivasha, south shore | Water column and sediment | 7 |
| 21M.1, 22M.1, 27M.1 | Lake Magadi, causeway upper western arm | Mud and water | N.T. |
| 92LM.4, 94LM.4 | Little Lake Magadi, north-west springs | Spring water and sediment | 8 |

N.T. = not tested
N.R. = not relevant

TABLE 2

Chemical Analysis of Kenyan Soda Lake Waters

| ANALYSIS | $Na^+$ (mM) | $K^+$ (mM) | $Ca^{2+}$ (mM) | $Mg^{2+}$ (mM) | $SiO_2$ (mM) | $PO_4^{3-}$ (mM) | $Cl^-$ (mM) | $SO_4^{2-}$ (mM) | $CO_3^{2-}$ (mM) | TON (mM) | TA§ |
|---|---|---|---|---|---|---|---|---|---|---|---|
| 1 | 196 | 3.58 | 0.07 | b.l.d. | 2.91 | 0.03 | 65.1 | 2.0 | 68.0 | 0.8 | 119 |
| 2 | 140 | 3.32 | 0.48 | 0.13 | 1.85 | 0.02 | 46.8 | 1.7 | 32.0 | 1.2 | 86 |
| 3 | 167 | 3.32 | 0.06 | b.l.d. | 3.10 | 0.03 | 51.8 | 1.7 | 64.0 | 2.2 | 103 |
| 4 | 326 | 5.63 | 0.15 | b.l.d. | 3.25 | 0.15 | 57.5 | 0.5 | 198.3 | 1.9 | 259 |
| 5 | 735 | 5.50 | 0.21 | 0.01 | 2.23 | 0.09 | 100.9 | 1.0 | 476.7 | 0.9 | 612 |
| 6 | 140 | 8.95 | 0.06 | 0.01 | 2.13 | 0.04 | 12.4 | 0.8 | 90.0 | 1.1 | 133 |
| 7 | 8.7 | 1.79 | 0.28 | 0.65 | 1.02 | 0.003 | 4.8 | 0.5 | <10.0 | <0.07 | 18 |
| 8 | 483 | 4.35 | 0.03 | 0.03 | 0.64 | 0.08 | 157.8 | 1.7 | 166.0 | 1.2 | 105 | b.l.d. = below the limits of detection
*TON = Total Organic Nitrogen
§TA = Total Alkalinity in milliequivalents/liter

TABLE 3

Origin of the Strains Arranged by Cluster*

| CLUSTER | STRAIN | LOCATION | SAMPLE pH | Temp. °C. | Conductivity mS/cm | ISOLATION MEDIUM |
|---|---|---|---|---|---|---|
| 1 | 1E.1<sup>CT</sup> | Elmenteita | 9.5 | 35 | n.t. | A |
| 1 | 2E.1 | Elmenteita | 9.5 | 35 | n.t. | A |
| 1 | wB2 | Bogoria | n.t. | n.t. | n.t. | A |
| 1 | wB5 | Bogoria | n.t. | n.t. | n.t. | A |
| 1 | wBs4 | Bogoria | 10.5 | n.t. | 19 | A |
| 1 | 10B.1 | Bogoria | 10.5 | 36 | 45 | A |
| 1 | 20N.1 | Nakuru | 10.5 | 36 | 30–40 | A |
| 1 | 27M.1 | Magadi T | 11.0 | 36 | 100 | A |
| 1 | | *Comamonas terrigena* (NCIMB 8193) | | | | |
| 1 | wNk2 | Nakuru | 10.5 | n.t. | 19 | A |
| 1 | | *Pseudomonas putida*<sup>T</sup> (NCIMB 9494) | | | | |
| 2 | 39E.3 | Elmenteita | 10–10.5 | 23 | 13.9 | N |
| 2 | 41E.3 | Elmenteita | 10–10.5 | 23 | 11.3 | N |
| 2 | 45E.3 CT | Elmenteita | 10 | 27 | 11.3 | P |
| 2 | 47E.3 | Elmenteita | 10 | 27 | 11.3 | O |
| 2 | 51N.3 | Nakuru | 10–10.5 | 29 | 40.1 | P |
| 2 | 52N.3 | Nakuru | 10–10.5 | 29 | 40.1 | P |
| 2 | 42E.3 | Elmenteita | 10–10.5 | 23 | 13.9 | N |
| 2 | 50N.3 | Nakuru | 10–10.5 | 29 | 40.1 | N |
| 2 | | *Pseudomonas stutzeri*<sup>T</sup> (NCIMB 11358) | | | | |
| — | wN2 | Nakuru | n.t. | n.t. | n.t. | A |
| — | | *Pseudomonas beijerinckii*<sup>T</sup> (NCIMB 9041) | | | | |
| — | 4E.1 | Elmenteita | 9.5 | 35 | n.t. | A |
| — | 5E.1 | Elmenteita | 9.5 | 35 | n.t. | A |
| 3 | 6B.1 | Bogoria | 10.5 | 36 | 45 | A |
| 3 | 7B.1 | Bogoria | 10.5 | 36 | 45 | A |
| 3 | 8B.1 | Bogoria | 10.5 | 36 | 45 | A |
| 3 | 38E.2 | Elmenteita | n.t. | n.t. | n.t. | B |
| 3 | 56E.4 | Elmenteita | 10–10.5 | 23 | 13.9 | C |
| 3 | 25B.1 | Bogoria | 10.5 | 36 | 45 | A |
| 3 | 26N.1 | Nakuru | 10.5 | 36 | 30–45 | A |
| 3 | 11C.1 | Crater | 9.0 | 30 | 10 | A |
| 3 | wB1 | Bogoria | n.t. | n.t. | n.t. | A |
| 3 | 12C.1 | Crater | 9.0 | 30 | 10 | A |
| 3 | 28N.1<sup>CT</sup> | Nakuru | 10.5 | 36 | 30–40 | A |
| 3 | 61N.4 | Nakuru | 10–10.5 | 29 | 40.1 | E |
| 3 | 36E.3 | Elmenteita | n.t. | n.t. | n.t. | K |
| 3 | 40E.3 | Elmenteita | 10–10.5 | 23 | 13.9 | M |
| 3 | 65B.4 | Bogoria | n.t. | n.t. | 41.9 | C |
| 3 | 94LM.4 | Little Magadi | 9–9.5 | 81 | 35.0 | L |
| 3 | 19N.1 | Nakuru | 10.5 | 36 | 30–40 | A |
| 3 | 24B.1 | Bogoria | 10.5 | 36 | 45 | A |
| 3 | 21M.1 | Magadi | 11.0 | 36 | 100 | A |
| 3 | 29C.1 | Crater | 9.0 | 30 | 10 | A |
| 3 | 35E.2 | Elmenteita | n.t. | n.t. | n.t. | I |
| 3 | 37E.2 | Elmenteita | n.t. | n.t. | n.t. | I |
| 3 | 48E.3 | Elmenteita | 10.0 | 27 | 11.3 | P |
| 3 | 78LN.4 | Little Naivasha | 8.5–9 | 30 | 1.2 | G |
| 3 | 73aC.4 | Crater | n.t. | n.t. | 10.2 | D |
| 3 | 75C.4 | Crater | n.t. | n.t. | n.t. | H |
| 3 | 73bC.4 | Crater | n.t. | n.t. | 10.2 | D |
| 3 | 74C.4 | Crater | n.t. | n.t. | 10.2 | H |
| 3 | 77LN.4 | Little Naivasha | 8.5–9 | 30 | 1.2 | F |
| 3 | wN1 | Nakuru | n.t. | n.t. | n.t. | A |
| 3 | 49N.3 | Nakuru | 10–10.5 | 29 | 40.1 | Q |
| 3 | 44E.3 | Elmenteita | 10.0 | 27 | 13.9 | O |
| 3 | 58E.4 | Elmenteita | 10.0 | 27 | 11.3 | G |
| 3 | 57E.4 | Elmenteita | 10.0 | 27 | 11.3 | C |
| 4 | wE5 | Elmenteita | n.t. | n.t. | n.t. | A |
| 4 | wB4<sup>CT</sup> | Bogoria | n.t. | n.t. | n.t. | A |
| 4 | wNk1 | Nakuru | 10.5 | n.t. | n.t. | A |
| 4 | wE11 | Elmenteita | 10.4 | n.t. | 13 | A |
| 4 | wE12 | Elmenteita | 10.4 | n.t. | 13 | A |
| 5 | 9B.1 | Bogoria | 10.5 | 36 | 45 | A |
| 5 | 16N.1 | Nakuru | 10.5 | 36 | 30–40 | A |
| 5 | 17N.1<sup>CT</sup> | Nakuru | 10.5 | 36 | 30–40 | A |
| 5 | 22M.1 | Magadi | 11.0 | 36 | 100 | A |
| 5 | 18N.1 | Nakuru | 10.5 | 36 | 30–40 | A |
| 5 | 59E.4 | Elmenteita | 10.0 | 31–33 | 12.7 | G |
| 5 | 64B.4<sup>CT</sup> | Bogoria | n.t. | n.t. | n.t. | E |

TABLE 3-continued

Origin of the Strains Arranged by Cluster*

| CLUSTER | STRAIN | SAMPLE LOCATION | pH | Temp. °C. | Conductivity mS/cm | ISOLATION MEDIUM |
|---|---|---|---|---|---|---|
| 5 | 63N.4 | Nakuru | 9.0 | n.t. | n.t. | C |
| 5 | 53E.4 | Elmenteita | 10–10.5 | 23 | 13.9 | G |
| — | 92LM.4 | Little Magadi | 9–9.5 | 81 | 35.0 | L |
| — | wBn5 | Bogoria | 10.5 | n.t. | 19 | A |

*Clusters of microorganisms are obtained by analysis according to the principles of numerical taxonomy using the $S_G$/UPGMA method (see discussion below and FIG. 1).
n.t. = not tested
The letter codes given for the Isolation Media refer to Appendix A.

Treatment of the Samples: Enrichment and Isolation of Alkaliphilic Bacteria

A wide diversity of enrichment and isolation methods were applied. Some of the methods were specifically designed for the enrichment and isolation of alkaliphilic bacteria which exhibit specific types of enzyme activity at an alkaline pH. Other techniques of a more general nature were applied for the isolation of diverse sorts of alkaliphilic bacteria. In some cases, the specific conditions prevailing in the lakes (Table 2) were taken into account when experiments were performed for the isolation of bacteria.

The different nutrient media employed for the isolation of the new alkaliphilic bacteria are designated Medium A-Medium Q. The composition of the various media employed is shown in Appendix A.

For the isolation of non-specific alkaliphilic organotrophic bacteria, soda-lake water samples or dilutions thereof were streaked out on an alkaline nutrient agar, pH 10–pH 10.5 (Medium A). Samples of a more solid consistency, mud, sediment, etc. were first suspended in an alkaline nutrient broth (Medium A) before spreading on an alkaline nutrient agar (Medium A). The bacteria were cultivated in a heated incubator, preferably at 37° C. In some cases, the samples were suspended in an alkaline nutrient broth (Medium A) and the bacteria cultivated by shaking, preferably at 37° C. for 2–3 days before spreading the broth onto an alkaline nutrient agar (Medium A) for the isolation of bacterial colonies.

For the isolation of alkaliphilic bacteria exhibiting specific types of enzyme activity, samples were spread onto alkaline nutrient agar containing specific substrates such as lactalbumin or casein or olive oil. In some instances, the bacteria in the sample may be enriched for 1 day or several weeks in a non-specific alkaline nutrient broth such as Medium A before spreading the broth onto an alkaline nutrient agar specific for the detection of bacteria exhibiting enzyme activity such as lipolytic or proteolytic activity.

Taxonomic Analysis

Seventy strains of bacteria isolated from in and around alkaline lakes were assigned to the type of bacteria known as Gram-negative bacteria on the basis of (1) the Dussault modification of the Gram's staining reaction (Dussault, H. P., (1955), J. Bacteriol., 7.0, 484–485); (2) the KOH sensitivity test (Gregersen, T., (1978), Eur. J. Appl. Microbiol. and Biotech. 5, 123–127; Halebian, S. et al., (1981), J. Clin. Microbiol., 13, 444–448); (3) the aminopeptidase reaction (Cerny, G., (1976), Eur. J. Appl. Microbiol., 3, 223–225; ibid, (1978), 5, 113–122); and in many cases, confirmation also on the basis of (4) a quinone analysis (Collins, M.D. & Jones, D., (1981), Microbiol. Rev., 45, 316–354) using the method described by Collins, M. D. in *Chemical Methods in Bacterial Systematics* (eds. M. Goodfellow & D. Minnikin) pp. 267–288, Academic Press, London, 1985.

The seventy strains were tested for 104 characters. The results were analyzed using the principles of numerical taxonomy (Sneath, P. H. A. and Sokal, R. R., in *Numerical Taxonomy*, W. H. Freeman & Co., San Francisco, 1973). The characters tested and how they were tested are compiled in Appendix B. In addition, Appendix C records how each character was coded for taxonomic analysis.

Since there are no well-documented strict or obligate non-phototrophic, alkaliphilic Gram-negative eubacteria known to the inventors, a diverse collection of 20 known Gram-negative bacteria were subjected as controls to the same analysis, using modified pH conditions. These 20 known reference bacteria are recorded in Table 4 from which it will be seen that in most cases the "Type Strain" of the known species has been used.

TABLE 4

Gram-Negative Non-Alkalinhilic Reference Strains

| * | |
|---|---|
| (C.t.) | *Comamonas terrigena*$^T$ NCIMB 8193 |
| (P.p.) | *Pseudomonas putida*$^T$ NCIMB 9494 |
| (P.s.) | *Pseudomonas stutzeri*$^T$ NCIMB 11358 |
| (A.t.) | "*Alcaligenes tolerans*" Leicester University strain |
| (V.c.) | *Vibrio costicola* $^T$ NCIMB 701 |
| (P.a.) | *Providencia alcalifacien*$^{NT}$ NCTC 10286 |
| (P.v.) | *Proteus vulgaris*$^{NT}$ ATCC 13315 |
| (M.v.) | *Moellerella wisconsensis*$^T$ NCTC 12132 |
| (E.t.) | *Edwardsiella tarda*$^T$ NCTC 10396 |
| (A.h.) | *Aeromonas hydrophila*$^T$ NCTC 8049 |
| (A.s.) | *Aeromonas* sp S5 Leicester University strain |
| (F.a.) | *Flavobacterium aquatile*$^T$ NCIMB 8694 |
| (E.c.) | *Escherichia Coli*$^T$ NCTC 9001 |
| (E.a.) | *Enterobacter aerogenes*$^T$ NCTC 10006 |
| (K.a.) | *Klebsiella pneumonia* ATCC 15380 ("*K. aerogenes*") |
| (H.a.) | *Hafnia alvei*$^T$ ATCC 13337 |
| (C.f.) | *Citrobacter freundii*$^T$ NCTC 9750 |
| (S.m.) | *Serratia marcescens*$^T$ NCTC 10211 |
| (P.b.) | *Pseudomonas beijerinckii*$^T$ NCIMB 9041 |
| (H.e.) | *Halomonas elongata*$^T$ ATCC 33173 |

Figure 1B:
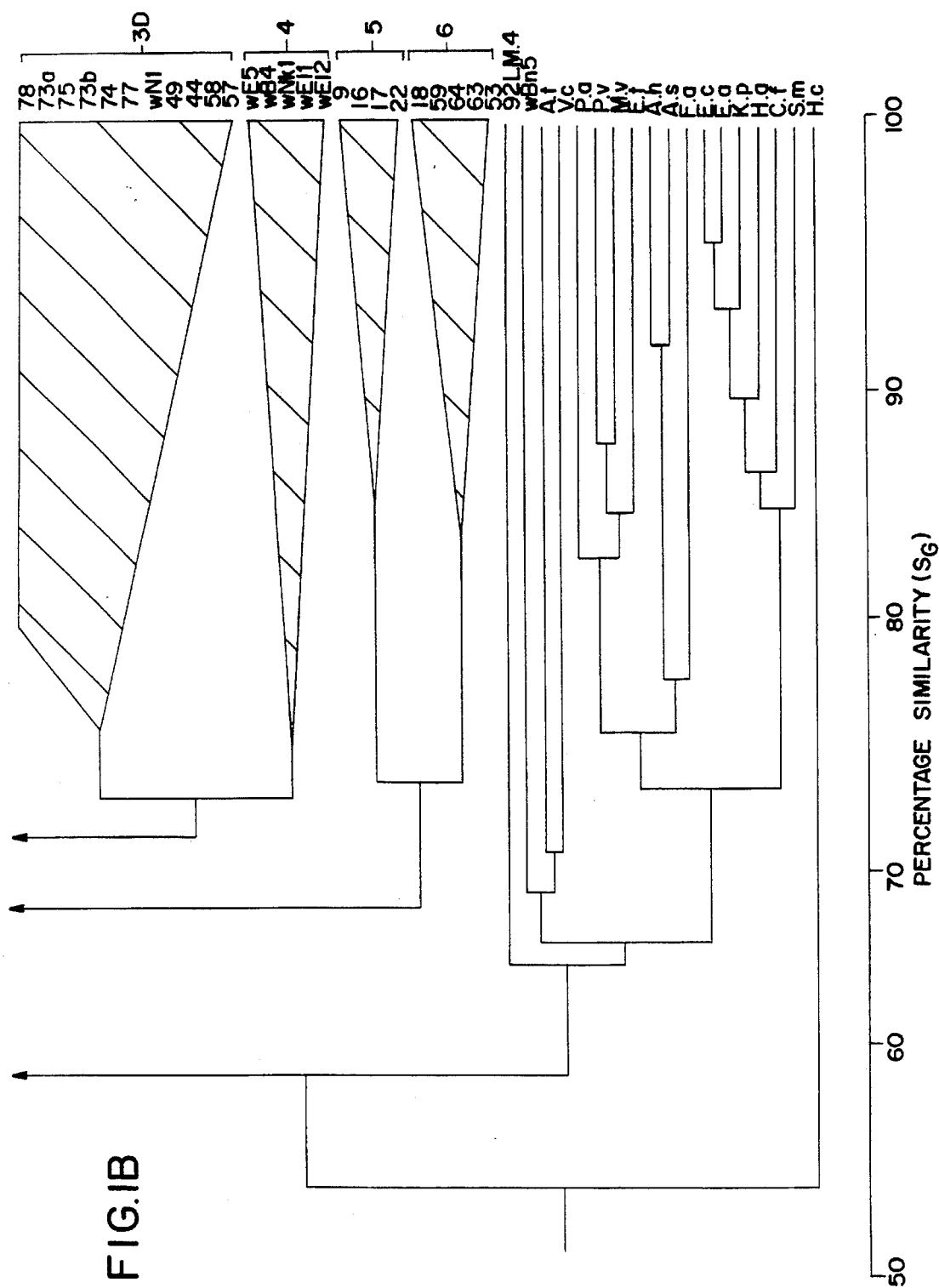
Figure 2A:
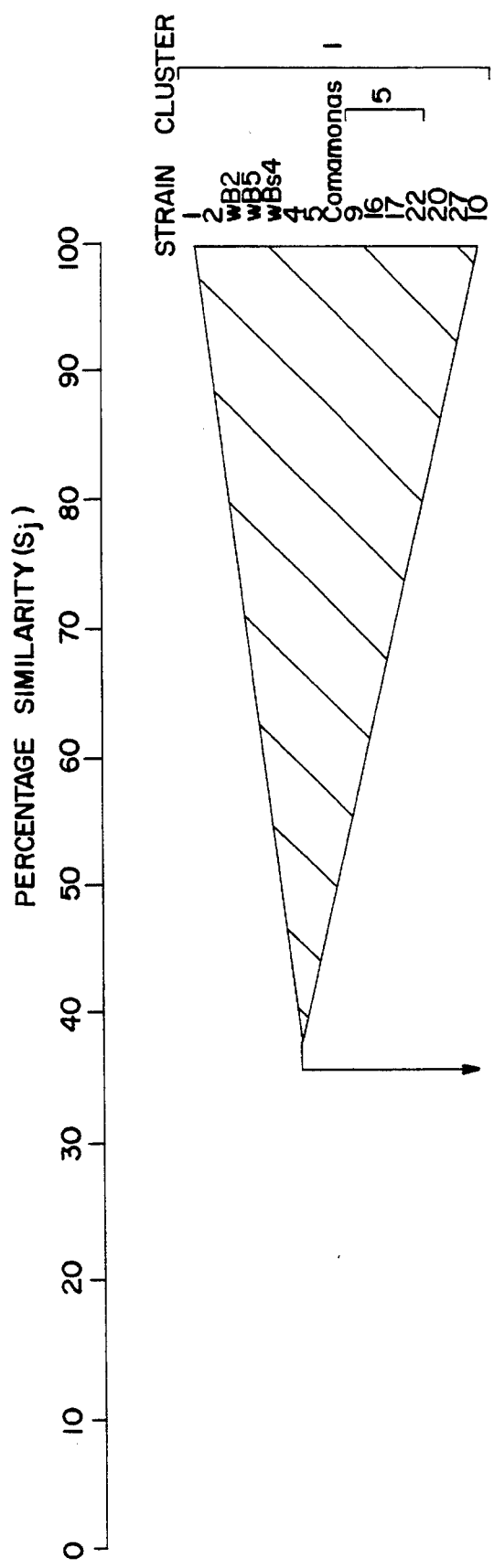
FIG. 2. (Sheet 1, Sheet 2 and Sheet 3) Simplified dendrogram showing different clusters (phenons), Sheet 1 Sheet 2 and Sheet 3, obtained with the $S_J$ coefficient and Unweighted Average Linkage procedure.
Figure 2B:
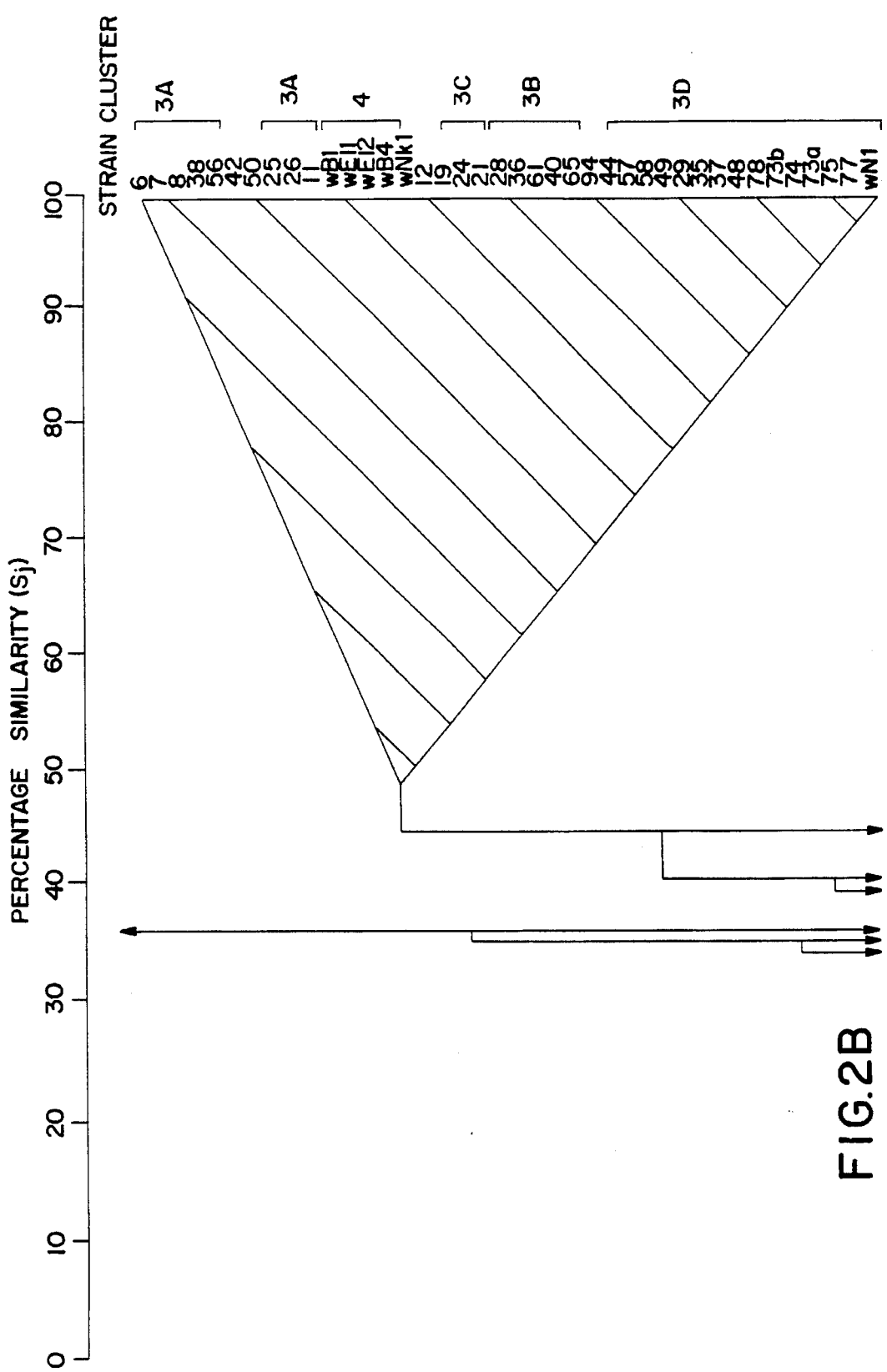
Figure 2C:
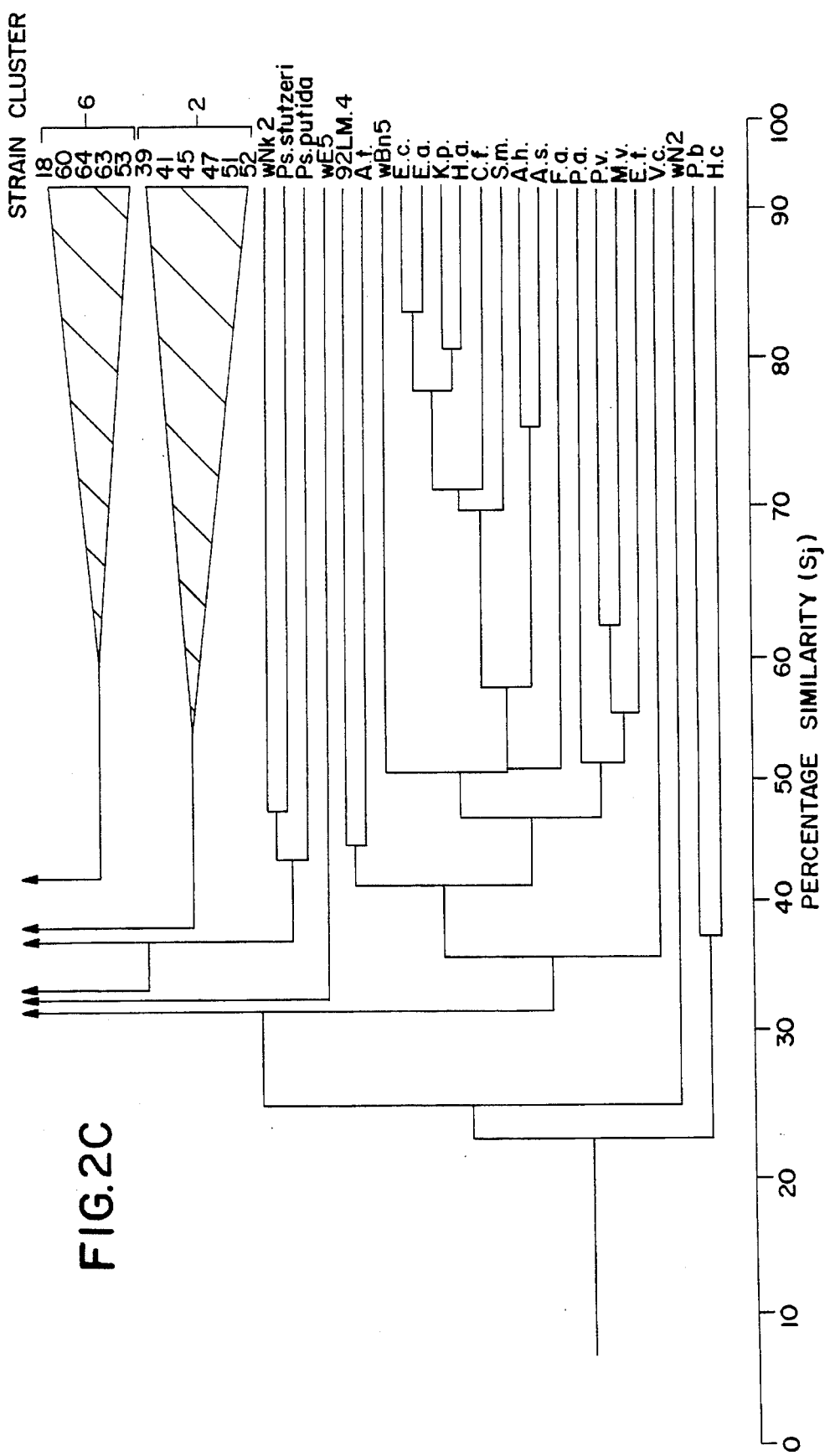

* abbreviation used in FIG. 1 and FIG. 2
$^T$denotes "Type Strain"
$^{NT}$denotes "Neotype Strain"

Analysis of Test Data

The Estimation of Taxonomic Resemblance

The phenetic data, consisting of 104 unit characters were scored as indicated in Appendix C, and set out in the form of an "n x t" matrix, whose t columns represent the t bacterial strains to be grouped on the basis of resemblances, and whose n rows are the unit characters. Taxonomic resemblance of the bacterial strains was estimated by means of a similarity coefficient (Sneath, P. H. A. and Sokal, R. R., *Numerical Taxonomy*, supra, pp. 114–187). Although many different coefficients have been used for biological classification, only a few have found regular use in bacteriology. We have chosen to apply two association coefficients (Sneath, P. H. A. and Sokal, R. R., ibid, p. 129 et seq.), namely, the Gower and Jaccard coefficients. These have been frequently applied to the analysis of bacteriological data and have a wide acceptance by those skilled in the art since they have been shown to result in robust classifications.

The coded data were analyzed using the TAXPAK program package (Sackin, M. J., "Programmes for classification and identification". In *Methods in Microbiology, Volume 19* (eds. R. R. Colwell and R. Grigorova), pp. 459–494, Academic Press, London, (1987)) run on a DEC VAX computer at the University of Leicester, U.K.

A similarity matrix was constructed for all pairs of strains using the Gower Coefficient ($S_G$) with the option of permitting negative matches (Sneath, P. H. A. and Sokal, R. R., supra, pp. 135–136) using the RTBNSIM program in TAXPAK. As the primary instrument of analysis and the one upon which most of the arguments presented herein are based, the Gower Coefficient was chosen over other coefficients for generating similarity matrices because it is applicable to all types of characters or data, namely, two-state, multistate (ordered and qualitative), and quantitative.

Cluster analysis of the similarity matrix was accomplished using the Unweighted Pair Group Method with Arithmetic Averages (UPGMA) algorithm, also known as the Unweighted Average Linkage procedure, by running the SMATCLST sub-routine in TAXPAK.

The result of the cluster analysis is a dendrogram, a simplified version of which is provided in FIG. 1. The dendrogram illustrates the levels of similarity between the bacterial strains. The dendrogram is obtained by using the DENDGR program in TAXPAK.

The phenetic data, omitting multistate characters (characters 1–5, 11 and 12; Appendix C) and thus consisting of 193 unit characters, and scored in binary notation (positive=1, negative=0) were re-analyzed using the Jaccard Coefficient ($S_j$) (Sneath, P. H. A. and Sokal, R. R., ibid, p. 131) by running the RTBNSIM program in TAXPAK. A further dendrogram was obtained by using the SMATCLST with UPGMA option and DENDGR sub-routines in TAXPAK. A simplified version of this dendrogram is illustrated in FIG. 2. Appendix E gives the percentage positive states of characters in each cluster.

Results of the cluster Analysis $S_G$/UPGMA Method

FIG. 1 shows the results of cluster analysis, based on the Gower Coefficient and the UPGMA method, of 70 new, Gram-negative, alkaliphilic bacteria isolated from in and around alkaline lakes, together with 20 known Gram-negative bacteria.

Six natural clusters or phenons of alkaliphilic bacteria which include 65 of the 70 alkaliphilic strains are generated at the 73% similarity level. Although the choice of 73% for the level of delineation may seem arbitrary, it is in keeping with current practices in numerical taxonomy (Austin, B. and Priest, F., in *Modern Bacterial Taxonomy*, p. 37; Van Nostrand Reinhold; Wokingham, U.K., (1986)). Placing the delineation at a lower percentage would combine groups of clearly unrelated organisms while a higher percentage would produce a multitude of less well-defined clusters. At the 73% level, the individual clusters may represent separate bacterial genera. Furthermore, the significance of clustering at this level is supported by chemotaxonomic data (see below) and the pattern of clusters obtained using the Jaccard Coefficient (FIG. 2).

The significance of the clustering at the 73% level is supported by the results of the TESTDEN program. This program tests the significance of all dichotomous pairs of clusters (comprising 4 or more strains) in a UPGMA generated dendrogram with squared Euclidean distances, or their complement, as a measurement. The program assumes that the clusters are hyperspherical. The critical overlap was set at 0.25%. As can be seen from Table 5, the separation of the clusters is highly significant.

TABLE 5

Significance of the Clusters Generated by the $S_G$/UPGMA Method Provided by TESTDEN

| CLUSTER separates from CLUSTER | | at Significance Level |
|---|---|---|
| 1 | 2 | p = 0.99 |
| 1 + 2 | 3 + 4 | p = 0.99 |
| 1 + 2 + 3 + 4 | 5 + 6 | p < 0.90 |
| 1 + 2 + 3 + 4 + 5 + 6 | controls | p = 0.99 |
| 5 | 6 | p = 0.99 |

A further measure of cluster separation can be estimated from the probability of cluster overlap. This was achieved using the OVERMAT program in TAXPAK with the critical overlap set out at 2.5%. As can be seen from Table 6, there is a greater than 95% probability of less than 2.5% overlap between the clusters. For many of the cluster combinations the overlap is effectively nil. Only Clusters 3 and 4 have a lower probability of <2.5% overlap, but these clusters may be clearly distinguished from one another on the basis of chemotaxonomic data (see below).

TABLE 6

Percentage Probability that Cluster Overlay is <2.5%

| CLUSTER | 1 | 2 | 3 | 4 | 5 | 6 |
|---|---|---|---|---|---|---|
| 1 | | | | | | |
| 2 | 95 | | | | | |
| 3 | 99 | 95 | | | | |
| 4 | 95 | 95 | 90 | | | |
| 5 | 99 | >99 | >99 | >99 | | |
| 6 | >99 | >99 | 99 | >99 | >99 | |

The controls show that, as expected, the cluster analysis groups the Enterobacteriaceae separately. Additionally, the Aeromonas and pseudomonas species, included as controls, also group separately. This is entirely consistent with the current taxonomy of these organisms (*Bergey's Manual of Systematic Bacteriology*, Volume 1, Williams and Wilkins, Baltimore/London, 1984).

Five of the alkaliphilic strains fall outside the major clusters. Two strains, 4E.1 and 5E.1 form a separate but related pair and are obviously associated with the major groups of alkaliphilic bacteria. Strain wN2 is also unclustered but is apparently related to a Pseudomonas species and the major phenons of alkaliphilic bacteria. Strains 92LM.4 and wBn5 do not associate with the major alkaliphilic phenons and probably represent distinct groups of new alkaliphilic bacteria.

Clusters 1 and 2 are the only phenons which show an association with known organisms, i.e. Pseudomonas and Comamonas species. The separation of *Pseudomonas putida* and *Pseudomonas stutzeri* into separate taxa is entirely in keeping with the current taxonomic status of these organisms (Palleroni, N.J. et al, (1973), Int. J. Systematic Bacteriol., 23, 333–339; Gavini, F. et al, (1989), ibid, 39, 135–144; *Bergey's Manual of Systematic Bacteriology*, supra).

It was clear from the original dendrogram that *Pseudomonas stutzeri* is an outlier to Cluster 2 and is not closely related to the other members of the cluster. This is seen when the Euclidean distances of the strains from the centroid of the cluster are computed and used to calculate the cluster radius (Sneath, P. H. A. and Sokal, R. R., supra, pp. 194 et seq). The cluster radius is 3.91 (99% confidence level) and the mean distance of the strains from the centroid is 2.84 (standard deviation 0.46). *Pseudomonas stutzeri* at a distance from the centroid of 3.91 is clearly at the very boundary of phenetic hyperspace which defines Cluster 2.

A clear discrimination between Clusters 1 and 2 is possible using the concept of the minimum discriminatory tests (see below).

Each of the alkaliphilic strains in Cluster 2 have been examined by two independent laboratories expert in the identification of bacteria, namely, the German Culture Collection (DSM, Braunschweig, FRG) and the Laboratory for Microbiology at Delft University of Technology, The Netherlands. Neither of these laboratories was able to make a positive identification of the strains, although both agreed there was a resemblance with Pseudomonas either placing them in RNA homology group I (Palleroni, N.J. et al, supra) or more specifically in the *Comamonas testosteroni/ Pseudomonas alcaligenes* or *Pseudomonas pseudoalcaligenes* groups (Gavini, F. et al, supra). However, no Pseudomonas species are known which are able to grow under the same highly alkaline conditions (pH 10) as the new strains described herein. An attempt was made to cultivate *Pseudomonas pseudoalcaligenes$^T$* DSM 50188 and *Pseudomonas alcaligenes$^T$* DSM 50342 in an alkaline broth medium (Medium A, Appendix A), but without success.

The results of these experts together with the discoveries described here, clearly indicate that these alkaliphilic strains in Clusters 1 and 2 represent new species of bacteria.

Clusters 3, 4, 5 and 6 are discrete phenons distinguished from each other on the basis of the minimum discriminatory tests (see below) and chemotaxonomic markers (see below). These phenons show no significant similarity with known groups of bacteria, and thus represent new genera or species.

Whole cell protein patterns generated by PAGE-electrophoresis indicate that a number of strains are likely to be identical. Examples include: 1E-1$^{CT}$ and 2E.1; 6B.1, 7B.1 and 8B.1; 45E.3$^{CT}$ and 47E.3. The dendrogram reveals that these strains are related at an average $S_G$ value of 92.3%, indicating a probable test error of 3.8% (Sneath, P. H. A. and Sokal, R. R., supra). Strains 73bC.4 and 74C.4, which appear to be closely related (90% $S_G$), have similar but not to be closely related identical gel patterns.

$S_J$/UPGMA Method

The Jaccard coefficient is a useful adjunct to the Gower coefficient as it can be used to detect phenons in the latter generated by negative matches or distortions owing to undue weight being put on potentially subjective qualitative data. Consequently, the Jaccard coefficient is useful for confirming the validity of clusters defined initially by the use of the Gower coefficient. The Jaccard coefficient is particularly useful in comparing biochemically unreactive organisms (Austin, B., and Priest, F. G., supra, p. 37).

In the main, all of the clusters generated by the $S_G$/UPGMA method are recovered in the dendrogram produced by the $S_J$/UPGMA method (FIG. 2). Although the composition of the clusters is virtually identical in both dendrograms, a few strains have changed position. Non-clustering strains 4E.1 and 5E.1 move into Cluster 1/5, strains 42E.3 and 50N.3 move from Cluster 2 to Cluster 3/4. The strains wNk2, *Pseudomonas stutzeri*, *Pseudomonas putida*, wE5 become non-clustering.

Not surprisingly, the $S_4$ transformation combines ($S_G$) Clusters 1 and 5. Both of these clusters are characterized as consisting of biochemically fairly unreactive strains. However, Clusters 1 and 5 are clearly distinct. Cluster 1 consists of strains producing cream/beige, circular colonies while the strains of Cluster 5 exclusively produce bright yellow, irregular colonies.

Furthermore, the $S_J$ transformation groups most of the strains of Cluster 4 with the strains of Cluster 3. However, it is evident from the chemotaxonomic data (see below), which shows that the strains of Cluster 4 contain Q9 and the strains of Cluster 3 contain mainly Q6, that these clusters should not be combined since they contain distinctly different strains. For these reasons, it is considered that the clustering produced by the $S_G$/UPGMA method is the better representation of the actual taxonomic status of these strains. However, the $S_J$/UPGMA serves to re-emphasize that with the single exception of a Comamonas species none of the known strains, not even the Pseudomonas control strains, bear significant resemblance to the clusters of the new alkaliphilic bacteria.

Chemotaxonomic Definition of the Clusters

Chemotaxonomy is the study of the chemical compositions of organisms in relation to their systematics. The analysis of chromosomal DNA, ribosomal RNA, proteins, cell walls and membranes, for example, can give valuable insights into taxonomic relationships and may be used as a further tool to construct or to verify the taxonomies of microorganisms (Goodfellow, M. and Minnikin, D .E. in *Chemical Methods in Bacterial Systematics*, (eds. Goodfellow, M. and Minnikin, D. E.), Academic Press, London and Orlando, Fla., (1985), pp. 1–5). However, it is not always possible to decide a priori which type of chemical information will be most diagnostic for a given classification. The amphipathic polar lipids, the major respiratory quinones, fatty acids located in the bacterial membranes and analysis of chromosomal DNA all have taxonomic significance for the classification of various bacteria (Lechevalier, H. and Lechevalier, M. P., in *Microbial Lipids*, volume 1 (eds. Ratledge, C. and Wilkinson, S. G.) Academic Press, London and San Diego, Calif., (1988), pp. 869– 902).

Polar Lipids

The extraction of polar lipids from bacteria and their analysis by two dimensional thin layer chromatography (2D-TLC) may yield patterns of diagnostic value. Stationary phase cells were extracted in 1:1 (v/v) CHCl$_3$: CH$_3$OH and examined by 2D-TLC as described by Ross, H. N. H., Grant, W. D. and Harris, J. E., in *Chemical Methods in Bacterial Systematics*, (eds. Goodfellow, M. and Minnikin, D. E.), Academic Press, London and Orlando, Fla. (1985), pp.

289–300. The types of lipids present on the chromatograms were visualized using a variety of differential stains (Ross, H. N. M., et al., supra, p. 291; and Trincone, A., et al., J. Gen. Microbiol., (1990), 136, pp. 2327–2331). The identity of components were confirmed by co-chromatography with known lipids.

The results of this analysis for representative strains of Gram-negative alkaliphiles are set out in Table 7. These show no clear polar lipid pattern which is distinct for any one cluster. All strains contain phosphatidylglycerol, diphosphatidylglycerol, phosphatidylglycerol phosphate and phosphatidylethanolamine. In addition, certain strains, particularly in Cluster 3, contain phosphatidylglycerol sulphate (PGS). The distribution of PGS within Cluster 3 coincides broadly with the suspected sub-group structure of the cluster evident from the phenetic and other chemotaxonamic data. PGS is therefore a non-exclusive marker for Cluster 3.

We were surprised to find that a majority of the bacteria contained a glycolipid which on the basis of numerous co-chromatographic analyses appeared common to Gram-negative bacteria of the present invention. Glycolipids have not previously been demonstrated to be present in alkaliphilic bacteria (Krulwich, T. A., et al, CRC Critical Reviews in Microbiology, (1988), 16, 15–36). Furthermore, as judged by co-chromatography of lipids obtained from several strains, the glycolipid is also found in Gram-positive alkaliphiles isolated from soda lakes. It is possible therefore, that the chemical structure of the glycolipid may be a chemotaxonomic marker for the obligate alkaliphiles.

TABLE 7

Polar Lipid Components of Gram-Negative Alkaliphilic Bacteria

| CLUSTER | STRAIN | PG | DPG | PGP | PE | PGS | GL | AL | UPL |
|---|---|---|---|---|---|---|---|---|---|
| 1 | 1E.1[CT] | + | + | + | + | | | | |
| | 2E.1 | + | + | + | + | + | | | |
| | 10B.1 | + | + | + | + | | 3+ | | |
| | 20N.1 | + | + | + | + | + | | | |
| | 27M.1 | + | + | | + | + | | | |
| | wNk.2 | + | + | + | + | | | | + |
| 2 | 39E.3 | + | + | + | + | | + | | |
| | 41E.3 | + | + | + | + | | + | | |
| | 45E.3[CT] | + | + | + | + | | + | | |
| | 51N.3 | + | + | + | + | | + | | |
| | 52N.3 | + | + | + | + | | + | | |
| | 42E.3 | + | + | + | + | | + | | |
| | 50N.3 | + | + | + | + | + | | | |
| | P.s. | + | + | | + | | | | |
| — | 5E.1 | + | + | + | + | + | + | | + |
| 3 | 6B.1 | + | + | + | + | | | + | |
| | 7B.1 | + | + | + | + | | + | | |
| | 8B.1 | + | + | + | + | | + | | |
| | 25B.1 | + | + | + | + | | + | | |
| | 26N.1 | + | + | + | + | | + | | |
| | 12C.1 | + | + | + | + | | + | + | |
| | 28N.1[CT] | + | + | + | + | + | | | |
| | 36E.2 | + | + | + | + | + | + | | |
| | 40E.3 | + | + | + | + | + | + | | |
| | 94LM.4 | + | + | + | + | + | + | | |
| | 19N.1 | + | + | + | + | | + | | |
| | 24B.1 | + | + | + | + | | + | | |
| | 21M.1 | + | + | + | + | | + | | |
| | 29C.1 | + | + | + | + | + | | | |
| | 35E.2 | + | + | + | + | + | | | |
| | 37E.2 | + | + | + | + | + | + | | |
| | 48E.3 | + | + | + | + | + | + | | |
| | 73aC.4 | + | + | + | + | + | + | | |
| | 74C.4 | + | + | + | + | + | + | | |
| | 49E.3 | + | + | + | + | + | + | | |
| | 44E.3 | + | + | + | + | + | + | | |
| | 58E.4 | + | + | + | + | | + | | |
| 4 | wE5 | + | + | + | + | + | | | |
| | wB4[CT] | + | + | + | + | | | | |
| | wNk1 | + | + | + | + | | | + | + |
| | wE11 | + | + | + | + | | | + | + |
| | wE12 | + | + | + | + | | | | + |
| 5 | 9B.1 | + | + | + | + | | | | |
| | 16N.1 | + | + | + | + | | | | |
| | 17N.1[CT] | + | + | + | + | | + | | |
| | 22M.1 | + | + | + | + | | | | |
| 6 | 18N.1 | + | + | + | + | + | | | |
| | 59E.4 | + | + | + | + | | | | |
| | 64B.4[CT] | + | + | + | + | | | | |
| | 63N.4 | + | + | + | + | | + | | |
| | 53E.4 | + | + | + | + | + | | | |

(PG) phosphatidylglycerol;
(DPG) diphosphatidylglycerol;
(PGP) phosphatidylglycerol phosphate;
(PE) phosphatidylethanolamine;

TABLE 7-continued

Polar Lipid Components of Gram-Negative Alkaliphilic Bacteria

| CLUSTER | STRAIN | PG | DPG | PGP | PE | PGS | GL | AL | UPL |
|---------|--------|----|----|-----|----|----|----|----|-----|

(PGS) phosphatidylglycerol sulphate;
(GL) unidentified glycolipid(s), a-naphthol positive (the number in the column gives the number of positive spots on the TLC plate);
(AL) unidentified amino-lipid (ninhydrin positive);
(UPL) unidentified phospho-lipid(s).

Isoprenoid Quinones

The isoprenoid or respiratory quinones are characteristic components of the plasma membrane of aerobic bacteria. There are two types; menaquinones and ubiquinones. The value of isoprenoid quinones as taxonomic criteria lies in the variation in the length of the polyprenyl side-chain and the degree of saturation (Collins, M. D. and Jones, D. (1981), supra). Freeze dried stationary phase bacterial cells were extracted, using a modified procedure of Collins, M. D. (in *Chemical Methods in Bacterial Systematics*, supra, pp. 267–284), in 1:1 (v/v) $CHCl_3:CH_3OH$ at 50° C., for 16 hours. The quinones were examined by reverse phase thin layer chromatography as described by Collins, M. D. (supra).

The results of quinone analyses of nearly all the strains of Gram-negative alkaliphiles are illustrated in Table 8. All of the strains tested contained exclusively ubiquinones which confirms their status as Gram-negative bacteria (Collins, M. D. and Jones, D., supra). Table 8 shows quite clearly that the major ubiquinones are Q6 and Q9. It is also evident that the strains containing Q6 are exclusive to cluster 3 and that this distinguishes Cluster 3 from all the other clusters since they contain strains possessing Q9 as the major ubiquinone.

TABLE 8

Major Respiratory Quinones of the Strains Arranged per Cluster

| CLUSTER 1 | | CLUSTER 2 | | CLUSTER 3 | |
|-----------|---|-----------|---|-----------|---|
| STRAIN | Q | STRAIN | Q | STRAIN | Q |
| 1E.1$^{CT}$ | Q9 | 39E.3 | Q9 | 6B.1 | Q6 |
| 2E.1 | Q9 | 41E.3 | Q9 | 7B.1 | Q6, Q9 |
| wB2 | Q9 | 45E.3$^{CT}$ | Q9 | 8B.1 | Q6, Q9 |
| wB5 | Q9 | 47E.3 | Q9, Q10 | 38E.2 | Q6 |
| wBs4 | Q9 | 52N.3 | Q9 | 56E.4 | Q6 |
| 10B.1 | Q9 | 42E.3 | Q9 | 25B.1 | Q6, Q9 |
| 20N.1 | Q9 | 50N.3 | Q9 | 26N.1 | Q6 |
| 27M.1 | Q9 | | | 12C.1 | Q6 |
| C.t.* | [Q8 + Q9(t)] | | | 28N.1$^{CT}$ | Q6 |
| wNk2 | Q9 | | | 61N.4 | Q6 |
| P.p.* | [Q9] | | | 36E.2 | Q6 |
| | | | | 40E.3 | Q6, Q9 |
| | | | | 65B.4 | Q6 |
| | | | | 94LM.4 | Q6, Q9 |
| | | | | 19N.1 | Q6, Q9 |
| | | | | 24B.1 | Q6, Q9 |
| | | | | 21M.1 | Q6 |
| | | | | 29C.1 | Q6 |
| | | | | 35E.2 | Q6 |
| | | | | 37E.2 | Q6 |
| | | | | 48E.3 | Q6 |
| | | | | 78LN.4 | Q6 |
| | | | | 73aC.4 | Q6 |
| | | | | 75C.4 | Q6 |
| | | | | 73bC.4 | Q6 |
| | | | | 74C.4 | Q6, Q9 |
| | | | | 77LN.4 | Q6 |
| | | | | 49E.3 | Q6 |
| | | | | 58E.4 | Q6 |
| | | | | 57E.4 | Q6 |

| CLUSTER 4 | | CLUSTER 5 | | CLUSTER 6 | | NON-CLUSTER | |
|-----------|---|-----------|---|-----------|---|-------------|---|
| STRAIN | Q | STRAIN | Q | STRAIN | Q | STRAIN | Q |
| wE5 | Q9 | 9B.1 | Q9 | 18N.1 | Q9 | wN.2 | Q9 |
| wB4$^{CT}$ | Q9 | 16N.1 | Q9 | 59E.4 | Q9 | 5E.1 | Q8 |
| wNk1 | Q9 | 17N.1$^{CT}$ | Q9, Q10 | 64B.4$^{CT}$ | Q9 | 92LM.4 | Q9 |
| wE11 | Q9, Q10(t) | 22M.1 | Q9 | 63N.4 | Q9 | wBn5 | Q8, Q9(t) |
| wE12 | Q9 | 22M.1 | Q9 | 53E.4 | Q9 | | |

Q = Ubiquinone, the number indicates the number of side-chain isoprene units.
(t) = trace TABLE 8-continued Major Respiratory Quinones of the Strains Arranged per Cluster C.t. = *Comamonas terrigena*[T] NCIMB 8193; the quinone result is obtained from J. Tamaoka et al, International Journal of Systematic Bacteriology, 37, 52–59, (1987).
P.p. = *Pseudomonas putida*[T] NCIMB 9494, the quinone result is obtained from M. D. Collins and D. Jones, Microbiological Reviews, 45, 316–354, (1981).

Fatty Acids

The analysis of fatty acid profiles has had a significant impact on bacterial classification especially in the circumscription of genera and species among Gram-positive bacteria and actinomycetes (Kroppenstedt, R. M., in *Chemical Methods in Bacterial Systematics* (eds. M. Goodfellow and D. E. Minnikin), Academic Press; London and Orlando, Fla., (1985), pp. 173–199); Lechevalier, H. and Lechevalier, M. P., supra.

Freeze dried stationary phase cells (200–300 mg) were extracted for 16 hours at 75° C. in toluene:methanol:conc. sulphuric acid (2.5 ml:2.5 ml:0.2 ml) and after cooling, the lipids were partitioned into hexane (twice times 1 ml). Residual acid was removed using $NH_4HCO_3$. Lipid extracts were concentrated under $O_2$-free $N_2$, dissolved in 300 μl hexane and applied to preparative silica gel plates (Merck F254, Type T). The plates were developed in hexane: diethyl ether 85:15 (v/v) and the fatty acid methyl esters scraped off, extracted with hexane and concentrated under a stream of $O_2$-free $N_2$.

The fatty acid methyl esters were dissolved in heptane and analyzed by gas chromatography using a Packard model 439 chromatograph equipped with flame ionization detectors. The samples were divided by a sample splitter and analyzed simultaneously over two columns, namely, CP-SIL-88 (Chrompack) (length 50 meter, internal diameter 0.22 mm) and Ultra-2 (Hewlett/Packard) (length 50 m, internal diameter 0.20 mm). The carrier gas was nitrogen; the injection temperature 120° C.; temperature gradient 2.5° C. per minute to 240° C. and isothermal at 240° C. for 30 minutes. Fatty acid methyl esters were assigned by reference to known standard mixtures. The identity of some peaks was confirmed by means of gas chromatography/mass spectrometry using a Carlo Erba HRGC 5160 Mega series gas chromatograph equipped with a CP-SIL-88 column (length 50 meter, internal diameter 0.22 mm) with helium as carrier gas and direct injection into the source of a AMD 403 mass spectrometer.

The fatty acid compositions of representative individual Gram-negative bacteria are set out in Table 9. Table 10 shows the unique fatty acid profiles of each of the clusters. Clusters 1, 2, 3 and 4 are fairly typical of the majority of Gram-negative bacteria where the major saturated fatty acid is C16:0 with lesser amounts of C14:0 and C18:0. The major unsaturated fatty acids in these alkaliphilic bacteria are C16:0 and C18:1 (11-cis), which is also typical, as is the lack of odd-numbered fatty acids (Wilkinson, S. G., in *Microbial Lipids*, volume 1 (eds. Ratledge, C. and Wilkinson, S. G.), Academic Press, London and San Diego, Calif., (1988), pp. 299–488). Minor amounts of C17:0 and C19:0 cyclopropane acids are found in some strains of Gram-negative bacteria. The strains of Cluster 3 exhibit fairly simple fatty acid profiles with C16:0 and C18:1 contributing 67–88% of the total acids, and C16:1 plus C18:0 up to 20% of the remainder. Even so, the fatty acid patterns support the notion that Cluster 3 contains several sub-groups, a conclusion that is also inferred from phenetic (numerical taxonomy) and polar lipid analyses (Table 7).

The strains of Cluster 1 can be distinguished from those of Cluster 2 on the relative abundance of straight chain saturated and unsaturated fatty acids, as well as the percentage amounts of C18:1(11-cis). The alkaliphilic bacteria of Clusters 1 and 2 have more complex fatty acid profiles than those of Cluster 3, with many more minor components. From the numerical taxonomy evidence, the alkaliphilic strains of Clusters 1 and 2 exhibit some resemblance to Pseudomonas species. However, the total lack of any hydroxy-fatty acids which are typical of most Pseudomonas species, further indicating that a close relationship is doubtful.

The strains of Clusters 5 and 6 are remarkable in that besides containing major amounts of C16:0, the other major fatty acids are odd-numbered branched chain acids (40–85%). Also, these strains lack significant amounts of C18:1 or any other unsaturated acids which are present in appreciable amounts in the alkaliphilic strains of Clusters 1, 2, 3 and 4. The presence of large amounts of C15:0 and C17:0 iso and anteiso acids is characteristic of only a very few classes of Gram-negative bacteria, notably species from exotic environments such as Thermus, or poorly defined taxa such as Flavobacterium (Wilkinson, S. G., supra). This result further emphasizes the novelty of the alkaliphilic strains of the present invention. The strains of Clusters 5 and 6 can be distinguished from each other by the proportion of branched-chain fatty acids they contain and more especially by the relative proportions of even- and odd-numbered fatty acids.

TABLE 9

Fatty Acid Composition[+] of Gram-Negative Alkaliphiles

| | CLUSTER | | | | | | | | | | | | | | non-clustering | |
|---|---|---|---|---|---|---|---|---|---|---|---|---|---|---|---|---|
| | 1 | | 2 | | 3 | | | | | 4 | | 5 | | | 6 | | | |
| FATTY ACID | 1E.1[CT] | 2E.1 | 45E.3[CT] | 50E.3 | 25B.1 | 28N.1[CT] | 24B.1 | 37E.2 | 48E.3 | WB4[CT] | WEI1 | 9B.1 | 16N.1 | 17N.1[CT] | 59E.4 | 64B.4[CT] | 5E.1 | 92LM.4 |
| 10:0 | | | | | | 0.4 | | | | 0.5 | 0.2 | | | | | | | |
| 12:0 | | t | | | | 0.5 | 0.5 | 0.3 | t | 0.9 | 0.8 | | | | | | | |
| 12:1 | 0.2 | 0.3 | | | | | | | | | | | | | | | | |
| 13:0 | | | | | | | | | | | | | | | | | | |
| 14:0 iso | 0.7 | 0.7 | 3.6 | 4.7 | 4.5 | 4.4 | 3.4 | 2.9 | 2.6 | 3.8 | 1.3 | 3.2 | 1.9 | 1.2 | 3.9 | 6.4 | 3.8 | 1.5 |
| 14:0 | 2.6 | | <0.1 | | | 0.1 | | | t | | | 0.7 | t | t | 0.7 | 2.0 | | |
| 14:1 | | 0.9 | | | | | | | | | ).1 | | | | | | | |
| 15:0 | | 0.3 | 3.8 | 3.9 | 0.7 | 0.6 | | 0.9 | 0.3 | 0.7 | 0.2 | | | | | | | |
| 15:0 iso | | | 0.6 | 0.9 | | | | | | <0.1 | | | | | | | | |
| 15:0 anteiso | | | 0.1 | 0.2 | | | | | | | | 8.7 | 9.3 | 8.2 | t | 3.8 | t | 9.9 |
| 15:0 cyclo | | | <0.1 | 0.3 | | | | | | 26.8 | 26.9 | 32.2 | 27.1 | 35.3 | 24.8 | 18.1 | | |
| 16:0 | 29.0 | 32.0 | 28.5 | 34.4 | 37.3 | 24.1 | 36.7 | 33.3 | 26.0 | | | 22.5 | 17.4 | 12.5 | 26.3 | 40.5 | 74.7 | 18.7 |
| 16:0 iso | | 0.3 | | 0.2 | | | | | | | | | | | | | | 2.1 |
| 16:1 | 7.4 | 9.6 | 4.1 | 4.3 | 11.6 | 15.0 | 5.8 | 3.4 | 8.0 | 7.9 | 2.4 | 4.7 | 5.8 | 6.7 | 2.4 | 3.7 | 2.9 | |
| 17:0 | 0.5 | 2.3 | 0.9 | 1.1 | | 0.2 | | 1.2 | 0.3 | 0.4 | 0.3 | | | | t | 2.4 | | |
| 17:0 iso | | | 0.2 | 0.6 | | | | | | 0.4 | 0.3 | | | | 0.6 | 1.7 | | 15.7 |
| 17:0 anteiso | | | | | | | | | | | | | | | 6.1 | 3.7 | | 6.8 |
| 17:0 cyclo | 0.3 | | 0.4[a] | 1.8 | | | | 1.8 | 0.3 | 0.2 | | 21.9 | 24.4 | 29.8 | | | | |
| 17:1 | | 1.6 | | | 0.6 | | | | | <0.1 | | | | | | | | |
| 17:1 br | | | | 1.7 | | | | | | | | | | | | | | |
| 18:0 | 12.0 | 4.7 | 17.9 | 10.8 | 8.9 | 0.2 | 2.0 | 0.6 | 1.1 | 5.2 | 3.5 | 2.3 | 5.3 | 1.2 | 16.2 | 4.8 | 2.6 | 1.5 |
| 18:0 unknown | 0.2 | 0.4 | | | | | | | | | | | | | | | 5.9 | |
| 18:1 9-cis | 0.2 | t | 0.5 | 0.3 | | t | t | 0.6 | t | t | 2.5 | *0.5 | *1.6 | *1.0 | *5.7 | *0.5 | *10.0 | |
| 18:1 9-trans | 0.5 | 0.6 | 5.9 | 2.9 | 2.4 | 0.2 | 1.0 | 0.6 | 0.6 | 1.7 | 0.9 | | | | | | | |
| 18:1 11-cis | 42.0 | 44.0 | 23.9 | 24.1 | 27.5 | 54.2 | 50.6 | 41.6 | 57.7 | 47.4 | 48.1 | | | | | | | |
| 18:1 unknown | 0.2 | 0.3 | | | | | | | | | | | | | | | | |
| 18:2 | | | 0.5 | 1.9 | 2.7 | | 0.5 | t | t | 1.0 | 0.3 | | | | 2.7 | | | |
| 19:0 | | | 0.1 | | | | | | | | | | | | | | | |
| 19:0 cyclo | | | | 1.3 | | 0.4 | | 12.9 | 2.0 | 1.0 | 11.2 | | | | | | | |
| 19:1 br | | | | | | | | | | | 0.4 | | | | | | | |
| 20:0 | 0.4 | | 5.3 | 2.7 | 2.4 | | | | | 1.3 | 0.3 | | | | 4.6 | | | |
| 20:1 | 3.6 | 1.2 | | | | | | | | | | | | | | | | |
| 22:0 | | | 3.3 | 1.5 | 1.4 | | | | | 0.8 | 0.2 | | | | 0.8 | 0.2 | | |
| 24:0 | | | 0.2 | | | | | | | | | | | | | | | |

*= includes all C18:1 isomers
+ % total fatty acids
t = trace
br = branched
a = C17:0 cyclo or C18:0 unknown

TABLE 10

Fatty Acid Profiles of the Clusters of Gram-Negative Alkaliphiles

| | Cluster | | | | | | | |
|---|---|---|---|---|---|---|---|---|
| | 1 | 2 | 3A/B | 3C | 3D | 4 | 5 | 6 |
| Predominant Fatty Acids (>10%) | C16:0 C18:1 11-cis | C16:0 C18:0 C18:1 11-cis | C16:0 C16:1 C18:1 11-cis | C16:0 C18:1 11-cis | C16:0 C18:1 11-cis | C16:0 C18:1 11-cis | C15:0 anteiso C16:0 C17:0 anteiso | C15:0 br C16:0 |
| n-saturated | ~40% | 60–65% | 30–55% | ~40% | 30–40% | 30–40% | 15–30% | 55–60% |
| n-unsaturated | ~60% | ≈33% | 45–70% | ~40% | 50–65% | 50–60% | < 2% | <10% |
| iso | < 1% | < 1% | 0% | 0% | 0% | < 1% | ~20% | 10–20% |
| anteiso | 0% | < 1% | 0% | 0% | 0% | < 1% | ~20% | 10–20% |
| total branched | < 1% | < 3% | 0% | 0% | 0% | 1–12% | >70% | ~40% |
| cyclo | 0% | < 5% | | 0% | 2–15% | < 2% | 0% | 0% |
| even carbon no. | >95% | >90% | >99% | >99% | >80% | >85% | 20–35% | 55–65% |
| odd carbon no. | < 5% | <10% | < 1% | < 1% | <20% | <15% | 65–80% | 35–45% |
| additional markers | | C17:0 cyclo C19:0 cyclo C17:1 br | | | C17:0 cyclo C19:0 cyclo | | | | br = branched

Nucleic Acids

An essential component of any taxonomic study is an analysis of the genetic material—the nucleic acids. The composition of chromosomal DNA is unaffected by the growth conditions of the organism and an appropriate analysis may confirm or refute the taxonomic position of the organism. Chromosomal DNA may be analyzed by the determination of the base composition (G+C mol %) of individual strains, and the base sequence homologies between pairs of strains by DNA-DNA reassociation (hybridization) (Owen, R. J. and Pitcher, D., in *Chemical Methods in Bacterial Systematics* (eds. M. Goodfellow and D. E. Minnikin), Academic Press, London and Orlando, Fla. (1985), pp. 67–93).

DNA Base Composition

The guanine plus cytosine (G+C mol %) composition is constant for the chromosomal DNA from any given organism. Closely related organisms have similar G+C compositions. However, G+C results must be interpreted within the context of independent taxonomic data since similar G+C mol % of DNA samples from different organisms does not in itself imply biological relatedness.

DNA was extracted from cells grown to exponential phase in Medium A by the chloroform:phenol method and was precipitated with ethanol. Base composition was determined by the thermal denaturation method (Marmur, J. and Doty, P. (1962), J. Mol. Biol., 3, 585–594) on a Phillips model PV8764 spectrophotometer with temperature programming. A second method involved HPLC analysis on a Beckman system gold using a Beckman ultrasphere ODS column and 0.04M potassium dihydrogen phosphate plus acetonitrile (9+1, v/v) as eluent at a flow rate of 1.5 ml/min, after treatment of the DNA with nuclease P1 and alkaline phosphatase.

The results of these analyses are set out in Table 11. The G+C mol % values for the alkaliphilic bacteria cover a range of 30 mol % (37.6–67.1 mol %). However, within the clusters the variation is only 3–7 mol %, which further confirms that the strains within a cluster are closely related to each other.

TABLE 11

DNA Base Composition of Gram-Negative Alkaliphilic Bacteria

| | | G + C mol % | |
|---|---|---|---|
| Cluster | Strain | HPLC | $T_M$ |
| 1 | 2E.1 | 55.2 | |
| | wBs4 | | 51.2 |
| | 20N.1 | 51.1 | |
| | wNk2 | | 53.0 |
| 2 | 42E.2 | 62.7 | |
| 3 | wB1 | | 63.0 |
| | 28N.1$^{CT}$ | 64.1 | |
| | 37E.2 | 67.1 | |
| | wN1 | | 64.8 |
| 4 | wE5 | | 58.5 |
| | WB4$^{CT}$ | | 65.3 |
| | wNk1 | | 61.0 |
| | wEl1 | | 59.7 |
| | wEl2 | | 58.1 |
| 5 | 17N.1$^{CT}$ | 50.0 | |
| | 22M.1 | 43.8 | |
| 6 | 64B.4$^{CT}$ | 41.0 | |
| | 53E.4 | 37.6 | |
| non | wN2 | | 64.1 |
| | wBn5 | | 54.6 |

DNA-DNA Molecular Hybridization

The method used was essentially that of Crosa, J. H. et al. (Int. J. Systematic Bacteriol., 29, 328–332, 1979). Tritium labelled DNA was prepared using a nick-translation kit (Amersham, N5000) according to the manufacturer's instructions. The reassociation mixtures were incubated at 65° C. for 16 hours. The results are set out in Table 12 from which it can be seen that the DNA sequence homology is higher within the clusters that between the clusters.

TABLE 12

Inter-Cluster and Intra-Cluster DNA-DNA Homology Values for Gram-Negative Alkaliphilic Bacteria

| Cluster | Strain | Cluster 1 (2E.1) | Cluster 2 (45E.3$^{CT}$) | Cluster 3 (28N.1$^{CT}$) | Cluster 4 | Cluster 5 (17N.1$^{CT}$) | Cluster 6 (64B.4$^{CT}$) |
|---|---|---|---|---|---|---|---|
| 1 | 2E.1 | 100 | | 33 | 35 | 25 | 25 |
|   | 20N.1 | 56 | | | | | |
| 2 | 45E.3$^{CT}$ | | 100 | | 25 | | |
|   | 42E.3 | | 76 | | | 30 | |
| 3 | 28N.1$^{CT}$ | 20 | 34 | 100 | 26 | 30 | 30 |
|   | 56E.4 | | | 51 | | | |
|   | 21M.1 | | | | | 53 | |
|   | 37E.2 | | 37 | | | | |
|   | 44E.3 | | | 55 | | | |
| 4 | wE12 | | | | 100 | | |
|   | wB4$^{CT}$ | | | 41 | 43 | | |
| 5 | 17N.1$^{CT}$ | 45 | 44 | 36 | 24 | 100 | 44 |
|   | 22M.1 | | | | | 65 | |
| 6 | 64B.4$^{CT}$ | 21 | 31 | 35 | 25 | 34 | 100 |
|   | 53E.4 | | | | | | 60 |
|   | SS | 17 | | | | 20 | 20 |

The values give the percent hybridization between the strains (rows) and 10-labelled strains (columns).
SS = salmon sperm DNA.

Determination of Representative Strains

The centroid of each individual cluster generated by the $S_G$/UPGMA method was computed using the RGROUPS program in TAXPAK. The centroid of a Cluster of points representing real organisms projected into hyperspace represents a hypothetical average organism. The centroid rarely, if ever represents a real organism. Therefore, the Euclidean distances of each of the members of the cluster from the centroid of the cluster were calculated in order to establish which strain was closest to the hypothetical average organism. The strain closest to the centroid was designated the "centrotype" organism (indicated with the superscript "CT").

The centrotype organism can be thought of as the "Type Strain" which most closely represents the essential and discriminating features of each particular cluster. The centrotype strains are recorded in Table 13.

TABLE 13

Centrotype Strains

| Cluster Number | Number of Strains in Cluster | Mean Euclidean Distance of Strains from Centroid | Standard Deviation | Centrotype Strain | Centrotype Euclidean Distance from Centroid |
|---|---|---|---|---|---|
| 1 | 11 | 3.67 | 0.30 | 1E.1 | 2.88 |
| 2 | 9 | 3.20 | 0.52 | 45E.3 | 2.30 |
| 3 | 34 | 3.52 | 0.32 | 28N.1 | 2.90 |
| 4 | 5 | 3.97 | 0.29 | wB4 | 2.87 |
| 5 | 4 | 3.25 | 0.29 | 17N.1 | 2.13 |
| 6 | 5 | 3.11 | 0.41 | 64B.4 | 1.93 |

A description of each of the centrotype organisms has been made so as to be able to distinguish these organisms from all other bacteria previously known and described. In addition, the minimum number of discriminating tests to define each cluster has been computed so that it may be clearly seen that the clusters containing these novel bacteria can be easily distinguished from each other and from all other known bacteria.

Description of Centrotype Strains

Strain 1E.1$^{CT}$(Cluster 1)

An aerobic, motile, Gram-negative rod-shaped bacterium, 1.7–3.3 μm×0.5–0.7 μm.

Obligate alkaliphile, grows best between pH 9 and pH 10.

On alkaline-agar, (Medium A) forms smooth, cream colored colonies, initially translucent but becoming opaque after a few days. The colonies are circular, entire and convex, 2–3 mm in diameter.

In alkaline-broth, (Medium A) growth (37° C.) is flocculent with the formation of a sediment and surface pellicle.

Grows well between 20° C. and 40° C. Grows slowly at 10°–15° C. No growth at 8° C. or 45° C.

| | |
|---|---|
| KOH test: | positive |
| Aminopeptidase: | weak positive |
| Oxidase: | negative |
| Catalase: | positive |
| NaCl tolerance: | 0% to < 8%. No growth at 8% |
| Hydrolysis of Gelatin: | positive |
| Hydrolysis of Starch: | positive |
| Major polar lipid components: | phosphatidylglycerol diphosphatidylglycerol phosphatidylglycerol phosphate phosphatidylethanolamine |
| Major ubiquinone: | Q9 |
| Major fatty acids: | C16:0, C18:0, 11-<u>cis</u> C18:1 |

Chemoorganotroph. Grows on complex substrates such as yeast extract and peptones. Growth on simple sugars and organic acids very restricted (e.g., growth only observed on ribose, sucrose and pyruvate).

Strain 45E.3$^{CT}$ (Cluster 2)

An aerobic, Gram-negative, rod-shaped bacterium, 3–4.5 μm×0.6 μm. Motile by a single polar flagellum.

Obligate alkaliphile growing between pH 7.8 and pH 11.2. On alkaline-agar, (Medium A) forms smooth, opaque, cream colored colonies, 1–2 mm in diameter. The colonies are circular, convex and entire.

In alkaline-broth, (Medium A) growth (37° C.) is slow, slight with an even turbidity, surface pellicle and no sediment.

Grows well between 20° C. and 40° C. Grows slowly at 10° C. No growth at 8° C. or 45° C.

| | |
|---|---|
| KOH test: | positive |
| Aminopeptidase: | positive |
| Oxidase: | positive |
| Catalase: | positive |
| NaCl tolerance: | 0% to 12%. Growth at 12% is slow No growth at 15% |
| Hydrolysis of Gelatin: | positive |
| Hydrolysis of Starch: | positive (weak) |
| Major polar lipid components: | phosphatidylglycerol diphosphatidylglycerol phosphatidylglycerol phosphate phosphatidylethanolamine glycolipid (α-naphthol positive) |
| Major ubiquinone: | Q9 |
| Major fatty acids: | C16:0, C18:0, 11-cis C18:1 |

Chemoorganotroph. Grows on complex substrates such as yeast extract and peptones. No growth on simple sugars. Grows on organic acids (e.g., fumarate, succinate, pyruvate, acetate, lactate) and some fatty acids (e.g., propionate, valerate) and amino acids (e.g., proline, alanine, phenylalanine).

Strain 28N.1$^{CT}$ (Cluster 3)

An aerobic, motile, Gram-negative, rod-shaped bacterium, 4.8–5.5 μm×0.6–0.8 μm. Obligate alkaliphile growing between pH 8.5 and pH 10.7.

On alkaline-agar, (Medium A) forms smooth, circular, opaque colonies with a stringy texture. The colonies have a convex elevation and entire margin. The colony color is initially cream/beige becoming pink after a few days.

In alkaline-broth, (Medium A) growth (37° C.) is heavy, flocculent with a surface pellicle and a sediment.

Grows well between 20° C. and 45° C. Grows slowly at 10° C. and 15° C. No growth at 50° C.

| | |
|---|---|
| KOH test: | positive |
| Aminopeptidase: | positive |
| Oxidase: | positive |
| Catalase: | positive |
| NaCl tolerance: | 0% to 12%. No growth at 15% |
| Hydrolysis of Gelatin: | negative |
| Hydrolysis of Starch: | positive |
| Major polar lipid components: | phosphatidylglycerol diphosphatidylglycerol phosphatidylglycerol phosphate phosphatidylglycerol sulphate phosphatidylethanolamine |
| Major ubiquinone: | Q6 |
| Major fatty acids: | C16:0, C16:1, 11-cis C18:1 |
| G + C: | 64.1 mol % (HPLC) |

Chemoorganotroph. Grows well on complex substrates such as yeast extract and peptones. Grows on simple sugars, organic acids, fatty acids and amino acids.

Strain wB4$^{CT}$ (cluster 4)

An aerobic, Gram-negative, rod-shaped bacterium, 3–4 μm×0.6–0.8 μm, frequently occurring as pairs of cells.

Alkaliphile, grows well between pH 7.5 and pH 10.9.

On alkaline-agar, (Medium A) forms smooth, beige to brown colonies. The colonies are somewhat variable: 1 to >5 mm in size, circular to irregular in form, low convex or raised in elevation with an undulate or entire margin.

In alkaline broth, (Medium A) growth (37° C.) is flocculent, sediment forming with a surface pellicle. Grows best between 15° C. and 45° C., no growth at 50° C.

| | |
|---|---|
| KOH test: | positive |
| Aminopeptidase: | positive |
| oxidase: | very weakly positive, may be seen as negative |
| Catalase: | positive |
| NaCl tolerance: | 0% to ? 12%, no growth at 15% |
| Hydrolysis of Gelatin: | negative |
| Hydrolysis of Starch: | negative |
| Major polar lipid components: | phosphatidylglycerol diphosphatidylglycerol phosphatidylglycerol phosphate phosphatidylethanolamine |
| Major ubiquinone: | Q9 |
| Major fatty acids: | C16:0, 11-cis C18:1 |
| G + C: | 65.3 mol % (T.) |

Chemoorganotroph. Grows well on complex substrates such as yeast extract. Growth on simple sugars is restricted. Grows on organic acids (e.g., lactate, acetate, fumarate), fatty acids (e.g., propionate, valerate, caprate) and amino acids (e.g., proline, serine, lysine).

Strain 17N.1$^{CT}$ (cluster 5)

An aerobic, Gram-negative, long, thin, rod-shaped, bacterium, 5.5–10.5 μm×0.6 μm, sometimes forming short chains of cells. With age pleomorphic, peculiar swollen forms predominate.

Obligate alkaliphile, grows best between pH 8 and pH 10.5.

On alkaline-agar, (Medium A) forms smooth, opaque, yellow, colonies, 2–3 mm in diameter. The colonies vary from circular to irregular in form, with a convex to umbonate elevation, and entire, undulate or lobate margin, depending upon age.

In alkaline-broth (Medium A), growth (37° C.) is even and sediment forming with no surface pellicle.

Grows well between 15° C. and 37° C. Grows slowly at 10° C. and not at all at 8° C. No growth at 40° C. or above.

| | |
|---|---|
| KOH test: | positive |
| Aminopeptidase: | weakly positive |
| Oxidase: | negative |
| Catalase: | positive |
| NaCl tolerance: | 0% to <12%, grows best at 0% NaCl |
| Hydrolysis of Gelatin: | positive |
| Hydrolysis of Starch: | weakly positive |
| Major polar lipid components: | phosphatidylglycerol diphosphatidylglycerol phosphatidylglycerol phosphate phosphatidylethanolamine glycolipid (α-naphthol positive) |
| major ubiquinone: | Q9, Q10 |
| Major fatty acids: | C15:0 anteiso, C16:0, C17:0 anteiso |
| G + C: | 50.0 mol % (HPLC) |

Chemoorganotroph. Grows well on complex substrates such as yeast extract. Growth on simple sugars is restricted (e.g., growth observed only on fructose; no growth observed on glucose, ribose, lactose). Grows on organic acids (e.g., fumarate, succinate, pyruvate, 2-ketogluconate) and amino acids.

Strain 64B.4$^{CT}$ (cluster 6)

An aerobic, Gram-negative, rod-shaped bacterium 2.0–3.5 μm×0.8–1.0 μm.

Obligate alkaliphile, grows best between pH 8.2 and pH 10.9.

On alkaline-agar, (Medium A) forms smooth, opaque colonies, first creamy yellow in color, becoming beige with age. The colonies are about 4 mm in diameter, circular becoming irregular; flat or low convex in elevation becoming convex; with an entire margin becoming undulate.

In alkaline-broth (Medium A), growth (37° C.) is even, sediment forming with no surface pellicle.

Grows well at 15° C. to 45° C., no growth at 10° C. or 50° C.

| | |
|---|---|
| KOH test: | positive |
| Aminopeptidase: | negative |
| Oxidase: | positive |
| Catalase: | positive |
| NaCl tolerance: | 0% to ≦12%, no growth at 15% |
| Hydrolysis of Gelatin: | positive |
| Hydrolysis of Starch: | weakly positive |
| Major polar lipid components: | phosphatidylglycerol |
| | diphosphatidylglycerol |
| | phosphatidylglycerol phosphate |
| | phosphatidylethanolamine |
| | glycolipid (α-naphthol positive) |
| Major ubiquinone: | Q9 |
| Major fatty acids: | C15:0 iso, C15:0 anteiso, |
| | C16:0 G + C: 41.0 ± 0.9 mol % |
| | (HPLC) |

Chemoorganotroph. Grows well on complex substances such as yeast extract. Grows on some simple sugars (e.g., glucose, ribose, maltose and fructose), organic acids (e.g., acetate, lactate, citrate and fumarate), some fatty acids (e.g., propionate and caprate) and amino acids (e.g., proline, histidine and alanine).

Non-Clustering Strains

The strains which do not fall into the clusters defined here are also novel bacteria not previously known or described. These strains, coded wN2, 4E.1, 5E.1, 92LM.4 and wBn5, may represent rarer varieties of alkaliphilic bacteria and are probably members of clusters of bacteria representing new genera and species at present not described. A description of these "non-clustering" strains has been made so as to be able to distinguish these organisms from all other bacteria previously known and described.

Strain wN2

An aerobic, Gram-negative, motile, rod-shaped bacterium, frequently in pairs.

Obligate alkaliphile, grows best between pH 9 and pH 10.

On alkaline-agar, (Medium A) forms smooth, translucent, beige colored colonies, 1–2 mm in diameter. The colonies are circular, convex with an entire margin.

In alkaline-broth (Medium A), growth (37° C.) is flocculent with a ring or surface pellicle and formation of a sediment.

Grows well at 20° C. to 30° C. No growth at 15° C. or 40° C.

| | |
|---|---|
| KOH test: | positive |
| Aminopeptidase: | weak positive |
| Oxidase: | weak positive |
| Catalase: | positive |
| NaCl tolerance: | obligate halophile, growth at 4% NaCl |
| | no growth at 0% or 8% NaCl |
| Hydrolysis of Gelatin: | slow positive |
| Hydrolysis of Starch: | positive |
| Major ubiquinone: | Q9 |
| G + C: | 64.1 (T$_M$) |

Chemoorganotroph. Metabolically unreactive. No growth on simple sugars or organic acids. Grows on complex substrates such as yeast extract and peptones, and on some amino acids.

Strain 4E. 1

An aerobic, Gram-negative, motile, rod-shaped bacterium, 1.7–5.2 μm×0.75 μm.

Obligate alkaliphile, grows best between pH 8.2 and pH 10.9.

On alkaline-agar, (Medium A) forms smooth, opaque, beige or brown colored colonies, 2–4 mm in diameter. The colonies are circular in form, convex in elevation, with an entire margin.

In alkaline-broth (Medium A), growth (37° C.) is heavy and flocculent with a sediment and surface pellicle.

Grows well between 20° C. and 37° C. Grows very slowly at 10° C. and not at all at 8° C. No growth at 40° C or above.

| | |
|---|---|
| KOH test: | positive |
| Aminopeptidase: | positive |
| Oxidase: | very weakly positive, can appear negative |
| Catalase: | positive |
| NaCl tolerance: | 0% to 12%, may grow weakly at 15% |
| | no growth at 20% |
| Hydrolysis of Gelatin: | negative |
| Hydrolysis of Starch: | negative |

Chemoorganotroph. Does not grow on simple sugars, except for ribose. Grows well on complex substrates such as yeast extract, and on organic acids (e.g., succinate, pyruvate, citrate, malonate, acetate and lactate), fatty acids (e.g., propionate, valerate and suberate), and amino acids (e.g., proline, serine, histidine and lysine).

Strain 5E.1

An aerobic, Gram-negative, rod-shaped bacterium, 3.0–5.3 μm×1.3 μm.

Obligate alkaliphile, grows best between pH 9 and pH 10.5.

On alkaline-agar, (Medium A) forms smooth, opaque, brown colored colonies, 3–4 mm in diameter. The colonies are fairly irregular in form, generally flat to slightly umbonate in elevation with a lobate margin. In alkaline-broth (Medium A), growth (37° C.) is moderate to heavy, becoming flocculent with a sediment and surface pellicle.

Grows well between 20° C. and 40° C. Grows slowly at 10° C. No growth at 45° C.

| | |
|---|---|
| KOH test: | positive |
| Aminopeptidase: | positive |
| Oxidase: | negative |
| Catalase: | positive |
| NaCl tolerance: | 0% to 12%, may grow weakly at 15% |
| | no growth at 20% |
| Hydrolysis of Gelatin: | positive |
| Hydrolysis of Starch: | weakly positive |
| Major polar lipid components: | phosphatidylglycerol |
| | diphosphatidylglycerol |
| | phosphatidylglycerol phosphate |
| | phosphatidylglycerol sulphate |
| | phosphatidylethanolamine |
| | glycolipid (α-naphthol positive) |

| | |
|---|---|
| Major ubiquinone: | Q8 |
| Major fatty acids: | C16:0, C18:1 |

Chemoorganotroph. Does not grow on simple sugars. Grows well on complex substrates such as yeast extract, organic acids (e.g., pyruvate, citrate, acetate and lactate), fatty acids ( e.g., propionate, caprate and valerate ) and amino acids (e.g., proline, alanine and lysine).

Strain 92LM.4

An aerobic, Gram-negative, rod-shaped bacterium, 2.0–3.5 μm×0.5–1.0 μm.

Obligate alkaliphile, no growth below pH 7.5.

On alkaline-agar, (Medium A) forms smooth, cream colored colonies, initially translucent but becoming opaque. The colonies develop from circular, entire to irregular, lobate in form, with a convex elevation.

In alkaline-broth (Medium A) , growth (37° C.) is slow, slight, flocculent with a sediment but no surface pellicle.

Grows between 10° C. and 40° C., no growth at 8 ° C. or 45° C.

| | |
|---|---|
| KOH test: | positive |
| Aminopeptidase: | negative |
| Oxidase: | positive |
| Catalase: | positive |
| NaCl tolerance: | 0% to 15%, growth at 15% is slow no growth at 20% |
| Hydrolysis of Gelatin: | positive |
| Hydrolysis of Starch: | weakly positive |
| Major ubiquinone: | Q9 |
| Major fatty acids: | C15:0 iso, C15:0 anteiso, C16:0, C17:0 iso |

Chemoorganotroph. Grows on complex substrates such as yeast extract and peptones, and a variety of sugars, organic acids and amino acids.

Strain wBn5

An aerobic, Gram-negative, small, rod-shaped bacterium, frequently forming short chains of cells.

Obligate alkaliphile, no growth below pH 8.

On alkaline-agar, (Medium A) forms smooth, circular, convex colonies with an entire margin, about 1 mm in diameter. The colonies are initially cream/beige, transparent becoming opaque, brown.

In alkaline-broth (Medium A), growth (37° C.) is initially evenly turbid with a sediment but no surface pellicle becoming after 4 days flocculent with formation of a pellicle.

| | |
|---|---|
| KOH test: | positive |
| Aminopeptidase: | positive |
| Oxidase: | positive |
| Catalase: | positive |
| NaCl tolerance: | obligate halophile. Growth at 4% NaCl no growth at 0% or 8% |
| Hydrolysis of Gelatin: | slow positive |
| Hydrolysis of Starch: | negative |
| Major ubiquinone: | Q8, Q9 |
| G + C: | 54.6 mol % ($T_M$) |

Chemoorganotroph. Grows on a range of complex substrates such as yeast extract and peptones, as well as sugars, organic acids, fatty acids and amino acids.

Cluster Definition by the Calculation of the Minimum Number of Discriminatory Tests, and the Construction of a Probability Matrix for the Identification of Gram-Negative Alkaliphiles One of the purposes of a numerical classification study is to use the phenetic data, which defines the clusters at a selected similarity level, for the assignment or identification of unknown strains. The classification test data can be used to determine the minimum set of tests which are required to define the clusters at the 73% ($S_G$) similarity level, and to identify those characters which are most diagnostic (predictive) for the individual clusters. In other words, the minimum number of tests required to assign an unknown organism to a pre-determined cluster with a high degree of predictability.

From the minimum discriminatory tests, a probability matrix can be constructed for the identification of unknown strains. The analysis is achieved by using a combination of the CHARSEP and DIACHAR (TAXPAK) and MCHOICE (not on TAXPAK but available by Data-Mail from the University of Leicester, U.K.) programs. An evaluation of the identification matrix is provided by using the MOSTTYP and OVERMAT programs. Practical examples of the use of these programs for the probabilistic identification of bacteria have been published by Williams, S. T., et al., (1983), J. Gen. Microbiol., 129, pp. 1815–1830; and Priest, F. G. and Alexander, B., (1988), J. Gen. Microbiol., 134, pp. 3011–3018; ibid, (1990), 136, pp. 367–376.

A "nxt" table was constructed from the test data using characters 6 to 10 and 13 to 104 (Appendix C) scored in binary notation (positive=1, negative=0). This data matrix was supplemented with the following four extra character states:

[105] Bright yellow colonies (character number 1, Appendix C)

[106] Translucent colonies (grown on Medium A, Appendix A)

[107] Lipase (lipolytic activity on olive oil (Medium M))

[108] Oxidase positive within 10 secs. (test 9, Appendix B)

The data matrix is first examined using the CHARSEP program which calculates separation indices and thus the diagnostic value of the individual characters for discriminating between the clusters. Tests with a VSP index>25% (Sneath, P. H. A., (1979), Computers and Geosciences, 5, 349–357) are accepted, characters with a low diagnostic value (VSP<25%) were rejected. A preference is made for characters with the highest VSP indices, provided that the criteria in the DIACHAR and MCHOICE programs are also met. In this example, 38 tests have a VSP index>25%, and 9 of the 24 characters finally chosen have a VSP index>50% (Table 11).

The data matrix is next re-examined by means of the DIACHAR program, which determines the most diagnostic character states of each of the clusters. The number of character states was set at 10. This result allows the choice of mutually exclusive character states between the clusters. As many of these tests as possible are retained in the final identification matrix of minimum discriminatory tests; in this example between 6 and 9 diagnostic characters per cluster. The remaining, unused tests are also noted and may be applied as additional tests for the confirmation of identification (Table 12).

The MCHOICE program ranks the tests in groups which can be displayed in the form of a dendrogram using the MDEND sub-routine. The groups identify tests with similar discriminatory value, thus allowing the rejection of tests which fail to make a significant discrimination as well as allowing choices to be made between tests of equal or very similar diagnostic value.

Table 13 shows the set of 24 tests which is the minimum number required to define the clusters and which can be used for the assignment of unknown strains. In addition, Table 13 shows the identification matrix which consists of the percentage of positive characters which define the clusters on the basis of the 24 minimum discriminatory tests. This is computed by the IDMAT program.

TABLE 14

Separation Values of Characters used for the Minimum Discriminatory Tests

| CHARACTER | VSP Index |
|---|---|
| [23] N-acetylglucosamine | 35.4 |
| [26] Saccharose | 44.8 |
| [27] Maltose | 41.4 |
| [32] Lactate | 51.6 |
| [41] Propionate | 60.9 |
| [43] Valerate | 63.4 |
| [44] Citrate | 45.1 |
| [45] Histidine | 38.0 |
| [47] Glycogen | 31.7 |
| [51] 3-hydroxybutyrate | 66.1 |
| [52] 4-hydroxybenzoate | 38.0 |
| [58] Leucine arylamidase | 36.6 |
| [59] Valine arylamidase | 50.5 |
| [64] Phosphohydrolase | 52.8 |
| [65] α-galactosidase | 33.9 |
| [85] Ampicillin | 36.8 |
| [92] Fusidic Acid | 68.7 |
| [93] Methicillin | 58.3 |
| [99] Polymixin | 62.8 |
| [102] Vancomycin | 48.3 |

TABLE 15

Discriminatory Tests for Each of the Six Clusters ($S_G$)

| Positive | Negative |
|---|---|
| Cluster 1: cream, circular, opaque, mucoid colonies. | |
| [58] Leucine arylamidase (91%) | [23] N-acetylglucosamine (9%) |
| [59] Valine arylamidase (91%) | [27] Maltose (9%) |
| [64] Phosphohydrolase (91%) | [41] Propionate (9%) |
| [99] Polymixin (89%) | [42] Caprate |
| | [43] Valerate (9%) |
| | [44] Citrate (9%) |
| | [45] Histidine |
| | [47] Glycogen (9%) |
| | [52] 4-hydroxybenzoate |
| | [65] α-galactosidase |
| Cluster 2: small, cream, translucent colonies. | |
| [21] Starch | [23] N-acetylglucosamine |
| [31] Acetate | [26] Saccharose |
| [41] Propionate | [45] Histidine |
| [43] Valerate | [50] 2-ketogluconate |
| [53] Proline | [52] 4-hydroxybenzoate |
| [107] Lipase | [68] α-glucosidase |
| [108] Oxidase (within 10 secs.) | [69] β-glucosidase |
| | [92] Fusidic Acid |
| Cluster 3: cream, opaque colonies. | |
| [31] Acetate | [64] Phosphohydrolase (3%) |
| [32] Lactate | [65] α-galactosidase (3%) |
| [41] Propionate (94%) | [92] Fusidic Acid (3%) |
| [43] Valerate (97%) | [96] Tetracycline (3%) |
| [44] Citrate (94%) | [102] Vancomycin |
| [51] 3-hydroxybutyrate (94%) | [104] Bacitracin |
| [53] Proline | |

TABLE 15-continued

Discriminatory Tests for Each of the Six Clusters ($S_G$)

| Positive | Negative |
|---|---|
| [58] Leucine arylamidase (94%) | |
| Cluster 4: beige to brown, opaque colonies. | |
| [32] Lactate | [45] Histidine |
| [33] Alanine | [85] Ampicillin |
| [48] 3-hydroxybutyrate | [86] Naladixic acid |
| [59] Valine arylamidase | [88] Trimethoprim |
| [99] Polymixin | [89] Penicillin G |
| | [93] Methicillin |
| Cluster 5: bright yellow [105], opaque colonies. | |
| [64] Phosphohydrolase | [23] N-acetylglucosamine |
| [65] α-galactosidase | [32] Lactate |
| [66] β-galactosidase | [33] L-alanine |
| [85] Ampicillin | [34] Mannitol |
| [92] Fusidic Acid | [41] Propionate |
| [93] Methicillin | [42] Caprate |
| [96] Tetracyclinee | [43] Valerate |
| [102] Vancomycin | [45] Histidine |
| [104] Bacitracin | [48] 3-hydroxybenzoate |
| | [51] 3-hydroxybutyrate |
| | [52] 4-hydroxybenzoate |
| | [99] Polymixin |
| Cluster 6: cream, irregular, flat colonies. | |
| [21] Starch | [17] Pyruvate |
| [23] N-acetylglucosamine | [52] 4-hydroxybenzoate |
| [26] Saccharose | [58] Leucine arylamidase |
| [27] Maltose | [59] Valine arylamidase |
| [31] Acetate | [65] α-galactosidase |
| [33] Alanine | [99] Polymixin |
| [44] Citrate | |
| [47] Glycogen | |
| [51] 3-hydroxybutyrate | |
| [89] Penicillin G | |
| [92] Fusidic Acid | |
| [93] Methicillin | |
| [96] Tetracyclinee | |
| [104] Bacitracin | |

Note:
The numbers in square brackets proceeding the character state refers to the character states and unit tests in Appendices B and C. The percentage in parenthesis refers to positive character states.

TABLE 16

A Probability Matrix for the Identification of Alkaliphiles: Percentage Distribution of Positive Discriminatory Characters Which Define the Clusters of Gram-Negative Alkaliphilic Bacteria at the 73% Level ($S_G$)

| TEST | CLUSTER | | | | | |
| --- | --- | --- | --- | --- | --- | --- |
| | 1 | 2 | 3 | 4 | 5 | 6 |
| [23] N-acetylglucosamine | 13 | 0 | 26 | 20 | 0 | 100 |
| [26] Saccharose | 25 | 0 | 74 | 20 | 25 | 100 |
| [27] Maltose | 25 | 0 | 68 | 60 | 50 | 100 |
| [32] Lactate | 38 | 50 | 100 | 100 | 0 | 40 |
| [41] Propionate | 0 | 100 | 91 | 60 | 0 | 80 |
| [43] Valerate | 13 | 100 | 97 | 80 | 0 | 40 |
| [44] Citrate | 13 | 50 | 94 | 20 | 50 | 100 |
| [45] Histidine | 0 | 0 | 71 | 0 | 0 | 80 |
| [47] Glycogen | 0 | 13 | 26 | 20 | 25 | 100 |
| [51] 3-hydroxybutyrate | 13 | 25 | 94 | 100 | 0 | 100 |
| [52] 4-hydroxybenzoate | 0 | 0 | 71 | 80 | 0 | 0 |
| [58] Leucine arylamidase | 88 | 63 | 94 | 60 | 50 | 0 |
| [59] Valine arylamidase | 88 | 25 | 65 | 100 | 25 | 0 |
| [64] Phosphohydrolase | 88 | 13 | 3 | 20 | 75 | 40 |
| [65] α-galactosidase | 0 | 0 | 3 | 20 | 75 | 0 |
| [85] Ampicillin | 50 | 63 | 56 | 0 | 100 | 80 |
| [92] Fusidic Acid | 25 | 0 | 3 | 20 | 100 | 100 |
| [93] Methicillin | 50 | 13 | 50 | 0 | 100 | 100 |

TABLE 16-continued

A Probability Matrix for the Identification of Alkaliphiles:
Percentage Distribution of Positive Discriminatory
Characters Which Define the Clusters of Gram-Negative
Alkaliphilic Bacteria at the 73% Level ($S_G$)

| TEST | CLUSTER | | | | | |
|---|---|---|---|---|---|---|
| | 1 | 2 | 3 | 4 | 5 | 6 |
| [99] Polymixin | 88 | 50 | 81 | 100 | 0 | 0 |
| [102] Vancomycin | 13 | 13 | 3 | 20 | 100 | 75 |
| [105] Yellow colony | 0 | 0 | 0 | 0 | 100 | 0 |
| [106] Translucent colony | 0 | 100 | 3 | 0 | 0 | 0 |
| [107] Lipase | 0 | 100 | 21 | 0 | 0 | 0 |
| [108] Oxidase (10 secs) | 25 | 88 | 6 | 0 | 0 | 0 |

Evaluation of the Discriminatory Tests and Assessment of the Reliability of Identification The evaluation of the discriminatory tests has two aspects. Firstly, the validity of the tests can be analyzed using practical examples, which can be further evaluated using statistical theory, or the tests can be directly subjected to theoretical assessment using statistical methods.

Illustration 1

A Practical Evaluation of the Discriminatory Tests

Figure 3A:
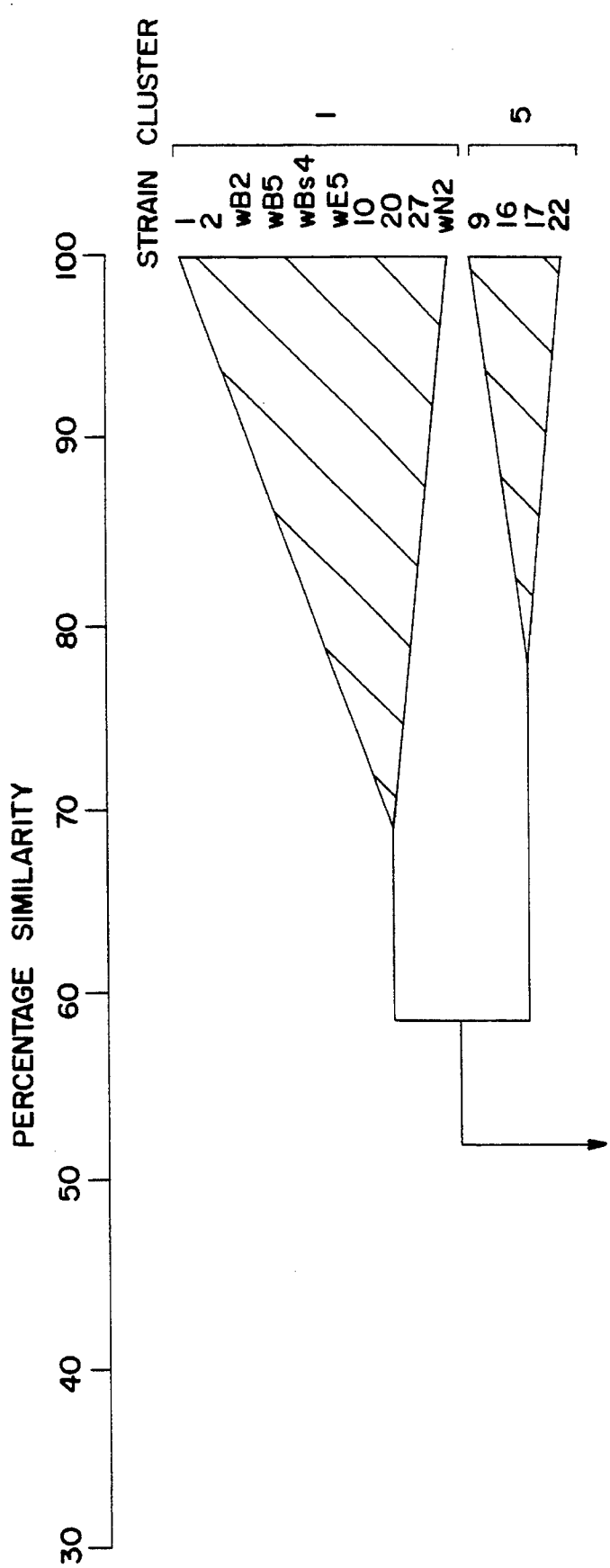
FIG. 3. (Sheet 1, Sheet 2 and Sheet 3) Simplified dendrogram obtained with the $S_G$ coefficient and Unweighted Average Linkage procedure show different cluster on Sheet 1, Sheet 2 and Sheet 3 using the derived minimum discriminatory tests.
Figure 3B:
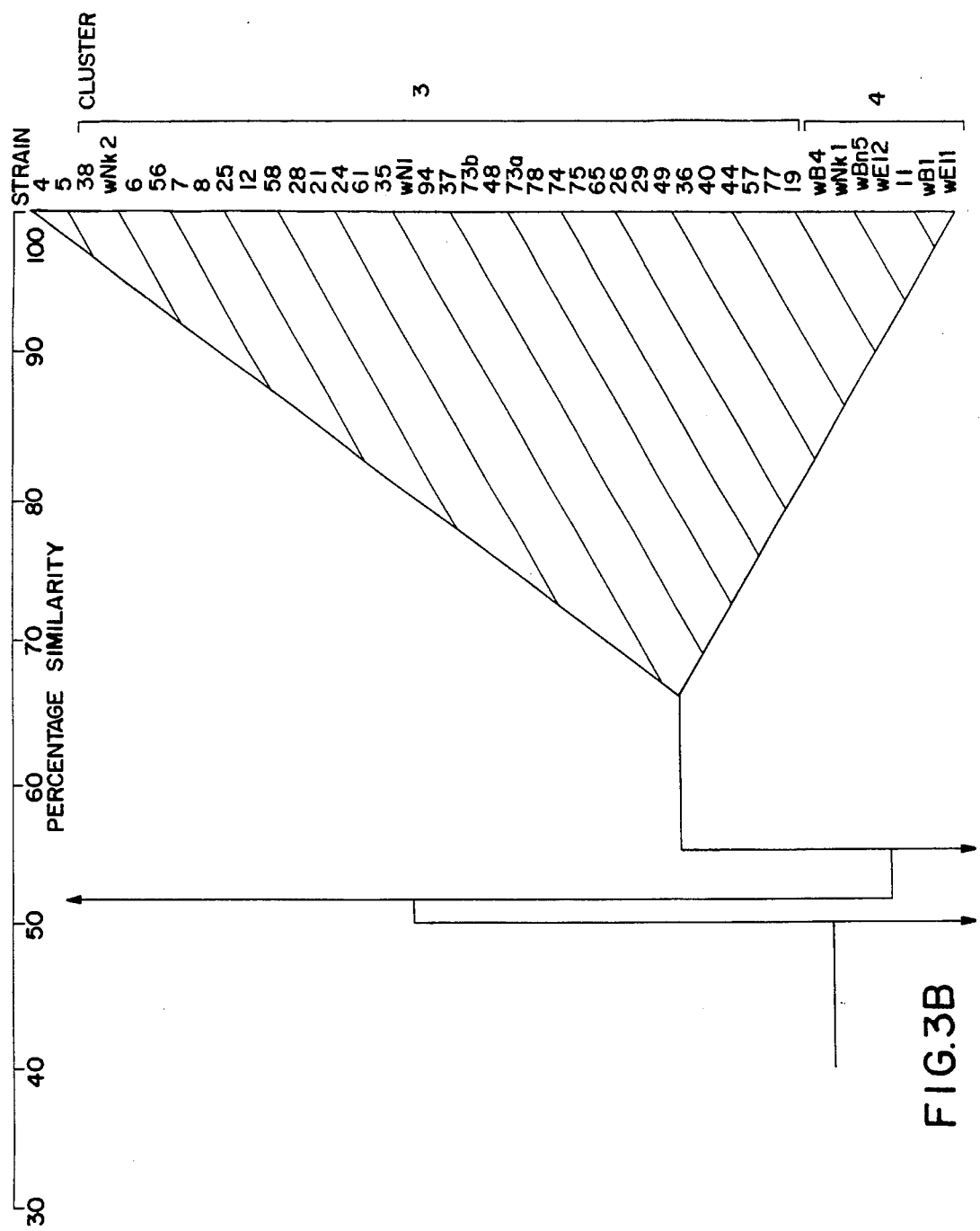
Figure 3C:
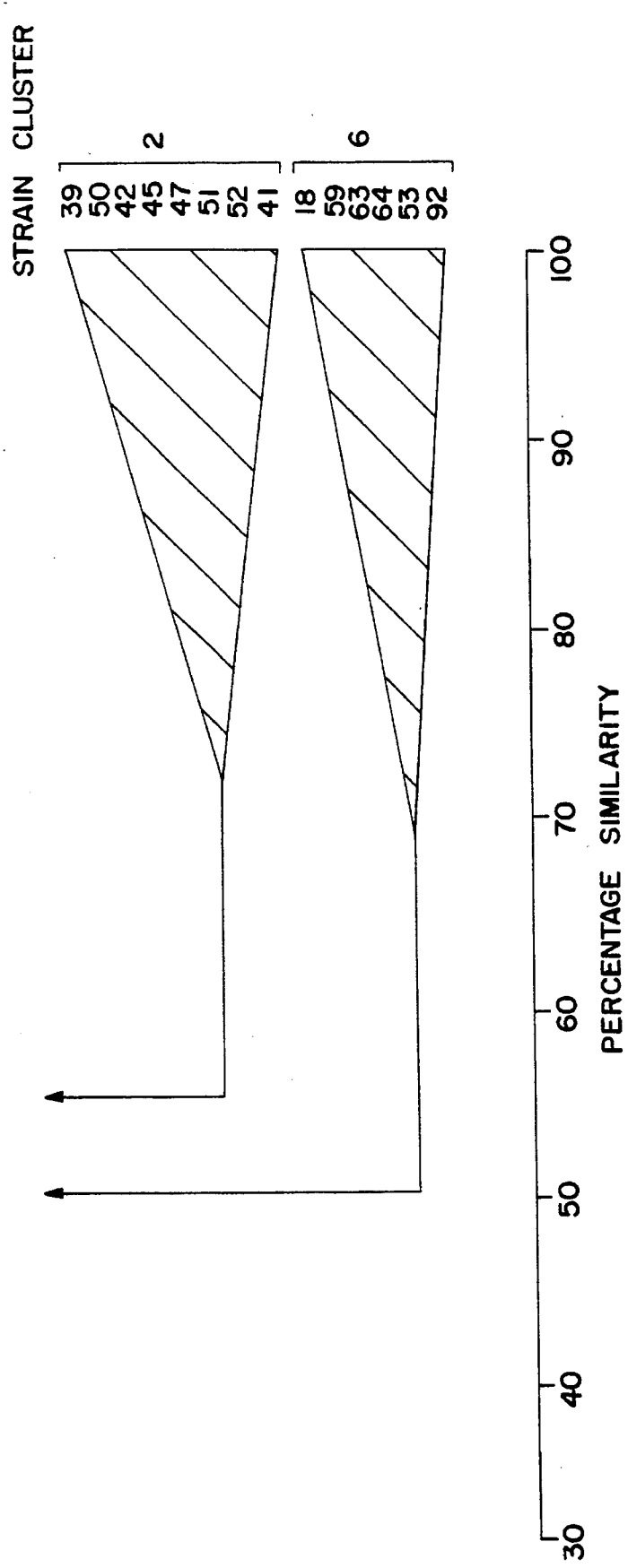

Many workers assess the accuracy of the discriminatory tests only by redetermining the character states of selected cluster representatives. This approach has been used here for the centrotype strains (see below). A far more stringent approach which is seldom applied, is to examine all the strains which were used in the original numerical taxonomic analysis. When subjected to cluster analysis using only the data acquired from the derived set of minimum discriminatory tests, the reconstructed dendrogram can be compared with the original. Using only the 24 discriminatory tests previously described (Table 16), the data (two-state, binary form) for all 70 of the novel Gram-negative alkaliphilic bacteria were subjected to cluster analysis by the $S_G$/UPGMA method. The reconstructed dendrogram is reproduced in FIG. 3. This reconstructed dendrogram compares very favorably with the original dendrogram (FIG. 1).

Although there has been some rearrangement of position of the clusters, their composition is largely unchanged and they are defined at approximately the same similarity level as the original. Cluster 4 however, has combined with Cluster 3, with a single strain moving to Cluster 1. This further serves to emphasize the difficulty of defining Cluster 4 on phenetic data alone. It has been stressed several times that supplementary chemotaxonomic data are required to make the proper distinction between Cluster 3 and Cluster 4.

In both the original dendrogram and the reconstruction (FIG. 3), Cluster 3 appears to comprise several subclusters above the 73% similarity level. The fine structure of cluster 3 is also supported by the chemotaxonomic data (see above).

Illustration 2

A Theoretical Evaluation of the Discriminatory Tests

An assessment of cluster overlap is achieved using the OVERMAT program. This program examines the matrix constructed from the percentage positive values for the selected character states against a critical overlap value by considering the clusters defined by the coordinates of the centroid and the cluster radius (twice root mean square of the distances of the strains from the centroid). If there is significant overlap between the clusters, unknown strains may not identify with sufficient confidence to any one of them (Sneath, P. H. A. and Sokal, R. R., supra, p. 394–400). At a chosen critical overlap value of 2.5% (which is a more stringent condition than is used by most workers: see Priest, F. G. and Alexander, B., (1988), supra; and Williams, S. T. et al., (1983), supra) there was no significant overlap between the clusters (95% confidence level) except between Cluster 3 and Cluster 4 where the actual overlap was calculated to be 4%. However, chemotaxonomic data (see above) was not taken into account when constructing the identification matrix. On the basis of quinone analyses, strains from Cluster 3 can be distinguished from the strains of Cluster 4.

Illustration 3

A Theoretical Assessment of the Reliability of Identification

The hypothetical median organism (HMO) is another estimate of the "average" organism in a cluster (Sneath, P. H. A. and Sokal, R. R., supra, pp. 194 et seq.). A HMO is not a real strain but a hypothetical organism possessing the most common state for each character. The MOSTTYP program calculates HMO's for each cluster in the identification matrix and then attempts to identify them. In other words, MOSTTYP is a program to evaluate an identification matrix by calculating identification scores of the most typical strains against the clusters. A good identification matrix should give a high probability of a HMO being reassigned to its own cluster. The results of this analysis were very satisfactory (Table 17), especially since MOSTTYP was programed to consider only the first 20 diagnostic tests of the identification matrix (Table 16), i.e. excluding tests 105–108. Each HMO was reassigned to its original cluster with Willcox probabilities of 0.998–1.000 (Willcox, W. R. et al., (1973) J. Gen. Microbiol., 77, 317–330). The Taxonomic Distances were all low and the standard errors of the Taxonomic Distance were all negative, indicating that the HMO's were all closer to the centroid of the cluster than the average for the cluster (Table 17).

TABLE 17

Identification Scores for the Hypothetical Median Organism of each cluster provided by the MOSTTYP Program

| | Identification Score | | |
|---|---|---|---|
| CLUSTER | Willcox Probability | Taxonomic Distance | Standard Error of Taxonomic Distance |
| 1 | 0.999 | 0.194 | −2.742 |
| 2 | 0.999 | 0.236 | −2.214 |
| 3 | 1.000 | 0.231 | −2.115 |
| 4 | 0.998 | 0.195 | −2.998 |
| 5 | 1.000 | 0.217 | −1.839 |
| 6 | 1.000 | 0.182 | −2.502 |

Illustration 4

A Practical Evaluation of Identification Score

Identification of strains using the minimum set of discriminatory tests is achieved using the MATIDEN program in TAXPAK. The program compares presence-absence data for an unknown strain against each cluster in turn in an identification matrix of percentage positive characters. Identification coefficients are computed, namely Willcox probability, Taxonomic Distance and the Standard Error of the Taxonomic Distance. The results are displayed, showing the identification scores to the best cluster and to the two next best alternative clusters. Additionally, the atypical results ("characters against") are recorded. In an analysis using data from real strains, the centrotypes were reassigned to their original clusters with Willcox probabilities of 0.9996–1,000 (Table 18). The Taxonomic Distances were low. The Standard Errors of the Taxonomic Distance were all negative indicating that the centrotypes were closer to the centroid of the cluster than the average for the cluster.

TABLE 18

Identification Scores for the Centrotype Organisms of Each Cluster Provided by the MATIDEN Program

| Cluster | Strain | Assigned to Cluster | Identification Score | | |
|---|---|---|---|---|---|
| | | | Willcox Probability | Taxonomic Distance (D) | Standard Error of D |
| 1 | 2E.1$^{CT}$ | 1 | 1.000 | 0.309 | −0.283 |
| 2 | 45E.3$^{CT}$ | 2 | 1.000 | 0.226 | −1.749 |
| 3 | 28N.1$^{CT}$ | 3 | 1.000 | 0.305 | −0.622 |
| 4 | wB4$^{CT}$ | 4 | 0.9996 | 0.265 | −1.092 |
| 5 | 17N.1$^{CT}$ | 5 | 0.9999 | 0.255 | −0.478 |
| 6 | 64N.4$^{CT}$ | 6 | 1.000 | 0.211 | −1.126 |

Illustration 5

Identification of Unknown Isolates

The identification matrix was assessed for the ability to assign unknown Gram-negative alkaliphiles to the clusters defined herein. The criteria for a successful identification were:

(a) bacteria isolated from a habitat similar to, but geographically separate from, the East African soda lakes;

(b) a Willcox probability greater than 0.95 and low values for Taxonomic Distance and its standard error (<3);

(c) an identification score to the best cluster significantly better than those against the two next best alternatives;

(d) "characters against" the best cluster should be zero or few in number.

Unknown microorganisms may be examined using the minimum tests listed in Table 16. The character states are determined and identification scores obtained using the MATIDEN program. This program compares the character states of the unknown with the identification matrix determined for all of the predetermined clusters, computes the best match and assigns the unknown to the most appropriate cluster.

A Willcox probability is calculated to determine the acceptability of identification. Willcox probabilities of 0.85 and 0.95 have been accepted as criteria for a successful identification (Williams, S. T., et al. (1983), supra; Priest, F. G. and Alexander, B., (1988), supra). The Taxonomic Distance of the unknown from the cluster centroid is calculated and may be compared to the radius of the cluster. The Standard Error of the Taxonomic Distance should be less than the upper value of +3.0 suggested by Sneath, P. H. A. ((1979), pp. 195–213). Moreover, physical characteristics, additional biochemical data and chemotaxomomic markers may be used to further confirm the identity of the unknown in a particular cluster.

The results provided by these five illustrations, together with the statistical data provided by the numerical taxonomic analysis and the chemotaxonomic data, indicate a robust classification which identifies 6 major groups of new, Gram-negative, alkaliphilic bacteria.

Phylogenetic Analysis

Phylogenetics is the study of relationships based on ancestry, in other words phylogeny reflects the evolutionary pathways of organisms (Austin, B. and Priest, F. G., (1986), pp. 5–9, 57–60, 74–81, ibid). The current practice in microbiology is to use macromolecule sequences in the construction of cladograms (genealogical trees) (Woese, C. R. (1987), Microbiol. Rev. 51, 221–271) which reveal evolutionary relationships. The most useful molecules for revealing prokaryotic phylogeny are the ribosomal RNAs (Woese, C. R. (1985), ibid, pp. 227 et seq.).

Chromosomal DNA was extracted using the method of Sambrook, J. et al., (1989), (in Molecular Cloning, a laboratory manual, (Sambrook, J., Fritsch, E. F. and Maniatis, T., eds.) Cold Spring Harbor Laboratory Press, N.Y.). The gene encoding 16S rRNA was amplified by the polymerase chain reaction (PCR) using modifications of the method of Weisburg, W. G. et al., (1991), (J. Bacteriol. 173, 697–703,). Twenty-five cycles of denaturation (94° C. for 1 minute), annealing (55° C. for 1 minute) and extension (72° C. for 1 minute) were performed. DNA was denatured at 98° C. for 5 minutes prior to adding the enzyme, and at the end of the last cycle, the extension time was lengthened to 7 minutes. The primers used are written in 5' to 3' orientation and the numbering based on the 16S rRNA sequence of E.coli (Brosius, J. et al., (1978), Proc. Natl. Acad. Sci. (USA), 75, 4801–4805).

The forward amplification primer was fD1, AGAGTTTGATCCTGGCTCAG (position 8-27) and the reverse primer was a mixture of rP1, ACGGTTACCTTGT-TACGACTT; rP2, ACGGCTACCTTGTTACGACTT and rP3, ACGGATACCTTGTTACGACTT (position 1512-1492).

The amplified PCR product was purified using QIAGEN purification system (Qiagen, Inc., Chatsworth, Calif.). Direct automated sequencing of 16S rDNA amplified by PCR was performed on a model 373A DNA Sequencer® (Applied Biosystems, Foster City, Calif.) using a modification of the method of Hiraishi, A. (1992), (Lett. Appl. Microbiol. 15, 210–213,). Sequencing was performed by dye-labelled dideoxy-sequencing using the method of Johnson-Dow, L. et al., (1987), (Biotechniques, 5, 754–765) with 25 asymmetrical thermal cycles.

A mixture of 3 reverse primers and 3 forward primers was used:

rD2;
    GAATTACCGCGGCGGCTG (position 536-519),
    GAATTACCGCGGCTGCTG (position 536-519),
    GTATTACCGCGGCGGCTG (position 536-519),
    GTATTACCGCGGCTGCTG (position 536-519);

rD3;
    CCGTCAATTCCTTTGAGTTT (position 926–907),
    CCGTCAATTCCTTTAAGTTT (position 926-907),
    CCGTCAATTCATTTGAGTTT (position 926-907),
    CCGTCAATTCATTTAAGTTT (position 926-907);

rD4;
    ACGGGCGGTGTGTGTAC (position 1406-1390),
    ACGGGCGGTGTGTGTGC (position 1406-1390);

fD2;
    CAGCCGCCGCGGTAATTC (position 519-536),
    CAGCAGCCGCGGTAATTC (position 519-536),
    CAGCCGCCGCGGTAAATC (position 519-536),
    CAGCAGCCGCGGTAAATC (position 519-536);

fD3;
    AAACTTAAATGAATTGACGG (position 907-926),

AAACTCAAATGAATTGACGG (position 907-926),
AAACTTAAAGGAATTGACGG (position 907-926),
AAACTCAAAGGAATTGACGG (position 907-926);
fD4;
GTACACACACCGCCCGT (position 1390-1406),
GCACACACACCGCCCGT (position 1390-1406).

The strains used in the sequence analysis are listed in Table 19.

TABLE 19

Source of 16S rRNA Sequences for Phylogenetic Analysis

| Species | Access Number | Strain Specification | Reference |
|---|---|---|---|
| Magatibacter afermentans | | 1E.1$^{CT}$ | This study |
| Sodabacter nakuruai | | 28N.1$^{CT}$ | This study |
| Igatibacter hanningtonii | | 64B.4$^{CT}$ | This study |
| Halomonas elongata | X67023 | ATCC 33173 | Gauthier, M. J., et al. (1992) (Int. J. Syst. Bacteriol. 42, 568–576). |
| Halomonas halmophila | M59153 | ATCC 19717 | Woese, C. R. (unpublished) |
| Pseudomonas aeruginosa | X06684 | DSM 50071 | Toschka, H. Y., et al. (1988) (Nucl. Acids Res. 16, 2348-2348). |
| Marinomonas vaga | X67023 | ATCC 27119 | Gauthier, M. J., et al. (1992) ibid. |
| Legionella pneumophila | M36024 | NCTC 11286 | Fry, N. K., et al. (1991) (J. Gen. Microbiol. 137, 1215–1222). |
| Acinetobacter calcoaceticus | M34139 | ATCC 33604 | Woese, C. R. (unpublished) |
| Alteromonas haloplanktis | X67024 | ATCC 14393 | Gauthier, M. J., et al. (1992) ibid. |
| Aeromonas sp. | X60417 | ATCC 39541 | Martinez-Murcia, A. J., et al. (1992) (Int. J. Syst. Bacteriol. 42, 412–421). |
| Plesiomonas shigelloides | X60418 | NCIMB 9242 | Martinez-Murcia, A. J., et al. (1992) ibid. |
| Proteus vulgaris | X07652 | IFAM 1731 | Stackebrandt, E. (unpublished) |
| E. coli | M24828 | | Carbon, P., et al. (1979) (Eur. J. Biochem. 100, 399–410). |
| Marinoacter hydrocarbonoclasticus | X67022 | ATCC 49840 | Gauthier, M. J., et al. (1992) ibid. |
| Oceanospirillum linum | M22365 | ATCC 11338 | Woese, C. R. (Unpublished) |

Sequences were accessed from GenBank and EMBL databases or from the Ribosomal Database Project (RDP) (Olsen, G. J., et al., (1992), Nucleic Acids Research, supplement, 20, 2199-2200,). A preliminary alignment of sequences was performed using the program Clustal V (Higgens, D. G., et al., CABIOS, 8, 189–191,) and refined by employing secondary structure criteria of the RDP. The aligned sequences were subjected to phylogenetic analysis using programs in versions 3.4 or 3.5 c of the PHYLIP package (Felsenstein, J. (1989), Cladistics, 5, 164–166). Evolutionary distances were calculated using the nucleotide substitution model of Jukes, T. H. and Cantor, R. R. (1969) (in *Mammalian protein metabolism*, (Munzo, H. N., ed.), Academic Press, New York, pp. 21–132) in the program DNADIST. A phylogenetic tree (FIG. 4) based on these values was constructed using the least squares algorithm of Fitch, W. M. and Margoliash, E. (1967), (Science, 155, 279–284) in the program FITCH.

The sequence of the 16S rRNA gene from strain 1E.1$^{CT}$ consisted of 1450 bases, (96% complete); strain 28N.1$^{CT}$ consisted of 1494 bases, (98% complete); and strain 64B.4$^{CT}$ consisted of 1461 bases, (95% complete). The phylogenetic analysis revealed that all 3 alkaliphilic strains of the present invention belong to the gamma-3 subdivision of the *Proteobacteria* (Woese, C. R., et al, (1985) (Syst. Appl. Microbiol. 6, 25–33). Strains 28N.1$^{CT}$ and 64B.4$^{CT}$ are evidently more closely related to each other than to strain 1E.1$^{CT}$. Strain 1E.1$^{CT}$ clearly represents a new genus within the Enteric-Aeromonas-Vibrio branch of the gamma-3 subdivision of the Proteobacteria for which we give the name Magatibacter (gen. nov.). Therefore, strain 1E.1$^{CT}$ which we name *Magatibacter afermentans* (gen. nov., sp. nov.) is the Type Strain representing all the strains of cluster 1. Strains 28N.1$^{CT}$ and 64B.4$^{CT}$ are clearly members of the Halomonas group, which includes Deleya, a deep branch of the gamma-3 subdivision of the Proteobacteria (woese, C. R., et al., (1985), ibid). The data (summarized in Table 20) indicates that both strain 28N.1$^{CT}$ and 64B.4$^{CT}$ deserve separate taxonomic status at the genus level. Although the percentage dissimilarity between strain 64B 4$^{CT}$, *Halomonas elongata* ATCC 33173 and *Halomonas halmophilum* ATCC 19717 (formally *Flavobacterium halmophilum*) based on the analysis of the 16S rRNA gene sequences is rather small, 4.9% and 4.8% respectively, the significantly lower G+C content of strain 64B.4$^{CT}$ (41 mol %) compared to the 59–63 mol % range for Halmonas (Vreeland, R. H. (1992), in *The Prokaryotes*, 2nd ed., vol. 4, (Balows, A., Truper, H. G., Dworkin, M., Harder, W. and Schleifer, K-H., eds.), pp. 3181–3188, Springer-Verlag, N.Y.) indicates a fundamental difference. Since strain 28N.1$^{CT}$ is no closer related to strain 64B.4$^{CT}$ than 64B.4$^{CT}$ is related to Halomonas (Table 20A) and 28N.1$^{CT}$ is more distantly related to Halomonas than 64B 4$^{CT}$, a separate generic status for the 2 obligately alkaliphilic strains of the present invention is undoubtedly indicated. This conclusion is further supported by G+C content, DNA-DNA reassociation studies and chemotaxonomic evidence (Table 20). Conclusive evidence for the separation of strain 28N.1$^{CT}$ and strain 64B.4$^{CT}$ from Halomonas as separate genera is the lack of 3 (strain 28N.1$^{CT}$) or 4 (strain 64B.4$^{CT}$) of the 6 unique signature sequences which are common to Halomonas (Table 20G) (Woese, C. R. et al., (1985), ibid).

Figure 4:
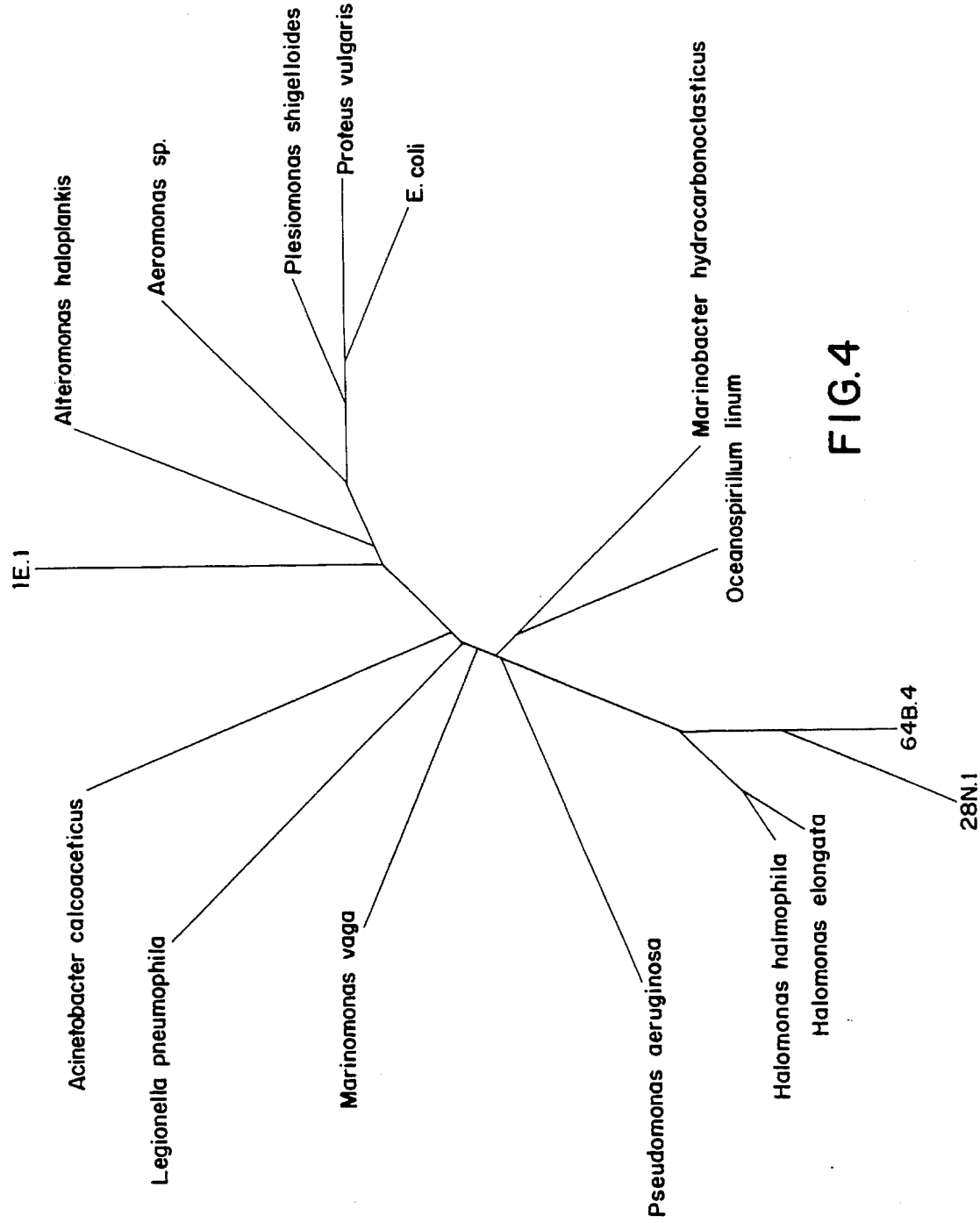
FIG. 4. Unrooted phylogenetic tree showing the relationship of 3 alkaliphilic bacteria to representatives of the gamma-Proteobacteria.

A distinction from the genus Deleya is more difficult to assess since only partial 16S rRNA gene sequences are available for *D. marina* (Kita-Tsukanoto, K., et al., (1993), (Int. J. Syst. Bacteriol. 43, 8–19). In order to minimize possible errors that might be introduced by comparison of partial sequence data, only complete 16S rRNA gene sequences were used in the construction of the phylogenetic tree (FIG. 4). However, when the partial 16S rRNA sequence of *Deleya marina* (Kita-Tsukanoto, K., et al., (1993), ibid) was aligned with sequences from *Malomonas elongata*, *Halomonas halmophila* and strain 64B 4$^{CT}$ and the percentage dissimilarity between species calculated (Table 21) a clear distinction was revealed. All this evidence, together with the unique alkaliphilic phenotype of the strains of the present invention indicates that strain 28N.1$^{CT}$ and strain 64B.4$^{CT}$ represent new, independent genera. Therefore, strain 28N.1$^{CT}$ which we name *Sodabacker nakuruai* (gen. nov., sp. nov.) is the Type Strain representing all the strains of cluster 3, and strain 64B.4$^{CT}$ which we name *Igatibacter hanningtonii* (gen. nov., sp. nov.) is the Type Strain representing all strains of cluster 6. From the preceding evidence and that of the numerical taxonomy and chemotaxonomy, it may be safely concluded that all the alkaliphilic bacteria of the present invention represent species of new genera.

TABLE 20

Comparison of Halomonas with Alkaliphilic Strain 28N.1 and 64B.4.

Table 20A.
Relative Phylogenetic Distance

|       | H.h. | H.e | 64B.4 |
|-------|------|-----|-------|
| H.h   |      |     |       |
| H.e   |      |     |       |
| 64B.4 | 54   | 66  |       |
| 28N.1 | 71   | 75  | 54    |

Table 20B.
G + C content mol %

| Halomonas | 59–63 |
|-----------|-------|
| 28N.1     | 64    |
| 64B.4     | 41    |

Table 20C.
DNA-DNA Hybridization

| Strain | 28N.1 | 64B.4 |
|--------|-------|-------|
| 28N.1  | 100   | 30    |
| 64B.4  | 35    | 100   |

Table 20D.
Major Respiratory Quinone

| Halomonas | Q9 |
|-----------|----|
| 28N.1     | Q6 |
| 64B.4     | Q9 |

Table 20E.
Major Fatty Acids

| Halomonas | C12:0, 3-OH-C12:0, iso-C15:0, C16:0, C16:1, C17:0, 9-trans-C18:1 |
| 28N.1     | C16:0, C16:1, 11-cis-C18:1 |
| 64B.4     | iso-C15:0, anteiso-C15:0, C16:0 |

Table 20F.
Polar Lipid Composition

| Halomonas | PG | DPG |     |    |     |
|-----------|----|----|-----|----|-----|
| 28N.1     | PG | DPG | PGP | PE | PGS |
| 64B.4     | PG | DPG | PGP | PE |     |

Table 20G.
RNA Signature Sequences

| Hal-omo-nas | | 28N.1 | 64B.4 |
|---|---|---|---|
| CCUACUUCG | + | – | – |
|  |  | CUAACCUUCG | CCUAACCUUCN |
| UUAAUACCCG | + | + | – |
|  |  |  | UUAAUACCCU |
| AUAACUUG | + | – | – |
|  |  | AUAACCUG | UNANCGUG |
| CCCUCG | + | – | – |
|  |  | CCUUCG | CCUUCG |
| UCUCAG | + | + | + |
| UUAACG | + | + | + |

TABLE 21

| | Percent Dissimilarity | | |
|---|---|---|---|
| | 64B.4 | Deleya marina | Halomonas elongata |
| 64B.4 | — | | |
| Deleya marina | 6.5 | — | |
| Halomonas elongata | 5.9 | 8.0 | — |
| Halomonas halmophilum | | | 2.9 |

Production and Application of Alkali-Tolerant Enzymes

The alkaliphilic microorganisms of the present invention produce a variety of alkali-tolerant enzymes. Examples of enzyme activities present in representative strains of the Gram-negative bacteria of the present invention may be found in Appendices D and E. These enzymes are capable of performing their functions at an extremely high pH, making them uniquely suited for their application in a variety of processes requiring such enzymatic activity in high pH environments or reaction conditions.

Examples of the various applications for alkali-tolerant enzymes are in detergent compositions, leather tanning, food treatment, waste treatment and in the textile industry. These enzymes may also be used for biotransformations, especially in the preparation of pure enantiomers.

The alkaliphilic bacteria of the present invention may easily be screened for the production of alkali-tolerant lipases, proteases and starch-degrading enzymes, inter alia, using the methods described herein.

The broth in which alkaliphilic bacteria are cultured typically contains one or more types of enzymatic activity. The broth containing the enzyme or enzymes may be used directly in the desired process after the removal of the bacteria therefrom by means of centrifugation or filtration, for example.

If desired, the culture filtrate may be concentrated by freeze drying, before or after dialysis, or by ultrafiltration. The enzymes may also be recovered by precipitation and filtration. Alternatively, the enzyme or enzymes contained in the broth may be isolated and purified by chromatographic means or by gel electrophoresis, for example, before being applied to the desired process. The exact methods used to treat the culture filtrate and/or to extract and/or purify the alkali-tolerant enzymes is not critical to the present invention, and may be determined by one skilled in the art.

The genes encoding alkali-tolerant enzymes of interest may be cloned and expressed in organisms capable of expressing the desired enzyme in a pure or easily recoverable form.

The following examples are provided to illustrate methods for the identification of Gram-negative alkaliphilic bacteria of the present invention, as well as methods of screening these alkaliphilic bacteria for the presence of various alkali-tolerant enzymes and methods for the subsequent production and application of these enzymes in industrial processes. These examples are not to be construed so as to limit the scope of the present invention.

EXAMPLE 1

Identification of Unknown Isolates

Six strains of Gram-negative, alkaliphilic bacteria were isolated from Mono Lake, a hypersaline, alkaline lake situated in California, U.S.A. (Javor, B., in *Hypersaline Environments*, Springer Verlag, Berlin and Heidelberg (1988), pp. 303–305). The strains were isolated from samples of partially submerged soda-encrusted wood, tufa and soda-soil collected from the environs of Mono Lake (California, U.S.A.) in May, 1990 by enrichment culture at 37° C. in Medium A (Appendix A). The six strains are described in Table 22. The strains were examined using 21 of the 24 minimum tests listed in Table 16. The character states were determined and identification scores obtained using the MATIDEN program. The results are outlined in Table 23.

TABLE 22

Alkaliphilic Strains from Mono Lake

| Strain | Sample | Colony Color | Form | Elevation | Margin | Cell Shape |
|---|---|---|---|---|---|---|
| ML005 | tufa | beige | circular | convex | entire | rod |
| ML104 | wood | pink/beige | circular | convex | entire | rod |
| ML201 | wood | yellow | circular | convex | entire | rod |
| ML203 | wood | pink/beige | circular | convex | entire | rod |
| ML206 | wood | yellow | circular | convex | entire | short rod |
| ML301 | soil | beige | circular | convex | entire | rod |

TABLE 23

Example of the Output from the MATIDEN Program to Identify Six Unknown Strains against the Identification Matrix A. Reference Number of unknown is ML005

| Character | Value in unknown | Percent in: Best Taxon | Percent in: Next Best Taxon |
|---|---|---|---|
| [23] N-acetylglucosamine | + | 26 | 20 |
| [26] Saccharose | + | 74 | 20 |
| [27] Maltose | + | 68 | 60 |
| [32] Lactate | + | 99 | 99 |
| [41] Propionate | + | 91 | 60 |
| [43] Valerate | + | 97 | 80 |
| [44] Citrate | + | 94 | 20 |
| [45] Histidine | + | 71 | 1 |
| [47] Glycogen | + | 26 | 20 |
| [51] 3-Hydroxybutyrate | + | 94 | 99 |
| [52] 4-Hydroxybenzoate | − | 71 | 80 |
| [58] Leucine arylamidase | + | 94 | 60 |
| [59] Valine arylamidase | + | 65 | 99 |
| [64] Phosphohydrolase | − | 3 | 20 |
| [65] α-Galactosidase | n.t. | 3 | 20 |
| [85] Ampicillin | − | 56 | 1 |
| [92] Fusidic Acid | − | 3 | 20 |
| [93] Methicillin | − | 50 | 1 |
| [99] Polymix | + | 81 | 99 |
| [102] Vancomycin | − | 3 | 20 |
| [105] Yellow colony | − | 1 | 1 |
| [106] Translucent colony | n.t. | 3 | 1 |
| [107] Lipase | n.t. | 21 | 1 |
| [108] Oxidase (10 sec.) | + | 6 | 1 |

Isolate ML005 best identification is Cluster 3. Scores for coefficients: 1 (Willcox probability), 2 (Taxonomic Distance), 3 (Standard Error of Taxonomic Distance).

TABLE 23-continued

Example of the Output from the MATIDEN Program to Identify Six Unknown Strains against the Identification Matrix

|  | 1 | 2 | 3 |
|---|---|---|---|
| Cluster 3 | 0.9999 | 0.407 | 1.475 |
| Cluster 4 | $0.8266 \times 10^{-4}$ | 0.526 | 4.590 |
| Cluster 2 | $0.4086 \times 10^{-7}$ | 0.584 | 6.296 |

| Characters against Cluster 3 | % in Taxon | Value in unknown |  |
|---|---|---|---|
| [108] Oxidase (10 sec.) | 6 | + | |
| Additional characters that assist in separating | Cluster 3 % | from | Cluster 4 % |
| [106] Translucent colony | 3 | | 99 |
| [107] Lipase | 21 | | 99 |

B. Reference Number of unknown is ML104

| Character | Value in unknown | Percent in: Best Taxon | Percent in: Next Best Taxon |
|---|---|---|---|
| [23] N-acetylglucosamine | − | 13 | 1 |
| [26] Saccharose | − | 25 | 1 |
| [27] Maltose | − | 25 | 1 |
| [32] Lactate | − | 38 | 50 |
| [41] Propionate | − | 1 | 99 |
| [43] Valerate | − | 13 | 99 |
| [44] Citrate | − | 13 | 50 |
| [45] Histidine | − | 1 | 1 |
| [47] Glycogen | − | 1 | 13 |
| [51] 3-Hydroxybutyrate | − | 13 | 25 |
| [52] 4-Hydroxybenzoate | − | 1 | 1 |
| [58] Leucine arylamidase | + | 88 | 63 |
| [59] Valine arylamidase | + | 88 | 25 |
| [64] Phosphohydrolase | + | 88 | 13 |
| [65] α-Galactosidase | n.t. | 1 | 1 |
| [85] Ampicillin | − | 50 | 63 |
| [92] Fusidic Acid | − | 25 | 1 |
| [93] Methicillin | − | 50 | 13 |
| [99] Polymix | + | 88 | 50 |
| [102] Vancomycin | − | 13 | 13 |
| [105] Yellow colony | − | 1 | 1 |
| [106] Translucent colony | n.t. | 1 | 99 |
| [107] Lipase | n.t. | 1 | 99 |
| [108] Oxidase (10 sec.) | + | 25 | 88 |

Isolate ML104 best identification is Cluster 1. Scores for coefficients: 1 (Willcox probability), 2 (Taxonomic Distance), 3 (Standard Error of Taxonomic Distance).

|  | 1 | 2 | 3 |
|---|---|---|---|
| Cluster 1 | 0.9999 | 0.271 | −1.108 |
| Cluster 2 | $0.825 \times 10^{-5}$ | 0.473 | 3.797 |
| Cluster 4 | $0.407 \times 10^{-7}$ | 0.534 | 4.767 |

| Characters against Cluster 1 | % in Taxon | Value in unknown |  |
|---|---|---|---|
| (none) | | | |
| Additional characters that assist in separating | Cluster 1 % | from | Cluster 2 % |
| [106] Translucent colony | 1 | | 99 |
| [107] Lipase | 1 | | 99 |
|  | Cluster 1 % | from | Cluster 4 % |
| (none) | | | |

TABLE 23-continued

Example of the Output from the MATIDEN Program to Identify Six Unknown Strains against the Identification Matrix C. Reference Number of unknown is ML201

| | | Percent in: | |
|---|---|---|---|
| Character | Value in unknown | Best Taxon | Next Best Taxon |
| [23] N-acetylglucosamine | − | 1 | 13 |
| [26] Saccharose | − | 25 | 25 |
| [27] Maltose | − | 50 | 25 |
| [32] Lactate | − | 1 | 38 |
| [41] Propionate | − | 1 | 1 |
| [43] Valerate | − | 1 | 13 |
| [44] Citrate | − | 50 | 13 |
| [45] Histidine | − | 1 | 1 |
| [47] Glycogen | − | 25 | 1 |
| [51] 3-Hydroxybutyrate | − | 1 | 13 |
| [52] 4-Hydroxybenzoate | − | 1 | 1 |
| [58] Leucine arylamidase | + | 50 | 88 |
| [59] Valine arylamidase | + | 25 | 88 |
| [64] Phosphohydrolase | + | 75 | 88 |
| [65] α-Galactosidase | n.t. | 75 | 1 |
| [85] Ampicillin | + | 99 | 50 |
| [92] Fusidic Acid | + | 99 | 25 |
| [93] Methicillin | + | 99 | 50 |
| [99] Polymix | − | 1 | 88 |
| [102] Vancomycin | + | 99 | 13 |
| [105] Yellow colony | + | 99 | 1 |
| [106] Translucent colony | n.t. | 1 | 1 |
| [107] Lipase | n.t. | 1 | 1 |
| [108] Oxidase (10 sec.) | − | 1 | 25 |

Isolate ML201 best identification is Cluster 5. Scores for coefficients: 1 (Willcox probability), 2 (Taxonomic Distance), 3 (Standard Error of Taxonomic Distance).

| | 1 | 2 | 3 |
|---|---|---|---|
| Cluster 5 | 0.9999 | 0.267 | −0.176 |
| Cluster 1 | $0.835 \times 10^{-4}$ | 0.437 | 2.435 |
| Cluster 2 | $0.177 \times 10^{-11}$ | 0.641 | 7.593 |

| Characters against Cluster 5 | % in Taxon | Value in unknown |
|---|---|---|
| (none) | | |
| Additional characters that assist in separating | Cluster 5 % | Cluster 1 % |
| [65] α-Galactosidase | 75 | 1 |
| | Cluster 5 % from | Cluster 2 % from |
| [65] α-Galactosidase | 75 | 1 |
| [106] Translucent colony | 1 | 99 |
| [107] Lipase | 1 | 99 |

D. Reference Number of unknown is ML203

| | | Percent in: | |
|---|---|---|---|
| Character | Value in unknown | Best Taxon | Next Best Taxon |
| [23] N-acetylglucosamine | + | 26 | 20 |
| [26] Saccharose | + | 74 | 20 |
| [27] Maltose | + | 68 | 60 |
| [32] Lactate | + | 99 | 99 |
| [41] Propionate | + | 91 | 60 |
| [43] Valerate | + | 97 | 80 |
| [44] Citrate | + | 94 | 20 |
| [45] Histidine | + | 71 | 1 |
| [47] Glycogen | + | 26 | 20 |
| [51] 3-Hydroxybutyrate | + | 94 | 99 |
| [52] 4-Hydroxybenzoate | + | 71 | 80 |
| [58] Leucine arylamidase | + | 94 | 60 |
| [59] Valine arylamidase | + | 65 | 99 |
| [64] Phosphohydrolase | − | 3 | 20 |
| [65] α-Galactosidase | n.t. | 3 | 20 |
| [85] Ampicillin | − | 56 | 1 |
| [92] Fusidic Acid | − | 3 | 20 |
| [93] Methicillin | − | 50 | 1 |
| [99] Polymix | + | 81 | 99 |
| [102] Vancomycin | + | 3 | 20 |
| [105] Yellow colony | − | 1 | 1 |
| [106] Translucent colony | n.t. | 3 | 1 |
| [107] Lipase | n.t. | 21 | 1 |
| [108] Oxidase (10 sec.) | + | 6 | 1 |

Isolate ML203 best identification is Cluster 3. Scores for coefficients: 1 (Willcox probability), 2 (Taxonomic Distance), 3 (Standard Error of Taxonomic Distance).

| | 1 | 2 | 3 |
|---|---|---|---|
| Cluster 3 | 0.9989 | 0.437 | 2.076 |
| Cluster 4 | $0.1090 \times 10^{-2}$ | 0.526 | 4.590 |
| Cluster 2 | $0.8137 \times 10^{-9}$ | 0.650 | 7.793 |

| Characters against Cluster 3 | % in Taxon | Value in unknown |
|---|---|---|
| [102] Vancomycin | 3 | + |
| [108] Oxidase (10 sec.) | 6 | + |
| Additional characters that assist in separating | Cluster 3 % from | Cluster 4 % |
| (none) | | |

E. Reference Number of unknown is ML206

| | | Percent in: | |
|---|---|---|---|
| Character | Value in unknown | Best Taxon | Next Best Taxon |
| [23] N-acetylglucosamine | − | 1 | 13 |
| [26] Saccharose | + | 25 | 25 |
| [27] Maltose | − | 50 | 25 |
| [32] lactate | − | 1 | 38 |
| [41] Propionate | − | 1 | 1 |
| [43] Valerate | − | 1 | 13 |
| [44] Citrate | − | 50 | 13 |
| [45] Histidine | − | 1 | 1 |
| [47] Glycogen | + | 25 | 1 |
| [51] 3-Hydroxybutyrate | − | 1 | 13 |
| [52] 4-Hydroxybenzoate | − | 1 | 1 |
| [58] Leucine arylamidase | + | 50 | 88 |
| [59] Valine arylamidase | + | 25 | 88 |
| [64] Phosphohydrolase | + | 75 | 88 |
| [65] α-Galactosidase | n.t. | 75 | 1 |
| [85] Ampicillin | + | 99 | 50 |
| [92] Fusidic Acid | + | 99 | 25 |
| [93] Methicillin | + | 99 | 50 |
| [99] Polymix | − | 1 | 88 |
| [102] Vancomycin | + | 99 | 13 |
| [105] Yellow colony | + | 99 | 1 |
| [106] Translucent colony | n.t. | 1 | 1 |
| [107] Lipase | n.t. | 1 | 1 |
| [108] (Oxidase 10 sec.) | − | 1 | 25 |

Isolate ML206 best identification is Cluster 5. Scores for coefficients: 1 (Willcox probability), 2 (Taxonomic Distance), 3 (Standard Error of Taxonomic Distance).

| | 1 | 2 | 3 |
|---|---|---|---|
| Cluster 5 | 0.9999 | 0.345 | 1.766 |

TABLE 23-continued

Example of the Output from the MATIDEN Program to Identify
Six Unknown Strains against the Identification Matrix

| Cluster 1 | $0.2530 \times 10^{-5}$ | 0.512 | 4.013 |
|---|---|---|---|
| Cluster 6 | $0.2531 \times 10^{-13}$ | 0.652 | 10.883 |

| Characters against Cluster 5 | % in Taxon | Value in unknown | |
|---|---|---|---|
| (none) | | | |
| Additional characters that assist in separating | Cluster 5 % | from | Cluster 1 % |
| [65] α-Galactosidase | 75 | | 1 |

F. Reference Number of unknown is ML301

| | | Percent in: | |
|---|---|---|---|
| Character | Value in unknown | Best Taxon | Next Best Taxon |
| [23] N-acetylglucosamine | − | 26 | 1 |
| [26] Saccharose | + | 74 | 1 |
| [27] Maltose | + | 68 | 1 |
| [32] Lactate | + | 99 | 50 |
| [41] Propionate | + | 91 | 99 |
| [43] Valerate | + | 97 | 99 |
| [44] Citrate | + | 94 | 50 |
| [45] Histidine | + | 71 | 1 |
| [47] Glycogen | + | 26 | 13 |
| [51] 3-Hydroxybutyrate | + | 94 | 25 |
| [52] 4-Hydroxybenzoate | − | 71 | 1 |
| [58] Leucine arylamidase | + | 94 | 63 |
| [59] Valine arylamidase | + | 65 | 25 |
| [64] Phosphohydrolase | − | 3 | 13 |
| [65] α-Galactosidase | n.t. | 3 | 1 |
| [85] Ampicillin | + | 56 | 63 |
| [92] Fusidic Acid | − | 3 | 1 |
| [93] Methicillin | + | 50 | 13 |
| [99] Polymix | + | 81 | 50 |
| [102] Vancomycin | − | 3 | 13 |
| [105] Yellow colony | − | 1 | 1 |
| [106] Translucent colony | n.t. | 3 | 99 |
| [107] Lipase | n.t. | 21 | 99 |
| [108] Oxidase (10 sec.) | + | 6 | 88 |

Isolate ML301 best identification is Cluster 3. Scores
for coefficients: 1 (Willcox probability), 2 (Taxonomic Distance), 3 (Standard Error of Taxonomic Distance).

| | 1 | 2 | 3 |
|---|---|---|---|
| Cluster 3 | 1.000 | 0.429 | 1.918 |
| Cluster 2 | $0.2841 \times 10^{-6}$ | 0.603 | 6.731 |
| Cluster 4 | $0.9313 \times 10^{-8}$ | 0.623 | 6.704 |

| Characters against Cluster 3 | % in Taxon | Value in unknown | |
|---|---|---|---|
| [108] Oxidase (10 sec.) | 6 | | + |
| Additional characters that assist in separating | Cluster 3 % | from | Cluster 2 % |
| [106] Translucent colony | 3 | | 99 |
| [107] Lipase | 21 | | 99 | n.t. = not tested

EXAMPLE 2

Production of Proteolytic Enzymes

Two alkaliphilic strains (1E.1 and 9B.1) were tested for the production of proteolytic enzyme(s) in 7 different media poised at an alkaline pH. The experiments were carried out in 2 liter shake flasks with a baffle, each of the flasks contained 400 ml of the nutrient media R to X (Appendix A). The flasks were placed in an orbital incubator rotating at 280 revolutions per minute at a constant temperature of 37° C. Samples of culture media were removed from the flasks at intervals of 1, 2, 3, 4, 5, 6 and 8 days for the determination of enzyme content which is expressed in Alkaline Delft Units (ADU—as described in British Patent Specification 1,353,317).

Table 24 presents the maximum enzyme yields and the pH of the cultivation medium at the moment at which the measurement of enzyme levels were made.

TABLE 24

Production of Proteolytic Enzymes

| | STRAIN 1E.1$^{CT}$ | | STRAIN 9B.1 | |
|---|---|---|---|---|
| MEDIUM | ADU/ml | pH of MEDIUM | ADU/ml | pH of MEDIUM |
| R | 100 | 8.2 | 14 | 9.7 |
| S | 140 | 8.5 | 49 | 9.1 |
| T | 111 | 8.7 | 6 | 9.1 |
| U | 6 | 9.7 | 4 | 9.7 |
| V | 51 | 9.5 | 7 | 9.6 |
| W | 94 | 9.2 | 7 | 9.3 |
| X | 100 | 9.6 | 28 | 9.6 |

The results of the test clearly indicate the presence of proteolytic enzymes, produced by the alkaliphilic bacteria of the present invention, in the culture broth.

Example 3

Wash Performance Test Using Proteolytic Enzymes

Enzyme preparations from the alkaliphilic bacteria were tested in a specially developed mini-wash test using cotton swatches (2.5×2.5 cm) soiled with milk, blood and ink (obtained from EMPA, St. Gallen, Switzerland, and designated EMPA 116). Prior to the wash test the swatches were pretreated with a solution containing an anionic surfactant, sodium perborate and a bleach activator (TAED) at ambient temperature for 15 minutes. After this treatment the test swatches were rinsed in running demineralized water for 10 minutes and air-dried. This treatment results in the fixation of the soil, making its removal more difficult.

The washing tests were performed in 100 ml Erlenmeyer flasks provided with a baffle and containing 30 ml of a defined detergent composition plus 300 ADU protease to be tested. In each flask were placed two pre-treated EMPA 116 test swatches. The flasks were placed in a reciprocal shaking water bath (2 cm stroke) and agitated at 320 revolutions per minute. The tests were carried out at 40° C. for 30 minutes. After washing, the swatches were rinsed in running demineralized water for 10 minutes and air-dried. The reflectance of the test swatches was measured at 680 nm with a Photovolt photometer (Model 577) equipped with a green filter.

The wash performance of the supernatant fraction of cultures of various alkaliphilic bacteria in European powder detergents was determined according to the method specified above. The supernatant fractions were subjected to various treatments so as to produce enzyme-containing preparations.

100 ml Erlenmeyer flasks were charged with powder detergent IEC dissolved in standard tap water of 15° German Hardness so as to give a final concentration of 4 g per liter.

The composition of the powder detergent IEC was as follows:

| Component | wt % |
| --- | --- |
| Linear sodium alkyl benzene sulphonate (mean chain length of alkane chain (C11.5)) | 6.4 |
| Ethoxylated tallow alcohol (14EO) | 2.3 |
| Sodium soap | 2.8 |
| Sodium tripolyphosphate (STPP) | 35.0 |
| Sodium silicate | 6.0 |
| Magnesium silicate | 1.5 |
| Carboxy methyl cellulose | 1.0 |
| Sodium sulphate | 16.8 |
| Sodium perborate tetrahydrate | 18.5 |
| TAED | 1.5 |
| Miscellaneous + water | up to 100 |

Standard tap water is composed of $CaCl_2.2H_2O$, 0.291 g/l; $MgCl.6H_2O$, 0.140 g/l and $NaHCO_3$, 0,210 g/l dissolved in demineralized water.

To each flask, two EMPA 116 swatches were added and sufficient enzyme-containing preparations to give a final activity of 300 ADU. The final volume of the sud was 30 ml. By way of comparison, one flask contained no enzyme preparation, which was replaced with water. The trial was repeated either two or three times. The results are shown in Table 25.

TABLE 25

Application Washing Trials
Performance of Proteolytic Enzyme-Containing
Preparations in a Washing Formulation.

| Preparation from Strain | Average Remission of EMPA 116 Test Swatches | | |
| --- | --- | --- | --- |
| | Trial 1 | Trial 2 | Trial 3 |
| Untreated Culture Supernatant | | | |
| None (control) | 11.4 | 11.8 | 13.0 |
| $1E.1^{CT}$ | 29.2 | 22.2 | 24.7 |
| 9B.1 | 23.7 | 23.9 | 24.2 |
| $17N.1^{CT}$ | | 11.8 | 18.4 |
| 24B.1 | | 17.3 | 16.3 |
| Freeze Dried Supernatant Fraction | | | |
| None (control) | 10.4 | 11.8 | 13.0 |
| $1E.1^{CT}$ | 15.1 | 28.9 | 30.0 |
| 9B.1 | 21.7 | 14.9 | 17.4 |
| $17N.1^{CT}$ | | 13.7 | 17.9 |
| 24B.1 | | 17.8 | 17.3 |
| Dialyzed Supernatant Fractions | | | |
| None (control) | 11.4 | 11.8 | 13.0 |
| $1E.1^{CT}$ | 26.4 | 22.7 | 26.3 |
| 9B.1 | 18.7 | 16.7 | 17.0 |
| $17N.1^{CT}$ | | 12.0 | 12.6 |
| 24B.1 | | 12.6 | 12.4 |
| Ultrafiltration Concentrate of Supernatant Fractions | | | |
| None (control) | 10.4 | 11.4 | |
| $1E.1^{CT}$ | 14.6 | 26.0 | |
| 9B.1 | 15.5 | 16.1 | |
| Acetone Precipitates of Supernatant Fractions | | | |
| None (control) | 10.4 | 11.4 | |
| $1E.1^{CT}$ | 13.4 | 23.4 | |
| 9B.1 | 12.6 | 14.7 | |

The results of the trials demonstrate the efficacy of the proteolytic enzymes produced by the strains of the present invention, provided in various forms, in detergent formulations and the improved washing performance obtained.

EXAMPLE 4

Production of Starch Degrading Enzymes

Strain $1E.1^{CT}$ was tested for the production of starch degrading enzymes on a starch containing medium poised at an alkaline pH.

500 ml Erlenmeyer flasks were charged with 100 ml of alkaline medium (Medium Y, Appendix A) containing 2% soluble starch. The flasks were inoculated (5%) with cells of strain $1E.1^{CT}$ grown for 24 hours on Medium A (37° C.). As controls, similar flasks of alkaline medium not containing starch were also inoculated.

The flasks were placed in an orbital shaking incubator rotating at 280 revolutions per minute, at a constant temperature of 37° C. for 24 hours. The fluid containing the enzyme activity was separated from the cells by centrifugation for 10 minutes at 4000 r.p.m.

The enzyme activity of the supernatant was determined using the reducing sugar assay of Nelson and Somogyi (*Methods in Microbiology*, volume 5B, pp. 300–301; (eds. J. R. Norris and D. W. Ribbons), Academic Press, London, 1971).

Determination of Starch Degrading Enzyme Activity by the Reducing Sugar Assay Solutions Reagent 1

144 g $Na_2SO_4$ is dissolved by gentle warming in 500 ml demineralized water. 12 g potassium sodium tartrate tetrahydrate, 24 g $Na_2CO_3$ and 16 g $NaHCO_3$ are added to the solutions. The total volume of the solution is brought to 800 ml by the addition of demineralized water.

Reagent 2

36 g $Na_2SO_4$ is dissolved by gentle warming in 100 ml demineralized water and 4 g $CuSO_4.5H_2$ is added to the warmed solution. The total volume of the solution is brought to 200 ml by the addition of demineralized water.

Directly before use, Reagents 1 and 2 are mixed in the ratio of 4:1 (Reagent 1: Reagent 2).

Reagent 3

25 g ammonium molybdate tetrahydrate is dissolved in 450 ml demineralized water and 21 ml concentrated sulphuric acid is added with thorough mixing. 3 g $Na_2HAsO_4.7H_2O$ are dissolved in 25 ml demineralized water and this solution is added to the molybdate solution. The total solution is warmed for 48 hours at 37° C. and any precipitate is filtered off.

Standard 100 mg glucose is dissolved in demineralized water and the total volume is brought to 100 ml. Before use, the solution is diluted 10 fold with demineralized water.

Substrate 0.25% soluble starch (Merck, product number 1257) dissolved in 0.1M $Na_2CO_3$-$NaHCO_3$ buffer, pH 10.1.

Assay 0.9 ml starch substrate solution, pH 10.1 is placed in a test-tube. The test-tube is placed in a water bath at 25° C. and allowed to equilibrate. The enzyme reaction is started by adding 0.1 ml of the enzyme-containing culture supernatant. The reaction is allowed to proceed for 30 minutes. The reaction is stopped by adding 1 ml of Reagent ½ and heating for 10 minutes at 100° C. The mixture is cooled on ice for 5 minutes and then 0.5 ml of Reagent 3 is added and the blue color is allowed to develop during 30 minutes at room temperature. The mixture is diluted by adding 1.0 ml demineralized water and the extinction is measured at 500 nm in a spectrophotometer. The reducing sugars are measured as glucose equivalents from a standard curve.

One unit of starch degrading enzyme activity is defined as 1 μg of reducing sugars measured as glucose released per milliliter per minute at pH 10.1 and 25° C.

The number of starch degrading enzyme units formed is shown in Table 26.

TABLE 26

Production of Starch Degrading Enzymes by Strain 1E.1

| MEDIUM | OPTICAL DENSITY at 550 nm | FINAL pH | ENZYME units per liter |
|---|---|---|---|
| plus starch | 2.25 | 9.4 | 1150 |
| no starch | 0.75 | 10.3 | 660 |

The results of the test clearly indicate the presence of starch degrading enzymes, produced by the alkaliphilic bacterial strain of the present invention, in the culture broth.

EXAMPLE 5

Stability of Starch Degrading Enzymes in Detergent

The ability of the starch degrading enzymes from strain $E.1^{CT}$ to withstand detergents, which is essential for their application in laundry detergents or textile desizing, is demonstrated.

100 ml Erlenmeyer flasks provided with a baffle were each charged with 30 ml of 0.1M $Na_2CO_3/NaHCO_3$ buffer, pH 10.1 containing 0.12 g of sodium dodecyl sulphate (equivalent to 4 g per liter). To one half of the flasks 0.3 g potato starch (equivalent to 1%) was added.

Each flask was dosed with enzyme-containing supernatant from strain $1E.1^{CT}$ by adding 0.5, 1.0 or 2.0 ml (see Table 27). As a control, the supernatant fluid was replaced with 1.0 ml water. Immediately after adding the enzyme, a 0.1 ml sample was removed (time=zero hours) for the measurement of enzyme activity.

The flasks were incubated with shaking at 25° C. for 2.5 hours at which time a second 0.1 ml sample was removed for the measurement of enzyme activity.

As a comparison the experiment was repeated using a conventional α-amylase derived from *Bacillus subtilis*.

Enzyme activity was determined using the reducing sugars method previously described.

The results are recorded in Table 27.

TABLE 27

Stability of Starch Degrading Enzymes from Strain $1E.1^{CT}$ in Detergents

| ENZYME-CONTAINING SUPERNATENT ADDED (ml) | CONDI- TIONS | pH | ENZYME UNITS RECOVERED 0 h. | 2.5 h. |
|---|---|---|---|---|
| 0* | SDS | 10.4 | 0 | 0 |
| 0.5 | | 10.3 | 26 | 20 |
| 1.0 | | 10.3 | 44 | 48 |
| 2.0 | | 10.3 | 109 | 113 |
| 0* | SDS + STARCH | 10.3 | 0 | 0 |
| 0.5 | | 10.2 | 12 | 17 |
| 1.0 | | 10.1 | 36 | 48 |
| 2.0 | | 10.2 | 79 | 120 |
| Standard § | SDS | 10.4 | 0 | 0 |
| Standard § | SDS + STARCH | 10.2 | 0 | 0 |

*replaced with 1 ml water?
§ 2.8 RAU *Bacillus subtilis* α-amylase - One RAU (Reference Amylase Unit) is defined as the quantity of enzyme that will convert 1 mg of starch per minute at pH 6.6 and 30° C. into a product which upon reaction with iodine has an equal absorbance at 620 nm. as a solution containing 25 g $CoCl_2.6H_2O$, 3.84 g $K_2Cr_2O_7$ and 1 ml 1M HCl in 100 ml distilled water.

The results of this test clearly demonstrate the stability of the starch degrading enzymes, produced by the alkaliphilic bacterial strain of the present invention, in the presence of detergent.

EXAMPLE 6

Production of Lipolytic Enzymes

Eleven of the new strains which clearly exhibited lipase activity (Appendix D) were tested further for the production of lipolytic enzymes. The eleven strains are examples from Cluster 2 and Cluster 3 (FIG. 1).

The experiments were carried out in 100 ml conical flasks containing 30 ml sterile alkaline nutrient medium, pH 9.6, inoculated with the appropriate bacterial strain. Three different media were used, designated medium Z to BB (Appendix A). The flasks were placed in an orbital shaking incubator (300 rpm) at 30° C. for 48 hours.

The cells were separated from the culture broth by centrifugation and the supernatant dialyzed against 50 volumes 0.1 mM Tris-HCl buffer pH 9, with 3 changes of buffer over 24 hours. The dialysate was freeze dried to give a lipase preparation (Table 28).

The lipase preparations obtained according to this example were used for the washing test described in Example b 7, below.

TABLE 28

Production of Lipase

| STRAIN | PRODUCTION MEDIUM | LIPASE TLU/ml* | LIPASE TLU/g |
|---|---|---|---|
| 39E.3 | BB | 1.3 | 134 |
| 40E.3 | Z | 1.2 | 118 |
| 41E.3 | Z | 1.1 | 82 |
| 42E.3 | Z | 1.2 | 76 |
| 44E.3 | Z | 1.2 | 99 |
| $45E.3^{CT}$ | AA | 1.4 | 98 |
| 48E.3 | BB | 2.0 | 152 |
| 49N.3 | BB | 1.5 | 123 |
| 50N.3 | BB | 2.0 | 100 |
| 51N.3 | BB | 1.0 | 98 |

TABLE 28-continued

| | Production of Lipase | | |
|---|---|---|---|
| STRAIN | PRODUCTION MEDIUM | LIPASE TLU/ml* | LIPASE TLU/g |
| 52N.3 | BB | 1.2 | 128 |

*TLU = True Lipase Unit as defined in U.S. Pat No. 4,933,287.

The results of this test clearly demonstrate the presence of lipolytic enzymes, produced by alkaliphilic bacteria of the present invention, in the culture broth and in a freeze-dried preparation of the dialyzed culture broth.

EXAMPLE 7

Lipase Washing Test

The lipase preparations from Example 6 were tested for performance under washing conditions in TIDE® powder (1.5 g/l), a detergent product from Procter & Gamble.

The washing test (SLM-test) was carried out as described in U.S. Pat. No. 4,933,287, which is hereby incorporated by reference. As control, a lipase derived from *Pseudomonas alcaligenes* strain M1 (CB3 473.85) as described in U.S. Pat. No. 4,933,287 was used. The results are shown in Table 29.

TABLE 29

Lipase Washing Test
Detergent: TIDE ® (powder), 1.5 g/l
Lipase: 2 TLU/ml
$Ca^{2+}$: $10^{-5}M$ (sodium tripolyphosphate added)
pH: 9.5

| | RECOVERY (%) | |
|---|---|---|
| STRAIN | TRIGLYCERIDES | TOTAL LIPID |
| 39E.3 | 55.3 | 73.4 |
| 40E.3 | 82.0 | 89.9 |
| 41E.3 | 44.7 | 78.7 |
| 42E.3 | 55.5 | 74.8 |
| 44E.3 | 6.6 | 76.9 |
| 45E.3$^{CT}$ | 81.6 | 92.9 |
| 48E.3 | 76.5 | 82.9 |
| 49N.3 | 72.4 | 82.0 |
| 50N.3 | 50.5 | 76.6 |
| 51N.3 | 80.4 | 87.6 |
| 52N.2 | 77.0 | 84.7 |
| M1 | 88.5 | 91.5 |
| control* | 98.7 | 98.7 |

*Standard tap water as defined in U.S. Pat. No. 4,933,287

Appendix A
Media used in the Present Invention

MEDIUM A

| | |
|---|---|
| Glucose | 10.0 gl$^{-1}$ |
| Peptone (Difco: Detroit, MI, USA) | 5.0 gl$^{-1}$ |
| Yeast Extract (Difco) | 5.0 gl$^{-1}$ |
| K$_2$HPO$_4$ | 1.0 gl$^{-1}$ |
| MgSO$_4$.7H$_2$O | 0.2 gl$^{-1}$ |
| NaCl | 40.0 gl$^{-1}$ |
| Na$_2$CO$_3$ | 10.0 gl$^{-1}$ |
| * Agar | 20.0 gl$^{-1}$ |

MEDIUM B

| | |
|---|---|
| Glucose | 10.0 gl$^{-1}$ |
| Peptone (Difco) | 5.0 gl$^{-1}$ |
| Yeast Extract (Difco) | 5.0 gl$^{-1}$ |
| K$_2$HPO$_4$ | 1.0 gl$^{-1}$ |
| MgSO$_4$.7H$_2$O | 0.2 gl$^{-1}$ |
| NaCl | 40.0 gl$^{-1}$ |
| Na$_2$CO$_3$ | 10.0 gl$^{-1}$ |
| Novobiocin | 50.0 mgl$^{-1}$ |
| Agar | 20.0 gl$^{-1}$ |

MEDIUM C

| | |
|---|---|
| Glucose | 10.0 gl$^{-1}$ |
| Peptone (Difco) | 5.0 gl$^{-1}$ |
| Yeast Extract (Difco) | 5.0 gl$^{-1}$ |
| K$_2$HPO$_4$ | 1.0 gl$^{-1}$ |
| MgSO$_4$.7H$_2$O | 0.2 gl$^{-1}$ |
| NaCl | 40.0 gl$^{-1}$ |
| Na$_2$CO$_3$ | 10.0 gl$^{-1}$ |
| Lactalbumin | 10.0 gl$^{-1}$ |
| Agar | 20.0 gl$^{-1}$ |

MEDIUM D

| | |
|---|---|
| Glucose | 10.0 gl$^{-1}$ |
| Peptone (Difco) | 5.0 gl$^{-1}$ |
| Yeast Extract (Difco) | 5.0 gl$^{-1}$ |
| K$_2$HPO$_4$ | 1.0 gl$^{-1}$ |
| MgSO$_4$.7H$_2$O | 0.2 gl$^{-1}$ |
| NaCl | 40.0 gl$^{-1}$ |
| Na$_2$CO$_3$ | 10.0 gl$^{-1}$ |
| Casein | 20.0 gl$^{-1}$ |
| Agar | 20.0 gl$^{-1}$ |

MEDIUM E

| | |
|---|---|
| Soluble Starch | 10.0 gl$^{-1}$ |
| Peptone (Difco) | 5.0 gl$^{-1}$ |
| Yeast Extract (Difco) | 5.0 gl$^{-1}$ |
| K$_2$HPO$_4$ | 1.0 gl$^{-1}$ |
| MgSO$_4$.7H$_2$O | 0.2 gl$^{-1}$ |
| NaCl | 40.0 gl$^{-1}$ |
| Na$_2$CO$_3$ | 10.0 gl$^{-1}$ |
| Lactalbumin | 10.0 gl$^{-1}$ |
| Agar | 20.0 gl$^{-1}$ |

MEDIUM F

| | |
|---|---|
| Soluble Starch | 10.0 gl$^{-1}$ |
| Peptone (Difco) | 5.0 gl$^{-1}$ |
| Yeast Extract (Difco) | 5.0 gl$^{-1}$ |
| K$_2$HPO$_4$ | 1.0 gl$^{-1}$ |
| MgSO$_4$.7H$_2$O | 0.2 gl$^{-1}$ |
| NaCl | 40.0 gl$^{-1}$ |
| Na$_2$CO$_3$ | 10.0 gl$^{-1}$ |
| Casein | 20.0 gl$^{-1}$ |
| Agar | 20.0 gl$^{-1}$ |

MEDIUM G

| | |
|---|---|
| Oxbile (Oxoid: Basingstoke, U.K.) | 10.0 gl$^{-1}$ |
| (NH$_4$)$_2$SO$_4$ | 5.0 gl$^{-1}$ |
| MgSO$_4$.7H$_2$O | 0.2 gl$^{-1}$ |
| Yeast Entract (Difco) | 0.5 gl$^{-1}$ |
| Lactalbumin | 10.0 gl$^{-1}$ |
| Agar | 20.0 gl$^{-1}$ |
| Adjusted to pH 8.5 with 50% Na$_2$CO$_3$ solution | |

MEDIUM H

| | |
|---|---|
| Oxbile (Oxoid) | 10.0 gl$^{-1}$ |
| (NH$_4$)$_2$SO$_4$ | 5.0 gl$^{-1}$ |
| MgSO$_4$.7H$_2$O | 0.2 gl$^{-1}$ |
| Yeast Extract (Difco) | 0.5 gl$^{-1}$ |
| Casein | 20.0 gl$^{-1}$ |
| Agar | 20.0 gl$^{-1}$ |
| Adjusted to pH 8.5 with 50% Na$_2$CO$_3$ solution | |

MEDIUM I

| | |
|---|---|
| Sabouroud Dextrose Agar (Oxoid) | 65.0 gl$^{-1}$ |
| NaCl | 40.0 gl$^{-1}$ |
| Na$_2$CO$_3$ | 20.0 gl$^{-1}$ |
| Cycloheximide | 50.0 mgl$^{-1}$ |
| Penicillin G | 25000 IUl$^{-1}$ |
| Streptomycin | 25 mgl$^{-1}$ |

Appendix A
Media used in the Present Invention

MEDIUM J

| | |
|---|---|
| Bacto Potato Dextrose Agar (Difco) | 39.0 gl$^{-1}$ |
| NaCl | 40.0 gl$^{-1}$ |
| Na$_2$CO$_3$ | 20.0 gl$^{-1}$ |
| Novobiocin | 50.0 mgl$^{-1}$ |

MEDIUM K

| | |
|---|---|
| Bacto Potato Dextrose Agar (Difco) | 39.0 gl$^{-1}$ |
| NaCl | 40.0 gl$^{-1}$ |
| Na$_2$CO$_3$ | 20.0 gl$^{-1}$ |
| Cycloheximide | 50.0 mgl$^{-1}$ |
| Penicillin G | 25000 IUl$^{-1}$ |
| Streptomycin | 25.0 mgl$^{-1}$ |

MEDIUM L

| | |
|---|---|
| Glucose | 0.2 gl$^{-1}$ |
| Peptone (Difco) | 0.1 gl$^{-1}$ |
| Yeast Extract (Difco) | 0.1 gl$^{-1}$ |
| K$_2$HPO$_4$ | 1.0 gl$^{-1}$ |
| MgSO$_4$.7H$_2$O | 0.2 gl$^{-1}$ |
| NaCl | 40.0 gl$^{-1}$ |
| Na$_2$CO$_3$ | 10.0 gl$^{-1}$ |
| Casein | 20.0 gl$^{-1}$ |
| Agar | 20.0 gl$^{-1}$ |

MEDIUM M (pH 9.6)

| | |
|---|---|
| Oxbile (Oxoid) | 2.0 gl$^{-1}$ |
| (NH$_4$)$_2$SO$_4$ | 1.0 gl$^{-1}$ |
| MgSO$_4$.7H$_2$O | 0.04 gl$^{-1}$ |
| Yeast Extract (Difco) | 0.1 gl$^{-1}$ |
| Olive Oil | 10.0 ml l$^{-1}$ |
| Na$_2$CO$_3$ | 6.1 gl$^{-1}$ |
| Agar | 20.0 gl$^{-1}$ |

MEDIUM N (pH 9.6)

| | |
|---|---|
| Oxbile (Oxoid) | 2.0 gl$^{-1}$ |
| (NH$_4$)$_2$SO$_4$ | 1.0 gl$^{-1}$ |
| MgSO$_4$.7H$_2$O | 0.04 gl$^{-1}$ |
| Yeast Extract (Difco) | 0.1 gl$^{-1}$ |
| Olive Oil | 10.0 ml l$^{-1}$ |
| Na$_2$CO$_3$ | 6.1 gl$^{-1}$ |
| Tergitol 7 (Fluka: Buchs, CH) | 500 ppm |
| Agar | 20.0 gl$^{-1}$ |

MEDIUM O (pH 9.6)

| | |
|---|---|
| Oxbile (Oxoid) | 2.0 gl$^{-1}$ |
| (NH$_4$)$_2$SO$_4$ | 1.0 gl$^{-1}$ |
| MgSO$_4$.7H$_2$O | 0.04 gl$^{-1}$ |
| Yeast Extract (Difco) | 0.1 gl$^{-1}$ |
| Olive Oil | 10.0 ml l$^{-1}$ |
| Na$_2$CO$_3$ | 6.1 gl$^{-1}$ |
| NaCl | 40.0 gl$^{-1}$ |
| Agar | 20.0 gl$^{-1}$ |

MEDIUM P (pH 9.6)

| | |
|---|---|
| Oxbile (Oxoid) | 10.0 gl$^{-1}$ |
| (NH$_4$)$_2$SO$_4$ | 5.0 gl$^{-1}$ |
| MgSO$_4$.7H$_2$O | 0.2 gl$^{-1}$ |
| Yeast Extract (Difco) | 0.5 gl$^{-1}$ |
| Olive Oil | 10.0 ml l$^{-1}$ |
| NaCl | 40.0 gl$^{-1}$ |
| Agar | 20.0 gl$^{-1}$ |
| Adjusted to pH 9.6 with 50% Na$_2$CO$_3$ solution | |

MEDIUM Q (pH 9.6)

| | |
|---|---|
| Oxbile (Oxoid) | 10.0 gl$^{-1}$ |
| (NH$_4$)$_2$SO$_4$ | 5.0 gl$^{-1}$ |
| MgSO$_4$.7H$_2$O | 0.2 gl$^{-1}$ |
| Yeast Extract (Difco) | 0.5 gl$^{-1}$ |
| Olive Oil | 10.0 ml l$^{-1}$ |
| Agar | 20.0 gl$^{-1}$ |
| Adjusted to pH 9.6 with 50% Na$_2$CO$_3$ solution | |

MEDIUM R (pH 9.5)

| | |
|---|---|
| Fresh Yeast | 82.5 gl$^{-1}$ |
| Glucose | 3.3 gl$^{-1}$ |
| K$_2$HPO$_4$ | 1.6 gl$^{-1}$ |
| K$_2$CO$_3$ | 0.6 gl$^{-1}$ |
| KHCO$_3$ | 1.76 gl$^{-1}$ |
| CaCl$_2$ | 0.05 gl$^{-1}$ |
| MgSO$_4$.7H$_2$O | 0.05 gl$^{-1}$ |
| FeSO$_4$ | 0.005 gl$^{-1}$ |
| MnSO$_4$ | 0.0066 gl$^{-1}$ |

MEDIUM S

| | |
|---|---|
| Fresh Yeast | 8.25 gl$^{-1}$ |
| Glucose | 1.32 gl$^{-1}$ |
| K$_2$HPO$_4$ | 1.6 gl$^{-1}$ |
| CaCl$_2$ | 0.05 gl$^{-1}$ |
| MgSO$_4$.7H$_2$O | 0.05 gl$^{-1}$ |
| FeSO$_4$ | 0.005 gl$^{-1}$ |
| MnSO$_4$ | 0.0066 gl$^{-1}$ |
| NaCl | 40.0 gl$^{-1}$ |
| Adjusted to pH 10.5 with 40% Na$_2$CO$_3$ solution | |

MEDIUM T (pH 10.1)

| | |
|---|---|
| Glucose | 10.0 gl$^{-1}$ |
| Peptone (Difco) | 5.0 gl$^{-1}$ |
| Yeast Extract (Difco) | 5.0 gl$^{-1}$ |
| K$_2$HPO$_4$ | 1.0 gl$^{-1}$ |
| MgSO$_4$.7H$_2$O | 0.2 gl$^{-1}$ |
| NaCl | 40.0 gl$^{-1}$ |
| Na$_2$CO$_3$ | 10.0 gl$^{-1}$ |

MEDIUM U

| | |
|---|---|
| Oxbile | 10.0 gl$^{-1}$ |
| (NH$_4$)$_2$SO$_4$ | 5.0 gl$^{-1}$ |
| MgSO$_4$.7H$_2$O | 0.2 gl$^{-1}$ |
| Yeast extract (Difco) | 0.5 gl$^{-1}$ |
| Casein | 10.0 gl$^{-1}$ |
| Adjusted to pH 9.8 with 40% Na$_2$CO$_3$ solution | |

MEDIUM V

| | |
|---|---|
| Tryptone Soya Broth (Oxoid) | 30.0 gl$^{-1}$ |
| Adjusted to pH 9.9 with 40% Na$_2$CO$_3$ solution | |

MEDIUM W (pH 10.1)

| | |
|---|---|
| Soluble starch | 10.0 gl$^{-1}$ |
| Peptone (Difco) | 5.0 gl$^{-1}$ |
| Yeast extract (Difco) | 5.0 gl$^{-1}$ |
| KH$_2$PO$_4$ | 1.0 gl$^{-1}$ |
| MgSO$_4$.7H$_2$O | 0.2 gl$^{-1}$ |
| NaCl | 40.0 gl$^{-1}$ |
| Na$_2$CO$_3$ | 10.0 gl$^{-1}$ |

MEDIUM X

| | |
|---|---|
| Skim milk (Difco) | 100.0 gl$^{-1}$ |
| Adjusted to pH 10.8 with 25% Na$_2$CO$_3$ solution | |

MEDIUM Y

| | |
|---|---|
| Yeast Extract (Difco) | 1.0 g |
| KNO$_3$ | 10.0 g |
| KH$_2$PO$_4$ | 1.0 g |
| MgSO$_4$.7H$_2$O | 0.2 g |
| Na$_2$CO$_3$ | 10.0 g |
| NaCl | 40.0 g |
| Soluble starch (Merck) | 20.0 g |
| Demineralised water | 1 liter |

MEDIUM Z

| | |
|---|---|
| Brain Heart Infusion (Difco) | 20.0 g |
| Na$_2$EDTA (Komplexion III, Siegfried AG, Switzerland) | 1.0 g |
| FeSO$_4$.7H$_2$O | 0.006 g |
| MnSO$_4$.H$_2$O | 0.003 g |
| CaCl$_2$.2H$_2$O | 1.0 g |
| MgSO$_4$.7H$_2$O | 0.25 g |
| Tween 80 | 5.0 g |
| Soya oil | 5.0 g |
| Distilled water to 1 liter, pH of medium adjusted to pH 9.6 with 25% Na$_2$CO$_3$ | |

Appendix A
Media used in the Present Invention solution.
MEDIUM AA

| | |
|---|---|
| Yeast Extract (Difco) | 20.0 g |
| $KH_2PO_4$ | 5.0 g |
| $FeSO_4.7H_2O$ | 0.006 g |
| $MnSO_4.H_2O$ | 0.003 g |
| $CaCl_2.2H_2O$ | 1.0 g |
| $MgSO_4.7H_2O$ | 0.25 g |
| Tween 80 | 5.0 g |
| Soya oil | 5.0 g |

Distilled water to 1 liter, pH of medium adjusted to pH 9.6 with 25% $Na_2CO_3$ solution.

MEDIUM BB

| | |
|---|---|
| Brain Heart Infusion (Difco) | 20.0 g |
| $FeSO_4.7H_2O$ | 0.006 g |
| $MnSO_4.H_2O$ | 0.003 g |
| $CaCl_2.2H_2O$ | 1.0 g |
| $MgSO_4.7H_2O$ | 0.25 g |
| Tween 80 | 5.0 g |
| Soya oil | 5.0 g |

Distilled water to 1 liter, pH of medium adjusted to pH 9.6 with 25% $Na_2CO_3$ solution.

* (when required for a solid medium)

Appendix B
Methods for Unit Tests

1. Character numbers 1 to 5
   Colony color, form, elevation, margin, size
   A suspension of bacteria was spread over an alkaline nutrient agar (Medium A) and cultivated at 37° C. Colonies were examined after 48 hours.

2. Character number 6 and 7
   Cell morphology, Gram's strain reaction
   Bacteria cells grown in alkaline nutrient broth (Medium A, without agar) for 24 hours were spun down in a centrifuge and resuspended in a small amount of alkaline nutrient broth and allowed to air-dry on a microscope slide. Or, bacteria were cultivated for 24–48 hours on an alkaline nutrient agar (Medium A) so as to form colonies. Colonies of bacteria were suspended in physiological saline and a few drops allowed to air-dry on a microscope slide. The Gram's staining test was performed using the Dussault modification (Journal of Bacteriology, 70, 484–485, 1955) with safranin as counterstain.

3. Character number 8
   Oxidase reaction
   Filter paper moistened with a 1% aqueous solution of N,N,N',N'-tetramethyl-p-phenylenediamine or oxidase identification discs (bioM´erieux: Charboni´ebres-les-Bains, France) were smeared with a young bacterial culture from alkaline nutrient agar. A purple color within 1 minute was recorded as a positive reaction. *E. coli,* used as a control, did not give a positive reaction within one minute.

4. Character number 9
   Skim milk test
   A minimal medium composed (g/l distilled water) of yeast extract, 1.0; $KNO_3$, 110.0; $K_2HPO_4$, 1.0; $MgSO_4.7H_2O$, 0.2; NaCl, 40.0; $Na_2CO_3$, 10.0; agar, 20.0 was supplemented with 5.0 g/l skim milk powder, sterilised by autoclaving and poured into Petri dishes. Bacteria were inoculated and incubated at 37° C. Areas of clearing around bacterial colonies in an otherwise opaque agar were recorded as a positive reaction. Non-alkaliphilic reference strains were tested in an identical fashion using media of the same composition but without $Na_2CO_3$ so as to give a pH of 6.8–7.0.

5. Character number 10
   Gelatin hydrolysis
   Charcoal-gelatin discs (bioM´erieux) or "chargels" (Oxoid) were incubated at 37° C. in an alkaline nutrient broth (Medium A) together with bacteria. A black sediment indicated a positive reaction.

6. Character number 11
   NaCl tolerance
   Two methods were applied.
   (a) Bacterial strains were cultivated at 37° C. on an alkaline nutrient agar (Medium A) containing 0%, 4%, 8%, 12% or 15% (w/v) NaCl. The agar plates were examined for bacterial growth after 48 hours.
   (b) Bacterial strains were cultivated at 37° C. in an alkaline nutrient broth (Medium A) containing 0%, 4%, 84, 12%, 15% or 25% NaCl. Bacterial growth was monitored by optical density measurements using a Klett meter (green filter) at 0, 12, 24, 48, 72 and 144 hours.

7. Character number 12
   Minimum pH for growth
   Nutrient agar, pH 6.8–7.0 (Medium A without sodium carbonate) was poured into square Petri dishes. A strip of solidified agar was removed from one end and replaced with molten 4% (w/v) agar containing 3.6% (w/v) $Na_2CO_3$ and 0.8% (w/v) NaOH. A pH gradient from pH 10.5 to pH 7 across the plate was allowed to develop overnight. Bacteria were inoculated by streaking along the pH gradient and cultivated at 37° C. for 48 hours. The pH at the point where bacterial growth ceased was measured with a flat head electrode and with "Alkalite" pH strips (Merck: Darmstadt, W. Germany).

8. Character numbers 13–21
   Carbohydrate utilisation
   A minimal medium composed (g/l distilled water) of yeast extract, 1.0; $KNO_3$, 10.0; $K_2HPO_4$, 1.0; $MgSO_4.7H_2O$, 0.2; NaCl, 40.0; $Na_2CO_3$, 10.0; agar, 20.0 was supplemented with 2.0 g/l of the carbohydrate under test and poured into square Petri dishes. Bacteria were inoculated, using a 25 point multi-point inoculator, from 1.0 ml of a bacterial suspension cultivated for 48 hours in an alkaline nutrient broth (Medium A). The agar-plates were incubated at 37° C. for 48 hours. The results were recording by comparing bacterial growth on minimal nutrient medium containing a carbohydrate supplement with growth on a minimal medium without the carbohydrate under test. Non-alkaliphilic reference strains were tested in an identical fashion using media of the same composition but without $Na_2CO_3$ so as to give a pH of 6.8–7.0.

9. Character numbers 22–53
   Growth on carbon substrates
   Use was made of the commercially available test strip ATB 32 GN (API-bioM´erieux: La Balme les Grottes, France). The strips were used according to the manufacturer's instructions but with an addition of 1.0 ml of a solution containing 4% NaCl and 1% $Na_2CO_3$ to the vials of basal medium provided. The strips were incubated at 37° C. for 48 hours. Non-alkaliphilic reference strains were incubated in the standard basal medium.

10. Character numbers 54–72
    Enzymatic activities
    Use was made of the commercially available test strip APIZYM (API-bioM´erieux) which was used according to the manufacturer's instructions, except that the alkaliphilic bacterial cells were suspended in alkaline nutrient broth (Medium A). The strips were incubated at 37° C. for 4 hours.

11. Character numbers 73–82
    Amino acids as carbon and nitrogen source
    The same technique was employed as for tests 14–21 except that $KNO_3$ was omitted from the minimal nutrient medium.

12. Character numbers 83–104
    Antibiotic sensitivity
    A light suspension of bacteria in alkaline nutrient broth was spread on the surface of alkaline nutrient agar (Medium A) and allowed to dry. Commercially available

Appendix B
Methods for Unit Tests antibiotic susceptibility test discs (Oxoid or Mast Laboratories: Merseyside, U.K.) were applied to the agar surface. The bacteria were cultivated at 37° C. for 48 hours. Clear zones around the antibiotic disks indicated sensitivity.

Appendix C
Unit Tests for Analysis by Numerical Taxonomy

| CHARACTER NUMBER | TEST DESCRIPTION | COMPUTER CODE |
|---|---|---|
| 1 | Colony color | white = 1 |
| | | cream = 2 |
| | | beige = 3 |
| | | yellow = 4 |
| | | orange = 5 |
| | | pink = 6 |
| | | brown = 7 |
| | | red = 8 |
| 2 | Colony form | circular = 1 |
| | | irregular = 2 |
| | | punctiform = 3 |
| | | filamentous = 4 |
| 3 | Colony elevation | convex = 1 |
| | | raised = 2 |
| | | umbonate = 3 |
| | | flat = 4 |
| 4 | Colony margin | entire = 1 |
| | | undulate = 2 |
| | | lobate = 3 |
| | | fimbriate = 4 |
| 5 | Colony size | diameter in millimeters |
| 6 | Cell morphology | rod = 1 |
| | | coccus = 2 |
| 7 | Gram's stain | negative = 1 |
| | | positive = 2 |
| 8 | Oxidase test | negative = 1 |
| | | positive = 2 |
| 9 | Skim milk test | negative = 1 |
| | | positive = 2 |
| 10 | Gelatin hydrolysis | negative = 1 |
| | | positive = 2 |
| 11 | NaCl tolerance | growth at 0%–4% = 1 |
| | | growth at 0%–8% = 2 |
| | | growth at 0%–12% = 3 |
| | | growth at 0%–15% = 4 |
| | | growth only at 0% = 5 |
| | | growth only at 4%–15% = 6 |
| 12 | Minimum pH for growth on nutrient agar | pH 7.5 = 7.5 |
| | | pH 8.0 = 8.0 |
| | | pH 8.5 = 8.5 |
| | | pH 9.0 = 9.0 |
| | | pH 9.5 = 9.5 |
| | | pH 10.0 = 10.0 |
| | | pH 10.5 = 10.5 |
| 13–21 | Carbohydrate utilisation | |
| 13 | Formate | |
| 14 | Fumarate | |
| 15 | Succinate | |
| 16 | Galactose | enhanced growth = 2 |
| 17 | Pyruvate | equal growth = 1 |
| 18 | Fructose | growth inhibited = 0 |
| 19 | Lactose | |
| 20 | Xylose | |
| 21 | Starch | |
| 22–53 | Growth on carbon substrates | |
| 22 | Rhamnose | |
| 23 | N-acetylglucosamine | |
| 24 | D-ribose | |
| 25 | Inositol | |
| 26 | D-saccharose | |
| 27 | Maltose | |
| 28 | Itaconate | |
| 29 | Suberate | |
| 30 | Malonate | |
| 31 | Acetate | |
| 32 | DL-lactate | positive = 2 |
| 33 | L-alanine | negative = 1 |
| 34 | Mannitol | |
| 35 | D-glucose | |
| 36 | Salicin | |
| 37 | D-melibiose | |
| 38 | L-fucose | |
| 39 | D-sorbitol | |
| 40 | L-arabinose | |
| 41 | Propionate | |
| 42 | Caprate | |
| 43 | Valerate | |
| 44 | Citrate | |
| 45 | Histidine | |
| 46 | 5-ketogluconate | |
| 47 | Glycogen | |
| 48 | 3-hydroxybenzoate | |
| 49 | L-serine | |
| 50 | 2-ketogluconate | |
| 51 | 3-hydroxybutyrate | |
| 52 | 4-hydroxybenzoate | |
| 53 | L-proline | |
| 54–72 | Enzymatic activities | |
| 54 | Alkaline phosphatase | |
| 55 | Esterase (C4) | |
| 56 | Esterase lipase (C8) | |
| 57 | Lipase (C14) | |
| 58 | Leucine arylamidase | |
| 59 | Valine arylamidase | |
| 60 | Cystine arylamidase | positive = 2 |
| 61 | Trypsin | negative = 1 |
| 62 | Chymotrypsin | |
| 63 | Acid phosphatase | |
| 64 | Naphthol-AS-BI-phosphohydrolase | |
| 65 | α-galactosidase | |
| 66 | β-galactosidase | |
| 67 | β-glucuronidase | |
| 68 | α-glucosidase | |
| 69 | β-glucosidase | |
| 70 | N-acetyl-β-glucosaminidase | |
| 71 | α-mannosidase | |
| 72 | α-fucosidase | |
| 73–82 | Amino acids as carbon and nitrogen source | |
| 73 | Serine | |
| 74 | Proline | |
| 75 | Asparagine | |
| 76 | Arginine | enhanced growth = 2 |
| 77 | Alanine | equal growth = 1 |
| 78 | Lysine | no growth = 0 |
| 79 | Methionine | |
| 80 | Phenylalanine | |
| 81 | Glycine | |
| 82 | Valine | |
| 83–104 | Antibiotic sensitivity | |
| 83 | Gentamycin 10 μg | |
| 84 | Nitrofurantoin 50 μg | |
| 85 | Ampicillin 25 μg | |
| 86 | Nalidixic Acid 30 μg | |
| 87 | Sulphamethoxazole 50 mg | |
| 88 | Trimethoprim 2 · 5 μg | |
| 89 | Penicillin G 1 IU | antibiotic sensitive |

Appendix C
Unit Tests for Analysis by Numerical Taxonomy

| CHARACTER NUMBER | TEST DESCRIPTION | COMPUTER CODE |
|---|---|---|
| 90 | Chloramphenicol 25 μg | inhibition of growth = 2 |
| 91 | Erythromycin 5 μg | |
| 92 | Fusidic Acid 10 μg | antibiotic insensitive, |
| 93 | Methicillin 10 μg | no growth inhibition = 1 |
| 94 | Novobiocin 5 μg | |
| 95 | Streptomycin 10 μg | |
| 96 | Tetracycline 25 μg | |
| 97 | Sulphafurazole 100 μg | |
| 98 | Oleandomycin 5 μg | |
| 99 | Polymixin | 300 IU |
| 100 | Rifampicin | 2 μg |
| 101 | Neomycin | 30 μg |
| 102 | Vancomycin | 30 μg |
| 103 | Kanamycin | 30 μg |
| 104 | Bacitracin | 10 IU |

Appendix D
Screening for Proteolytic, Amylolytic and Lipolytic Activity

Proteolytic Activity

| STRAIN | LACTALBUMIN | CASEIN | BLOOD | GELATIN |
|---|---|---|---|---|
| Cluster 1 | | | | |
| 1E.1$^{CT}$ | + | + | + | + |
| 2E.1 | − | − | − | − |
| wB2 | − | − | − | + |
| wB5 | − | − | − | − |
| wBs4 | − | + | + | + |
| 10B.1 | + | + | + | + |
| 20N.1 | + | + | − | + |
| 27M.1 | − | + | − | − |
| wNk2 | − | + | − | + |
| Cluster 2 | | | | |
| 39E.3 | n.t. | n.t. | n.t. | + |
| 41E.3 | n.t. | n.t. | n.t. | + |
| 45E.3$^{CT}$ | n.t. | n.t. | n.t. | + |
| 47E.3 | n.t. | n.t. | n.t. | + |
| 51N.3 | n.t. | n.t. | n.t. | + |
| 52N.3 | n.t. | n.t. | n.t. | + |
| 42E.3 | n.t. | n.t. | n.t. | + |
| 50N.3 | n.t. | n.t. | n.t. | + |
| Cluster 3 | | | | |
| 6B.1 | + | + | − | + |
| 7B.1 | + | + | − | − |
| 8B.1 | − | + | − | + |
| 38E.2 | n.t. | n.t. | n.t. | − |
| 56E.4 | + | n.t. | n.t. | − |
| 25B.1 | n.t. | + | n.t. | + |
| 26N.1 | − | + | − | + |
| 11C.1 | + | + | − | + |
| wB.1 | − | − | − | + |
| 12C.1 | − | + | − | − |
| 28N.1$^{CT}$ | − | − | − | − |
| 61N.4 | + | n.t. | n.t. | − |
| 36E.2 | n.t. | n.t. | n.t. | − |
| 40E.3 | n.t. | n.t. | n.t. | + |
| 65B.4 | + | n.t. | n.t. | − |
| 94LM.4 | n.t. | n.t. | n.t. | + |
| 19N.1 | − | + | − | + |
| 24B.1 | + | + | − | + |
| 21M.1 | + | + | + | + |
| 29C.1 | − | − | − | − |
| 35E.2 | n.t. | n.t. | n.t. | − |
| 37E.2 | n.t. | n.t. | n.t. | − |
| 48E.3 | n.t. | n.t. | n.t. | + |
| 78LN.4 | n.t. | + | n.t. | + |
| 73aC.4 | n.t. | + | n.t. | + |
| 75C.4 | n.t. | + | n.t. | + |
| 73bC.4 | n.t. | + | n.t. | + |
| 74C.4 | n.t. | + | n.t. | − |
| 77LN.4 | n.t. | + | n.t. | − |
| wN1 | − | − | − | − |
| 49N.3 | n.t. | n.t. | n.t. | + |
| 44E.3 | n.t. | n.t. | n.t. | + |
| 58E.4 | n.t. | n.t. | n.t. | n.t. |
| 57E.4 | + | n.t. | n.t. | + |
| Cluster 4 | | | | |
| wE5 | − | − | − | + |
| wB4$^{CT}$ | − | − | − | − |
| wNk1 | − | − | − | + |
| wEl1 | − | − | − | + |
| wEl2 | − | − | − | + |
| Cluster 5 | | | | |
| 9B.1 | − | + | − | + |
| 16N.1 | + | n.t. | n.t. | + |
| 17N.1$^{CT}$ | + | + | − | + |
| 22M.1 | + | + | − | + |
| Cluster 6 | | | | |
| 18N.1 | + | + | − | + |
| 59E.4 | + | n.t. | n.t. | + |
| 64B.4$^{CT}$ | + | n.t. | n.t. | + |
| 63N.4 | + | n.t. | n.t. | + |
| 53E.4 | + | n.t. | n.t. | + |
| Non-Clustering Strains | | | | |
| wN.2 | − | − | − | + |
| 4E.1 | − | − | − | − |
| 5E.1 | − | − | − | + |
| 92LM.4 | n.t. | n.t. | n.t. | + |
| wBn5 | − | − | − | + |

Amylolytic and Lipolytic Activity*

| STRAIN | STARCH HYDROLYSIS | LIPASE ACTIVITY ON OLIVE OIL | ESTERASE LIPASE ACTIVITY | LIPASE ACTIVITY |
|---|---|---|---|---|
| Cluster 1 | | | | |
| 1E.1$^{CT}$ | + | − | + | + |
| 2E.1 | + | − | + | − |
| wB2 | − | − | + | − |
| wB5 | − | − | + | − |
| wBs4 | − | − | + | − |
| 10B.1 | + | − | + | − |
| 20N.1 | − | − | + | − |
| 27M.1 | − | − | + | − |
| wNk2 | + | − | + | − |
| Cluster 2 | | | | |
| 39E.3 | + | + | + | − |
| 41E.3 | + | + | + | − |
| 45E.3$^{CT}$ | + | + | + | + |
| 47E.3 | + | + | − | − |
| 51E.3 | + | + | + | + |
| 52E.3 | + | + | + | + |
| 42E.3 | + | + | + | + |
| 50N.3 | + | + | + | + |
| Cluster 3 | | | | |
| 6B.1 | − | − | + | − |
| 7B.1 | + | − | + | + |
| 8B.1 | + | − | + | − |
| 38E.2 | − | − | + | − |
| 56E.4 | − | + | + | + |
| 25B.1 | − | − | + | + |

-continued

Appendix D
Screening for Proteolytic, Amylolytic and Lipolytic Activity

| 26N.1 | − | − | + | − |
|---|---|---|---|---|
| 11C.1 | − | − | + | − |
| wB1 | − | − | + | − |
| 12C.1 | + | − | − | − |
| 28N.1[CT] | + | − | + | − |
| 61N.4 | + | − | − | − |
| 36E.2 | − | − | − | − |
| 40E.3 | + | + | + | + |
| 65B.4 | + | − | + | − |
| 94LM.4 | + | − | + | − |
| 19N.1 | + | − | + | + |
| 24B.1 | − | − | + | − |
| 21M.1 | + | − | − | − |
| 29C.1 | + | − | + | + |
| 35E.2 | − | − | + | − |
| 37E.2 | − | − | + | − |
| 48E.3 | − | + | + | − |
| 78LN.4 | − | − | + | − |
| 73aC.4 | − | − | + | − |
| 75C.4 | + | − | − | − |
| 73bC.4 | + | − | + | − |
| 74C.4 | + | − | + | − |
| 77LN.4 | − | − | + | + |
| wN1 | + | − | + | − |
| 49N.3 | + | + | + | − |
| 44E.3 | + | + | + | + |
| 58E.4 | + | + | + | − |
| 57E.4 | + | − | + | − |

Cluster 4

| wE5 | + | − | − | − |
|---|---|---|---|---|
| wB4[CT] | − | − | + | − |
| wNk1 | + | − | + | − |
| wEl1 | − | − | + | − |
| wEl2 | − | − | + | − |

Cluster 5

| 9B.1 | + | − | + | − |
|---|---|---|---|---|
| 16N.1 | + | − | + | − |
| 17N.1[CT] | + | − | + | − |
| 22M.1 | + | − | + | − |

Cluster 6

| 18N.1 | + | − | + | − |
|---|---|---|---|---|
| 59E.4 | + | − | + | − |
| 64B.4[CT] | + | − | + | − |
| 63N.4 | + | − | − | − |
| 53E.4 | + | − | + | − |

Non-Clustering Strains

| wN2 | + | − | + | + |
|---|---|---|---|---|
| 4E.1 | − | − | + | − |
| 5E.1 | + | − | + | − |
| 92LM.4 | + | + | + | − |
| wBn5 | − | − | + | − | n.t. = not tested
*Starch Hydrolysis determined according to Character 21 (Appendix B)
Lipase Activity (Olive Oil) determined on media M-P (Appendix A)
Esterase Lipase Activity determined according to Character 56 (Appendix B)
Lipase Activity determined according to Character 57 (Appendix B)

Appendix E
Percentage Positive States for Characters in Clusters

| CHARACTER | CLUSTER 1 | 2 | 3 | 4 | 5 | 6 |
|---|---|---|---|---|---|---|
| [6] Cell morphology | 9 | 0 | 12 | 0 | 0 | 0 |
| [7] Gram's stain | 0 | 0 | 0 | 0 | 0 | 0 |
| [8] Oxidase test | 55 | 100 | 35 | 80 | 0 | 20 |
| [9] Skim milk test | 36 | 11 | 6 | 20 | 0 | 20 |
| [10] Gelatin | 67 | 100 | 56 | 60 | 100 | 100 |
| [13] Formate | 0 | 0 | 15 | 40 | 0 | 0 |
| [14] Fumarate | 45 | 78 | 74 | 80 | 75 | 60 |
| [15] Succinate | 45 | 89 | 85 | 40 | 67 | 50 |
| [16] Galactose | 45 | 11 | 12 | 40 | 25 | 0 |
| [17] Pyruvate | 64 | 89 | 88 | 40 | 75 | 0 |
| [18] Fructose | 45 | 11 | 68 | 60 | 50 | 100 |
| [19] Lactose | 9 | 0 | 0 | 0 | 0 | 0 |
| [20] Xylose | 18 | 11 | 15 | 20 | 0 | 0 |
| [21] Starch | 73 | 100 | 91 | 20 | 100 | 100 |
| [22] Rhamnose | 9 | 0 | 15 | 20 | 0 | 0 |
| [23] N-acetyl-glucosamine | 9 | 0 | 26 | 20 | 0 | 100 |
| [24] D-ribose | 27 | 0 | 50 | 0 | 0 | 20 |
| [25] Inositol | 9 | 0 | 9 | 0 | 50 | 0 |
| [26] D-saccharose | 27 | 0 | 74 | 20 | 25 | 100 |
| [27] Maltose | 9 | 11 | 74 | 40 | 50 | 100 |
| [28] Itaconate | 0 | 11 | 6 | 0 | 0 | 0 |
| [29] Suberate | 9 | 67 | 53 | 40 | 0 | 0 |
| [30] Malonate | 0 | 11 | 65 | 0 | 25 | 40 |
| [31] Acetate | 18 | 100 | 100 | 80 | 25 | 100 |
| [32] DL-lactate | 27 | 56 | 100 | 100 | 0 | 40 |
| [33] L-alanine | 18 | 89 | 82 | 100 | 0 | 100 |
| [34] Mannitol | 0 | 0 | 41 | 20 | 0 | 80 |
| [35] D-glucose | 9 | 11 | 71 | 60 | 0 | 60 |
| [36] Salicin | 0 | 0 | 3 | 20 | 0 | 60 |
| [37] D-melibiose | 0 | 0 | 3 | 0 | 0 | 0 |
| [38] L-fucose | 0 | 0 | 0 | 20 | 0 | 20 |
| [39] D-sorbitol | 18 | 0 | 41 | 0 | 0 | 40 |
| [40] L-arabinose | 9 | 0 | 3 | 40 | 0 | 0 |
| [41] Propionate | 9 | 100 | 94 | 80 | 0 | 80 |
| [42] Caprate | 0 | 78 | 32 | 40 | 0 | 80 |
| [43] Valerate | 9 | 100 | 97 | 80 | 0 | 40 |
| [44] Citrate | 9 | 56 | 94 | 20 | 50 | 100 |
| [45] Histidine | 0 | 0 | 71 | 0 | 0 | 80 |
| [46] 5-ketogluconate | 0 | 0 | 21 | 0 | 0 | 0 |
| [47] Glycogen | 9 | 22 | 26 | 20 | 25 | 100 |
| [48] 3-hydroxybenzoate | 9 | 0 | 38 | 0 | 0 | 0 |
| [49] L-serine | 0 | 0 | 68 | 60 | 0 | 0 |
| [50] 2-ketogluconate | 0 | 0 | 56 | 80 | 25 | 20 |
| [51] 3-hydroxybutyrate | 18 | 33 | 94 | 100 | 0 | 100 |
| [52] 4-hydroxybenzoate | 0 | 0 | 71 | 80 | 0 | 100 |
| [53] L-proline | 45 | 100 | 100 | 80 | 25 | 80 |
| [54] Alkaline phosphatase | 100 | 44 | 94 | 40 | 100 | 60 |
| [55] Esterase (C4) | 100 | 100 | 100 | 100 | 100 | 100 |
| [56] Esterase lipase (C8) | 100 | 89 | 85 | 100 | 100 | 100 |
| [57] Lipase (C14) | 9 | 67 | 26 | 0 | 0 | 0 |
| [58] Leucine arylamidase | 91 | 67 | 94 | 60 | 50 | 0 |
| [59] Valine arylamidase | 91 | 33 | 65 | 100 | 25 | 0 |
| [60] Cystine arylamidase | 73 | 0 | 15 | 0 | 0 | 0 |
| [61] Trypsin | 64 | 11 | 9 | 60 | 0 | 0 |
| [62] Chymotrypsin | 73 | 0 | 3 | 20 | 75 | 0 |
| [63] Acid phosphatase | 91 | 11 | 94 | 100 | 100 | 60 |
| [64] Naphthol phosphohydrolase | 91 | 22 | 3 | 20 | 100 | 40 |
| [65] α-galactosidase | 0 | 11 | 3 | 20 | 100 | 0 |
| [66] β-galactosidase | 9 | 0 | 0 | 20 | 100 | 0 |
| [67] β-glucuronidase | 9 | 0 | 3 | 20 | 25 | 0 |
| [68] α-glucosidase | 27 | 0 | 79 | 60 | 100 | 40 |
| [69] β-glucosidase | 9 | 0 | 9 | 80 | 75 | 0 |
| [70] N-acetyl-β-glucosaminidase | 27 | 0 | 0 | 0 | 0 | 0 |
| [71] α-mannosidase | 0 | 0 | 0 | 0 | 0 | 0 |
| [72] α-fucosidase | 9 | 0 | 0 | 20 | 0 | 0 |
| [73] Serine | 22 | 13 | 29 | 60 | 100 | 50 |
| [74] Proline | 56 | 63 | 65 | 80 | 100 | 100 |
| [75] Asparagine | 67 | 38 | 61 | 60 | 75 | 100 |
| [76] Arginine | 56 | 25 | 53 | 80 | 50 | 50 |
| [77] Alanine | 67 | 100 | 62 | 40 | 100 | 50 |
| [78] Lysine | 44 | 75 | 71 | 80 | 75 | 100 |
| [79] Methionine | 60 | 50 | 53 | nc | 50 | 50 |

-continued

Appendix E
Percentage Positive States for Characters in Clusters

| CHARACTER | CLUSTER | | | | | |
|---|---|---|---|---|---|---|
| | 1 | 2 | 3 | 4 | 5 | 6 |
| [80] Phenylalanine | 89 | 100 | 76 | 100 | 100 | 100 |
| [81] Glycine | 44 | 13 | 29 | 80 | 50 | 50 |
| [82] Valine | 44 | 50 | 41 | 0 | 50 | 25 |
| [83] Gentamycin | 36 | 67 | 3 | 20 | 0 | 0 |
| [84] Nitrofurantoin | 18 | 33 | 21 | 0 | 0 | 0 |
| [85] Ampicillin | 45 | 67 | 56 | 0 | 100 | 80 |
| [86] Nalidixic Acid | 36 | 78 | 76 | 0 | 0 | 20 |
| [87] Sulphamethoxazole | 18 | 33 | 38 | 0 | 0 | 0 |
| [88] Trimethoprim | 45 | 22 | 35 | 0 | 75 | 60 |
| [89] Penicillin G | 27 | 11 | 29 | 0 | 75 | 100 |
| [90] Chloramphenicol | 100 | 100 | 100 | 100 | 100 | 100 |
| [91] Erythromycin | 91 | 100 | 100 | 100 | 100 | 100 |
| [92] Fusidic Acid | 18 | 0 | 3 | 20 | 100 | 100 |
| [93] Methicillin | 45 | 11 | 50 | 0 | 100 | 100 |
| [94] Novobiocin | 18 | 0 | 3 | 0 | 25 | 0 |
| [95] Streptomycin | 100 | 78 | 97 | 100 | 75 | 100 |
| [96] Tetracycline | 45 | 22 | 3 | 20 | 100 | 100 |
| [97] Sulphafurazole | 40 | 13 | 20 | nc | 0 | 0 |
| [98] Oleandomycin | 100 | 38 | 94 | 100 | 100 | 100 |
| [99] Polymixin | 89 | 63 | 78 | 100 | 0 | 0 |
| [100] Rifampicin | 100 | 38 | 78 | 100 | 100 | 100 |
| [101] Neomycin | 0 | 13 | 0 | 0 | 0 | 0 |
| [102] Vancomycin | 22 | 13 | 0 | 20 | 100 | 75 |
| [103] Kanamycin | 11 | 13 | 0 | 0 | 0 | 0 |
| [104] Bacitracin | 33 | 13 | 0 | 20 | 100 | 100 |

We claim:

1. A pure bacterial culture useful for production of alkali-tolerant enzymes wherein the bacteria consist of aerobic, Gram-negative, rod-shaped, obligate alkaliphilic bacteria having the following characteristics:
 a) forms cream-colored, circular colonies;
 b) grows optimally between pH 9 and pH 10;
 c) gives a positive response to the following tests:
  1) Leucine arylamidase
  2) Valine arylamidase
  3) Phosphohydrolase
  4) Polymixin;
 d) gives a negative response to the following tests:
  1) N-acetylglucosamine
  2) Maltose
  3) Propionate
  4) Caprate
  5) Valerate
  6) Citrate
  7) Histidine
  8) Glycogen
  9) 4-hydroxybenzoate
  10) α-galactosidase.

2. A pure bacterial culture useful for production of alkali-tolerant enzymes wherein the bacteria consist of aerobic, Gram-negative, rod-shaped, obligate alkaliphilic bacteria having the following characteristics:
 a) forms small, cream-colored colonies;
 b) grows optimally between pH 7.8 and pH 11.2;
 c) gives a positive response to the following tests:
  1) Starch
  2) Acetate
  3) Propionate
  4) Valerate
  5) Proline
  6) Lipase
  7) Oxidase (response within 10 seconds);
 d) gives a negative response to the following tests:
  1) N-acetylglucosamine
  2) Saccharose
  3) Histidine
  4) 2-ketogluconate
  5) 4-hydroxybenzoate
  6) α-glucosidase
  7) β-glucosidase
  8) Fusidic Acid.

3. A pure bacterial culture useful for production of alkali-tolerant enzymes wherein the bacteria consist of aerobic, Gram-negative, rod-shaped, obligate alkaliphilic bacteria having the following characteristics:
 a) forms cream-colored, opaque colonies;
 b) grows optimally between pH 8.5 and pH 10.7;
 c) contains ubiquinone 6 as a major respiratory quinone;
 d) gives a positive response to the following tests:
  1) Acetate
  2) Lactate
  3) Propionate
  4) Valerate
  5) Citrate
  6) 3-hydroxybenzoate
  7) Proline
  8) Leucine arylamidase;
 e) gives a negative response to the following tests:
  1) Phosphohydrolase
  2) α-galactosidase
  3) Fusidic Acid
  4) Tetracyclinee
  5) Vancomycin
  6) Bacitracin.

4. A pure bacterial culture useful for production of alkali-tolerant enzymes wherein the bacteria consist of aerobic, Gram-negative, rod-shaped, obligate alkaliphilic bacteria having the following characteristics:
 a) forms beige to brown-colored, opaque colonies;
 b) grows optimally between pH 7.5 and pH 10.9;
 c) contains ubiquinone 9 as a major respiratory quinone;
 d) gives a positive response to the following tests:
  1) Lactate
  2) Alanine
  3) 3-hydroxybutyrate
  4) Valine arylamidase
  5) Polymixin;
 e) gives a negative response to the following tests:
  1) Histidine
  2) Ampicillin
  3) Naladixic acid
  4) Trimethoprim
  5) Penicillin G
  6) Methicillin.

5. A pure bacterial culture useful for production of alkali-tolerant enzymes wherein the bacteria consist of aerobic, Gram-negative, rod-shaped, obligate alkaliphilic bacteria having the following characteristics:
 a) forms bright yellow-colored colonies;
 b) grows optimally between pH 8 and pH 10.5;
 c) gives a positive response to the following tests:
  1) Phosphohydrolase
  2) α-galactosidase
  3) β-galactosidase
  4) Ampicillin
  5) Fusidic Acid
  6) Methicillin 7) Tetracyclinee
8) Vancomycin
9) Bacitracin;

d) gives a negative response to the following tests:
1) N-acetylglucosamine
2) Lactate
3) L-alanine
4) Mannitol
5) Propionate
6) Caprate
7) Valerate
8) Histidine
9) 3-hydroxybenzoate
10) 3-hydroxybutyrate
11) 4-hydroxybenzoate
12) Polymixin.

6. A pure bacterial culture useful for production of alkali-tolerant enzymes wherein the bacteria consist of aerobic, Gram-negative, rod-shaped, obligate alkaliphilic bacteria having the following characteristics:

a) forms cream to beige-colored, irregular, flat colonies;

b) grows optimally between pH 8.2 and pH 10.9;

c) gives a positive response to the following tests:
1) Starch
2) N-acetylglucosamine
3) Saccharose
4) Maltose
5) Acetate
6) Alanine
7) Citrate
8) Glycogen
9) 3-hydroxybutyrate
10) Penicillin G
11) Fusidic Acid
12) Methicillin
13) Tetracyclinee
14) Bacitracin;

d) gives a negative response to the following tests:
1) Pyruvate
2) 4-hydroxybenzoate
3) Leucine arylamidase
4) Valine arylamidase
5) α-galactosidase
6) Polymixin.

7. A pure bacterial culture useful for production of alkali-tolerant enzymes wherein the bacteria consist of aerobic, Gram-negative, motile, rod-shaped, obligate alkaliphilic bacteria having the following characteristics:

a) cells frequently in pairs;

b) grows optimally between pH 9 and pH 10;

c) on alkaline-agar, forms smooth, translucent, beige colored colonies, 1–2 mm in diameter which are circular, convex with an entire margin;

d) in alkaline-broth, growth (37° C.) is flocculent with a ring or surface pellicle and formation of a sediment;

e) grows optimally at 20° C. to 30° C.;

f) no growth at 15° C. or 40° C.;

g) KOH test is positive;

h) aminopeptidase test is weak positive;

i) oxidase test is weak positive;

j) catalase test is positive;

k) obligate halophile;

l) grows optimally at 4% NaCl;

m) no growth at 0% or 8% NaCl;

n) hydrolysis of gelatin test is slow positive;

o) hydrolysis of starch is positive;

p) does not grow on simple sugars;

q) does not grow on organic acids;

r) grows on yeast extract and peptones.

8. A pure bacterial culture useful for production of alkali-tolerant enzymes wherein the bacteria consist of aerobic, Gram-negative, motile, rod-shaped, obligate alkaliphilic bacteria having the following characteristics:

a) grows optimally between pH 8.2 and pH 10.9;

b) on alkaline-agar, forms smooth, opaque, beige or brown colored colonies, 2–4 mm in diameter which are circular in form, convex in elevation, with an entire margin;

c) in alkaline-broth, growth (37° C.) is heavy and flocculent with a sediment and surface pellicle;

d) grows optimally between 20° C. and 37° C.;

e) no growth at 8° C. or at 40° C. or above;

f) KOH test is positive;

g) aminopeptidase test is positive;

h) oxidase test is very weakly positive;

i) catalase test is positive;

j) grows at a NaCl concentration of between 0% and 15%;

k) no growth at 20% NaCl;

l) hydrolysis of gelatin test is negative;

m) hydrolysis of starch is negative;

n) grows on yeast extract;

o) grows on organic acids selected from the group consisting of succinate, pyruvate, citrate, malonate, acetate and lactate;

p) grows on fatty acids selected from the group consisting of propionate, valerate and suberate;

q) grows on amino acids selected from the group consisting of proline, serine, histidine and lysine.

9. A pure bacterial culture useful for production of alkali-tolerant enzymes wherein the bacteria consist of aerobic, Gram-negative, rod-shaped, obligate alkaliphilic bacteria having the following characteristics:

a) grows optimally between pH 9 and pH 10.5;

b) on alkaline-agar, forms smooth, opaque, brown-colored colonies, 3–4 mm in diameter which are fairly irregular in form, generally flat to slightly umbonate in elevation with a lobate margin;

c) in alkaline-broth, growth (37° C.) is moderate to heavy, becoming flocculent with a sediment and surface pellicle;

d) grows optimally between 20° C. and 40° C.;

e) no growth at 45° C.;

f) KOH test is positive;

g) aminopeptidase test is positive;

h) oxidase test is negative;

i) catalase test is positive;

j) grows at a NaCl concentration 0% to 12%;

k) no growth at 20% NaCl;

l) hydrolysis of gelatin test is positive;

m) hydrolysis of starch is weakly positive;

n) does not grow on simple sugars;

o) grows on yeast extract;

p) grows on organic acids selected from the group consisting of pyruvate, citrate, acetate and lactate;

q) grows on fatty acids selected from the group consisting of propionate, caprate and valerate;
r) grows on amino acids selected from the group consisting of proline, alanine and lysine.

10. A pure bacterial culture useful for production of alkali-tolerant enzymes wherein the bacteria consist of aerobic, Gram-negative, rod-shaped, obligate alkaliphilic bacteria having the following characteristics:
a) does not grow below pH 7.5;
b) on alkaline-agar, forms smooth, cream colored colonies, initially translucent but becoming opaque;
c) on alkaline-agar, the colonies develop from circular, entire and become irregular, lobate in form, with a convex elevation; d) in alkaline-broth, growth (37° C.) is slow, slight, flocculent with a sediment but no surface pellicle;
e) grows optimally between 10° C. and 40° C.;
f) no growth at 8° C. or 45° C.;
g) KOH test is positive;
h) aminopeptidase test is negative;
i) oxidase test is positive;
j) catalase test is positive;
k) grows at an NaCl contration of between 0% to 15%;
l) no growth at 20% NaCl;
m) hydrolysis of gelatin test is positive;
n) hydrolysis of starch is weakly positive;
o) grows on yeast extract and peptones;
p) grows on sugars;
q) grows on organic acids;
r) grows on amino acids.

11. A pure bacterial culture useful for production of alkali-tolerant enzymes wherein the bacteria consist of aerobic, Gram-negative, small, rod-shaped, obligate alkaliphilic bacteria having the following characteristics:
a) cells frequently form short chains;
b) does not grow below pH 8;
c) on alkaline-agar, forms smooth, circular, convex colonies with an entire margin, about 1 mm in diameter which are initially transparent, cream/beige in color, the colonies become opaque and brown in color with age;
d) in alkaline-broth, growth (37° C.) is initially evenly turbid with a sediment but no surface pellicle becoming flocculent with formation of a pellicle;
e) grows optimally between 30° C. and 37° C.;
f) no growth at 40° C.;
g) KOH test is positive;
h) aminopeptidase test is positive;
i) oxidase test is positive;
j) catalase test is positive;
k) obligate halophile;
l) grows at 4% NaCl;
m) no growth at 0% or 8% NaCl;
n) hydrolysis of gelatin test is slow positive;
o) hydrolysis of starch is negative;
p) grows on yeast extract and peptones;
q) grows on sugars;
r) grows on organic acids;
s) grows on fatty acids;
t) grows on amino acids.

12. A single strain of bacteria which is useful for the production of alkali-tolerant enzymes, wherein said strain is aerobic, Gram-negative, and rod-shaped, and is an obligate alkaliphile, forms cream-colored circular colonies, grows optimally between pH 9 and pH 10 and is classified at a 73% similarity level into a phenon based on a positive response to the following tests:
(1) leucine arylamidase
(2) Valine arylamidase
(3) Phosphohydrolase
(4) Polymyxin;
and on a negative response in the following tests:
(1) N-acetylglucosamine
(2) Maltose
(3) Propionate
(4) Caprate
(5) Valerate
(6) Citrate
(7) Histidine
(8) Glycogen
(9) 4-hydroxybenzoate
(10) $\alpha$-galactosidase.

13. A single strain of bacteria which is useful for the production of alkali-tolerant enzymes, wherein said strain is aerobic, Gram-negative, and rod-shaped, and is an obligate alkaliphile, forms cream-colored circular colonies, grows optimally between pH 9 and pH 10 and is classified at a 73% similarity level into a phenon based on the pattern of responses to tests leaving a probability matrix with a percentage distribution as follows:
(1) N-acetylglucosamine—13
(2) Saccharose—25
(3) Maltose—25
(4) Lactate—38
(5) Propionate—0
(6) Valerate—13
(7) Citrate—13
(8) Histidine—0
(9) Glycogen—0
(10) 3-hydroxybutyrate—13
(11) 4-hydroxybenzoate—0
(12) Leucine arylamidase—88
(13) Valine arylamidase—88
(14) Phosphohydrolase—88
(15) $\alpha$-galactosidase—0
(16) Ampicillin—50
(17) Fusidic Acid—b 25
(18) Methicillin—50
(19) Polymyxin—88
(20) Vancomycin—13
(21) Yellow colony—0
(22) Translucent colony—0
(23) Lipase—0
(24) Oxidase (10 seconds)—25.

14. A single strain of bacteria which is useful for the production of alkali-tolerant enzymes, wherein said strain is aerobic, Gram-negative, and rod-shaped, and is an obligate alkaliphile, forms small cream-colored colonies, grows optimally between pH 7.8 and pH 11.2 and is classified at a 73% similarity level into a phenon based on A. a positive response to the following tests:
   (1) Starch
   (2) Acetate
   (3) Propionate
   (4) Valerate
   (5) Proline
   (6) Lipase
   (7) Oxidase (response within 10 seconds ); and
B. a negative response in the following tests:
   (1) N-acetylglucosamine
   (2) Saccharose
   (3) Histidine
   (4) 2-ketogluconate
   (5) 4-hydroxybenzoate
   (6) α-glucosidase
   (7) β-glucosidase
   (8) Fusidic Acid.

15. A single strain of bacteria which is useful for the production of alkali-tolerant enzymes, wherein said strain is aerobic, Gram-negative, and rod-shaped, and is an obligate alkaliphile, forms small cream-colored colonies, grows optimally between pH 7.8 and pH 11.2 and is classified at a 73% similarity level into a phenon based on the pattern of responses to tests leaving a probability matrix with a percentage distribution as follows:
   (1) N-acetylglucosamine—0
   (2) Saccharose—0
   (3) Maltose—0
   (4) Lactate—50
   (5) Propionate—100
   (6) Valerate—100
   (7) Citrate—50
   (8) Histidine—0
   (9) Glycogen—13
   (10) 3-hydroxybutyrate—25
   (11) 4-hydroxybenzoate—0
   (12) Leucine arylamidase—63
   (13) Valine arylamidase—25
   (14) Phosphohydrolase—13
   (15) α-galactosidase-0
   (16) Ampicillin-63
   (17) Fusidic Acid—0
   (18) Methicillin—13
   (19) Polymyxin—50
   (20) Vancomycin—13
   (21) Yellow colony—0
   (22) Translucent colony—100
   (23) Lipase—100
   (24) Oxidase (10 seconds)—88.

16. A single strain of bacteria which is useful for the production of alkali-tolerant enzymes, wherein said strain is aerobic, Gram-negative, and rod-shaped, and is an obligate alkaliphile, forms cream-colored, opaque colonies, grows optimally between pH 8.5 and pH 10.7, contains ubiquinone 6 as a major respiratory quinone, and is classified at a 73% similarity level into a phenon based on
A. a positive response to the following tests:
   (1) Acetate
   (2) Lactate
   (3) Propionate
   (4) Valerate
   (5) Citrate
   (6) 3-hydroxybenzoate
   (7) Proline
   (8) Leucine arylamidase;
B. a negative response in the following tests:
   (1) Phosphohydrolase
   (2) α-galactosidase
   (3) Fusidic Acid
   (4) Tetracycline
   (5) Vancomycin
   (6) Bacitracin.

17. A single strain of bacteria which is useful for the production of alkali-tolerant enzymes, wherein said strain is aerobic, Gram-negative, and rod-shaped, and is an obligate alkaliphile, forms cream-colored opaque colonies, grows optimally between pH 8.5 and pH 10.7, contains ubiquinone 6 as a major respiratory quinone, and is classified at a 73% similarity level into a phenon based on the pattern of responses to tests leaving a probability matrix with a percentage distribution as follows:
   (1) N-acetylglucosamine—26
   (2) Saccharose—74
   (3) Maltose—68
   (4) Lactate—100
   (5) Propionate—91
   (6) Valerate—97
   (7) Citrate—94
   (8) Histidine—71
   (9) Glycogen—26
   (10) 3-hydroxybutyrate—94
   (11) 4-hydroxybenzoate—71
   (12) Leucine arylamidase—94
   (13) Valine arylamidase—65
   (14) Phosphohydrolase—3
   (15) α-galactosidase-3
   (16) Ampicillin—56
   (17) Fusidic Acid—3
   (18) Methicillin—50
   (19) Polymyxin—81
   (20) Vancomycin—3
   (21) Yellow colony—0
   (22) Translucent colony—3
   (23) Lipase—21
   (24) Oxidase (10 seconds)—6.

18. A single strain of bacteria which is useful for the production of alkali-tolerant enzymes, wherein said strain is aerobic, Gram-negative, and rod-shaped, and is an obligate alkaliphile, forms beige to brown-colored, opaque colonies, grows optimally between pH 7.5 and pH 10.9, contains ubiquinone 9 as a major respiratory quinone, and is classified at a 73% similarity level into a phenon based on
A. a positive response to the following tests:
   (1) Lactate
   (2) Alanine
   (3) 3-hydroxybutyrate
   (4) Valine arylamidase
   (5) Polymyxin;
B. a negative response in the following tests:
   (1) Histidine
   (2) Ampicillin
   (3) Nalidixic acid
   (4) Trimethoprim
   (5) Penicillin G (6) Methicillin.

19. A single strain of bacteria which is useful for the production of alkali-tolerant enzymes, wherein said strain is aerobic, Gram-negative, and rod-shaped, and is an obligate alkaliphile, forms beige to brown-colored, opaque colonies, grows optimally between pH 7.5 and pH 10.9, contains ubiquinone 9 as a major respiratory quinone, and is classified at a 73% similarity level into a phenon based on the pattern of responses to tests leaving a probability matrix with a percentage distribution as follows:

(1) N-acetylglucosamine—20
(2) Saccharose—20
(3) Maltose—60
(4) Lactate—100
(5) Propionate—60
(6) Valerate—80
(7) Citrate—20
(8) Histidine—0
(9) Glycogen—20
(10) 3-hydroxybutyrate—100
(11) 4-hydroxybenzoate—80
(12) Leucine arylamidase—60
(13) Valine arylamidase—100
(14) Phosphohydrolase—20
(15) α-galactosidase—20
(16) Ampicillin—0
(17) Fusidic Acid—20
(18) Methicillin—0
(19) Polymyxin—100
(20) Vancomycin—20
(21) Yellow colony—0
(22) Translucent colony—0
(23) Lipase—0
(24) Oxidase (10 seconds)—0.

20. A single strain of bacteria which is useful for the production of alkali-tolerant enzymes, wherein said strain is aerobic, Gram-negative, and rod-shaped, and is an obligate alkaliphile, forms bright yellow-colored colonies, grows optimally between pH 8 and pH 10.5, and is classified at a 73% similarity level into a phenon based on A. a positive response to the following tests:
  (1) Phosphohydrolase
  (2) α-galactosidase
  (3) β-galactosidase
  (4) Ampicillin
  (5) Fusidic Acid
  (6) Methicillin
  (7) Tetracycline
  (8) Vancomycin
  (9) Bacitracin;
B. a negative response in the following tests:
  (1) N-acetylglucosamine
  (2) Lactate
  (3) L-alanine
  (4) Mannitol
  (5) Propionate
  (6) Caprate
  (7) Valerate
  (8) Histidine
  (9) 3-hydroxybenzoate
  (10) 3- hydroxybutyrate
  (11) 4-hydroxybenzoate
  (12) Polymyxin.

21. A single strain of bacteria which is useful for the production of alkali-tolerant enzymes, wherein said strain is aerobic, Gram-negative, and rod-shaped, and is an obligate alkaliphile, forms bright yellow-colored colonies, grows optimally between pH 8 and pH 10.5, and is classified at a 73% similarity level into a phenon based on the pattern of responses to tests leaving a probability matrix with a percentage distribution as follows:

(1) N-acetylglucosamine—0
(2) Saccharose—25
(3) Maltose—30
(4) Lactate—0
(5) Propionate—0
(6) Valerate—0
(7) Citrate—50
(8) Histidine—0
(9) Glycogen—25
(10) 3-hydroxybutyrate—0
(11) 4-hydroxybenzoate—0
(12) Leucine arylamidase—50
(13) Valine arylamidase—25
(14) Phosphohydrolase—75
(15) α-galactosidase—75
(16) Ampicillin—100
(17) Fusidic Acid—100
(18) Methicillin—100
(19) Polymyxin—0
(20) Vancomycin—100
(21) Yellow colony—100
(22) Translucent colony—0
(23) Lipase—0
(24) Oxidase (10 seconds)—0.

22. A single strain of bacteria which is useful for the production of alkali-tolerant enzymes, wherein said strain is aerobic, Gram-negative, and rod-shaped, and is an obligate alkaliphile, forms cream to beige-colored, irregular, flat colonies, grows optimally between pH 8.2 and pH 10.9, and is classified at a 73% similarity level into a phenon based on A. a positive response to the following tests:
  (1) Starch
  (2) N-acetylglucosamine
  (3) Saccharose
  (4) Maltose
  (5) Acetate
  (6) Alanine
  (7) Citrate
  (8) Glycogen
  (9) 3-hydroxybutyrate
  (10) Penicillin G
  (11) Fusidic Acid
  (12) Methicillin
  (13) Tetracycline
  (14) Bacitracin;
B. a negative response in the following tests:
  (1) Pyruvate
  (2) 4-hydroxybenzoate
  (3) Leucine arylamidase
  (4) Valine arylamidase
  (5) α-galactosidase
  (6) Polymyxin.

23. A single strain of bacteria which is useful for the production of alkali-tolerant enzymes, wherein said strain is aerobic, Gram-negative, and rod-shaped, and is an obligate alkaliphile, forms cream to beige-colored, irregular, flat colonies, grows optimally between pH 8.2 and pH 10.9, and is classified at a 73% similarity level into a phenon based on the pattern of responses to tests leaving a probability matrix with a percentage distribution as follows:

(1) N-acetylglucosamine—100
(2) Saccharose—100
(3) Maltose—100
(4) Lactate—40
(5) Propionate—80
(6) Valerate—40
(7) Citrate—100
(8) Histidine—80
(9) Glycogen—100
(10) 3-hydroxybutyrate—100
(11) 4-hydroxybenzoate—0
(12) Leucine arylamidase—0
(13) Valine arylamidase—0
(14) phosphohydrolase—40
(15) α-galactosidase—0
(16) Ampicillin—80
(17) Fusidic Acid—100
(18) Methicillin—100
(19) Polymyxin—0
(20) Vancomycin—75
(21) Yellow colony—0
(22) Translucent colony—0
(23) Lipase—0
(24) Oxidase (10 seconds)—0.

24. A single strain of bacteria which is useful for production of alkali-tolerant enzymes, wherein said strain is aerobic, Gram-negative, motile, and rod-shaped, and is an obligate alkaliphile having the following characteristics:

(a) cells frequently in pairs;
(b) grows optimally between pH 9 and pH 10;
(c) on alkaline-agar, forms smooth, translucent, beige colored colonies, 1–2 mm in diameter which are circular, convex with an entire margin;
(d) in alkaline-broth, growth (37° C.) is flocculent with a ring or surface pellicle and formation of a sediment;
(e) grows optimally at 20° C. to 30° C.;
(f) no growth at 15° C. or 40° C.;
(g) KOH test is positive;
(h) aminopeptidase test is weak positive;
(i) oxidase test is weak positive;
(j) catalase test is positive;
(k) obligate halophile;
(l) grows optimally at 4% NaCl;
(m) no growth at 0% or 8% NaCl;
(n) hydrolysis of gelatin test is slow positive;
(o) hydrolysis of starch is positive;
(p) does not grow on simple sugars;
(q) does not grow on organic acids;
(r) grows on yeast extract and peptones.

25. A single strain of bacteria which is useful for production of alkali-tolerant enzymes, wherein said strain is aerobic, Gram-negative, motile, and rod-shaped, and is an obligate alkaliphile having the following characteristics:

(a) grows optimally between pH 8.2 and pH 10.9;
(b) on alkaline-agar, forms smooth, opaque, beige or brown colored colonies, 2–4 mm in diameter which are circular in form, convex in elevation, with an entire margin;
(c) in alkaline-broth, growth (37° C.) is heavy and flocculent with a sediment and surface pellicle;
(d) grows optimally between 20° C. and 37° C.;
(e) no growth at 8° C. or at 40° C. or above;
(f) KOH test is positive;
(g) aminopeptidase test is positive;
(h) oxidase test is very weakly positive;
(i) catalase test is positive;
(j) grows at a NaCl concentration of between 0% and 15%;
(k) no growth at 20% NaCl;
(l) hydrolysis of gelatin test is negative;
(m) hydrolysis of starch is negative;
(n) grows on yeast extract;
(o) grows on organic acids selected from the group consisting of succinate, pyruvate, citrate, malonate, acetate and lactate;
(p) grows on fatty acids selected from the group consisting of propionate, valerate and suberate;
(q) grows on amino acids selected from the group consisting of proline, serine, histidine and lysine.

26. A single strain of bacteria which is useful for production of alkali-tolerant enzymes, wherein said strain is aerobic, Gram-negative, and rod-shaped, and is an obligate alkaliphile having the following characteristics:

(a) grows optimally between pH 9 and pH 10.5;
(b) on alkaline-agar, forms smooth, opaque, brown-colored colonies, 3–4 mm in diameter which are fairly irregular in form, generally flat to slightly umbonate in elevation with a lobate margin;
(c) in alkaline-broth, growth (37° C.) is moderate to heavy, becoming flocculent with a sediment and surface pellicle;
(d) grows optimally between 20° C. and 40° C.;
(e) no growth at 45° C.;
(f) KOH test is positive;
(g) aminopeptidase test is positive;
(h) oxidase test is negative;
(i) catalase test is positive;
(j) grows at a NaCl concentration 0% to 12%;
(k) no growth at 20% NaCl;
(l) hydrolysis of gelatin test is positive;
(m) hydrolysis of starch is weakly positive;
(n) does not grow on simple sugars;
(o) grows on yeast extract;
(p) grows on organic acids selected from the group consisting of pyruvate, citrate, acetate and lactate;
(q) grows on fatty acids selected from the group consisting of propionate, caprate and valerate;
(r) grows on amino acids selected from the group consisting of proline, alanine and lysine.

27. A single strain of bacteria which is useful for production of alkali-tolerant enzymes, wherein said strain is aerobic, Gram-negative, and rod-shaped, and is an obligate alkaliphile having the following characteristics::
  (a) does not grow below pH 7.5;
  (b) on alkaline-agar, forms smooth, cream colored colonies, initially translucent but becoming opaque;
  (c) on alkaline-agar, the colonies develop from circular, entire and become irregular, lobate in form, with a convex elevation;
  (d) in alkaline-broth, growth (37° C.) is slow, slight, flocculent with a sediment but no surface pellicle;
  (e) grows optimally between 10° C. and 40° C.;
  (f) no growth at 8° C. or 45° C.;
  (g) KOH test is positive;
  (h) aminopeptidase test is negative;
  (i) oxidase test is positive;
  (j) catalase test is positive;
  (k) grows at an NaCl concentration of between 0% to 15%;
  (l) no growth at 20% NaCl;
  (m) hydrolysis of gelatin test is positive;
  (n) hydrolysis of starch is weakly positive;
  (o) grows on yeast extract and peptones;
  (p) grows on sugars;
  (q) grows on organic acids;
  (r) grows on amino acids.

28. A single strain of bacteria which is useful for production of alkali-tolerant enzymes, wherein said strain is aerobic, Gram-negative, small, and rod-shaped, and is an obligate alkaliphile having the following characteristics:
  (a) cells frequently form short chains;
  (b) does not grow below pH 8;
  (c) on alkaline-agar, forms smooth, circular, convex colonies with an entire margin, about 1 mm in diameter which are initially transparent, cream/beige in color, the colonies become opaque and brown in color with age;
  (d) in alkaline-broth, growth (37° C.) is initially evenly turbid with a sediment but no surface pellicle becoming flocculent with formation of a pellicle;
  (e) grows optimally between 30° C. and 37° C.;
  (f) no growth at 40° C.;
  (g) KOH test is positive;
  (h) aminopeptidase test is positive;
  (i) oxidase test is positive;
  (j) catalase test is positive;
  (k) obligate halophile;
  (l) grows at 4% NaCl;
  (m) no growth at 0% or 8% NaCl;
  (n) hydrolysis of gelatin test is slow positive;
  (o) hydrolysis of starch is negative;
  (p) grows on yeast extract and peptones;
  (q) grows on sugars;
  (r) grows on organic acids;
  (s) grows on fatty acids;
  (t) grows on amino acids.

* * * * *